United States Patent
Carson et al.

(10) Patent No.: US 9,505,768 B2
(45) Date of Patent: Nov. 29, 2016

(54) COMPOSITIONS AND METHODS FOR MODULATING TLR4

(71) Applicant: The Regents of the University of California, Oakland, CA (US)

(72) Inventors: Dennis A. Carson, La Jolla, CA (US); Howard B. Cottam, Escondido, CA (US); Tomoko Hayashi, San Diego, CA (US); Michael Chan, San Diego, CA (US); Mary P. Corr, San Diego, CA (US)

(73) Assignee: The Regents Of The University Of California, Oakland, CA (US)

( * ) Notice: Subject to any disclaimer, the term of this patent is extended or adjusted under 35 U.S.C. 154(b) by 0 days.

(21) Appl. No.: 14/671,820

(22) Filed: Mar. 27, 2015

(65) Prior Publication Data

US 2015/0197527 A1    Jul. 16, 2015

Related U.S. Application Data

(63) Continuation of application No. PCT/US2013/062298, filed on Sep. 27, 2013.

(60) Provisional application No. 61/706,294, filed on Sep. 27, 2012, provisional application No. 61/824,540, filed on May 17, 2013.

(51) Int. Cl.
| | | |
|---|---|---|
| *C07D 487/04* | (2006.01) | |
| *A61K 31/519* | (2006.01) | |
| *A61P 19/02* | (2006.01) | |
| *C07D 519/00* | (2006.01) | |
| *A61K 31/688* | (2006.01) | |
| *A61K 39/00* | (2006.01) | |
| *A61K 39/39* | (2006.01) | |

(52) U.S. Cl.
CPC ............ *C07D 487/04* (2013.01); *A61K 31/519* (2013.01); *A61K 31/688* (2013.01); *A61K 39/0005* (2013.01); *A61K 39/39* (2013.01); *C07D 519/00* (2013.01); *A61K 2039/55511* (2013.01)

(58) Field of Classification Search
CPC .......................... C07D 487/04; A61K 31/519
USPC .......................................... 544/250; 514/267
See application file for complete search history.

(56) References Cited

U.S. PATENT DOCUMENTS 5,326,868 A    7/1994 Thurkauf et al.

FOREIGN PATENT DOCUMENTS

| | | |
|---|---|---|
| WO | WO-2006/005063 A2 | 1/2006 |
| WO | WO-2006/005063 A3 | 1/2006 |
| WO | WO-2007/024707 A2 | 3/2007 |
| WO | WO-2007/024707 A3 | 3/2007 |
| WO | WO-2008/115319 A2 | 9/2008 |
| WO | WO-2008/115319 A3 | 9/2008 |
| WO | WO-2010/093436 A2 | 8/2010 |
| WO | WO-2010/093436 A3 | 8/2010 |
| WO | WO-2011/139348 A2 | 11/2011 |
| WO | WO-2011/139348 A3 | 11/2011 |
| WO | WO-2011/139348 A9 | 11/2011 |
| WO | WO-2012/065139 A2 | 5/2012 |
| WO | WO-2012/065139 A3 | 5/2012 |
| WO | WO-2012/065139 A8 | 5/2012 |
| WO | WO-2014/052828 A1 | 4/2014 |

OTHER PUBLICATIONS

Ohto et al., Microbes and Infection 16 (2014) 273-282.*
Yu et al. Biochimica et Biophysica Acta 1835 (2013) 144-154.*
Zhao et al., Frontiers in Immunology. 5, 1-6,2014.*
Freshney et al.,Culture of Animal Cells, A Manual of Basic Technique, Alan R. Liss, Inc., 1983, New York, p. 4.*
Dermer et al., Bio/Technology, 1994, 12:320.*
STN Search Feb. 22, 2016.*
Baldrick, P., et al. (Jul.-Aug. 2007). "Pollinex Quattro Ragweed: safety evaluation of a new allergy vaccine adjuvanted with monophosphoryl lipid A (MPL) for the treatment of ragweed pollen allergy," *J. Appl. Toxicol.* 27(4):399-409.
Chan, M., et al. (Jun. 13, 2013, e-published May 24, 2013). "Identification of substituted pyrimido[5,4-b]indoles as selective Toll-like receptor 4 ligands," *J. Med. Chem.* 56(11):4206-4223.
Coats, S.R., et al. (Oct. 1, 2005). "MD-2 mediates the ability of tetra-acylated and penta-acylated lipopolysaccharides to antagonize *Escherichia coli* lipopolysaccharide at the TLR4 signaling complex," *J. Immunol.* 175(7):4490-4498.
Devani, M. B. et al. (May 1976). "Synthesis of 3-substituted thieno [2, 3-d] pyrimidin-4(3H)-one-2-mercaptoacetic acids and their ethyl esters for pharmacological screening," *J. Pharm. Sci.* 65(5):660-664.
Dubuske, L., et al. (Feb. 2009). "Significant Reduction in Combined Symptom and Medication Score Compared With Placebo Following MPL-Adjuvanted uSCIT in Patients with Seasonal Grass Pollen Allergy," *J. Allergy Clin. Immunol.* 123:S216.
Hayashi, T. et al. (Aug. 2014, e-published Jun. 3, 2014). "Novel synthetic toll-like receptor 4/MD2 ligands attenuate sterile inflammation," *J Pharmacol Exp Ther* 350(2):330-340.
Hennessy, E.J., et al. (Apr. 2010). "Targeting Toll-like receptors emerging therpeutics?" *Nature Reviews* 2010, 9:283-307.
Hutchinson, M.R., et al. (Jun. 30, 2010, e-published Apr. 8, 2010). "Evidence that tricyclic small molecules may possess toll-like receptor and myeloid differentiation protein 2 activity," *Neuroscience* 168(2):551-563.

(Continued)

*Primary Examiner* — Venkataraman Balasubramanian
(74) *Attorney, Agent, or Firm* — Mintz Levin Cohn Ferris Flovsky and Popeo PC

(57) ABSTRACT

Provided herein, inter alia, are methods and compositions for modulating TLR-4.

14 Claims, 14 Drawing Sheets

(56) References Cited

OTHER PUBLICATIONS

Ii, M., et al. (Apr. 2006, e-published Dec. 22, 2005). "A novel cyclohexene derivative, ethyl (6R)-6-[N-(2-Chloro-4-fluorophenyl)sulfamoyl]cyclohex-1-ene-1-carboxylate (TAK-242), selectively inhibits toll-like receptor 4-mediated cytokine production through suppression of intracellular signaling," *Mol. Pharmacol.* 69(4):1288-1295.

International Search Report mailed on Feb. 3, 2014 for PCT Application No. PCT/US2013/062298, filed on Sep. 27, 2013, 4 pages.

Jiang, Z., et al. (Jun. 2005, e-published May 15, 2005). "CD14 is required for MyD88-independent LPS signaling," *Nature Immunol.* 6(6):565-570.

Ledeboer, A., et al. (Nov. 2006). "The glial modulatory drug AV411 attenuates mechanical allodynia in rat models of neuropathic pain," *Neuron Glia Biol.* 2(4)::279-291.

Ledeboer, A. et al. (Jul. 2007). "Ibudilast (AV-411). A new class therapeutic candidate for neuropathic pain and opioid withdrawal syndromes," *Expert Opin. Investig. Drugs* 16(7):935-950.

Medzhitov, R., et al. (Jul. 24, 1997). "A human homologue of the *Drosophila* Toll protein signals activation of adaptive immunity," *Nature* 388(6640):394-396.

Mullarkey, M., et al. (Mar. 2003). "Inhibition of endotoxin response by e5564, a novel Toll-like receptor 4-directed endotoxin antagonist," *J. Pharmacol. Exp. Ther.* 304(3):1093-1102.

Muroi, M. etal. (Mar. 3, 2006, e-published Dec. 31, 2005). "Structural regions of MD-2 that determine the agonist-antagonist activity of lipid Iva," *J. Biol. Chem.* 281(9):5484-5491.

Park, B.S., et al. (Apr. 30, 2009, e-published Mar. 1, 2009). "The structural basis of lipopolysaccharide recognition by the TLR4-MD-2 complex," *Nature* 458(7242):1191-1195.

Robijns, S.C. et al. (Jul. 2012, e-published May 8, 2012). "Identification and characterization of 4-[4-(3-phenyl-2-propen-1-yl)-1-piperazinyl]-5H-pyrimido[5,4-b]indole derivatives as *Salmonella* biofilm inhibitors," *FEMS Immunology & Medicinal Microbiolog* 65(2):390-394.

Saitoh, S. et al. (Jul. 2004). "Lipid A antagonist, lipid IVa, is distinct from lipid A in interaction with Toll-like receptor 4 (TLR4)-MD-2 and ligand-induced TLR4 oligomerization," *Int. Immunol.* 16(7):961-969.

Santagati, A. et al. (Dec. 1998). "Building a model of interaction at the NK-2 receptors: Polycondensed heterocycles containing the pyrimidoindole skeleton," *European Journal of Medicinal Chemistry* 32(12):973-985.

Shimazu, R. et al. (Jun. 7, 1999). "MD-2, a molecule that confers lipopolysaccharide responsiveness on Toll-like receptor 4," *J. Exp. Med.* 189(11):1777-1782.

Ungaro, R., et al. (Jun. 2009, e-published Apr. 9, 2009). "A novel Toll-like receptor 4 antagonist antibody ameliorates inflammation but impairs mucosal healing in murine colitis," *Am. J. Physiol. Gastrointest. Liver Physiol.* 296(6):G1167-G1179.

Written Opinion mailed on Feb. 3, 2014 for PCT Application No. PCT/US2013/062298, filed on Sep. 27, 2013, 10 pages.

CAS RN: 536703-68-1, 1 page.
CAS RN: 537668-77-2, 1 page.
CAS RN: 536703-58-9, 1 page.
CAS RN: 536703-59-0, 1 page.
CAS RN: 536703-86-3, 1 page.
CAS RN: 536703-61-4, 1 page.
CAS RN: 536703-73-8, 1 page.
CAS RN: 536703-77-2, 1 page.
CAS RN: 536703-74-9, 1 page.
CAS RN: 536711-08-7, 1 page.
CAS RN: 536704-64-0, 1 page.

* cited by examiner

SEQUENCE LISTING

```
<160> NUMBER OF SEQ ID NOS: 2

<210> SEQ ID NO 1
<211> LENGTH: 835
<212> TYPE: PRT
<213> ORGANISM: Mus musculus

<400> SEQUENCE: 1

Met Met Pro Pro Trp Leu Leu Ala Arg Thr Leu Ile Met Ala Leu Phe
1               5                   10                  15

Phe Ser Cys Leu Thr Pro Gly Ser Leu Asn Pro Cys Ile Glu Val Val
                20                  25                  30

Pro Asn Ile Thr Tyr Gln Cys Met Asp Gln Lys Leu Ser Lys Val Pro
            35                  40                  45
```

-continued

```
Asp Asp Ile Pro Ser Ser Thr Lys Asn Ile Asp Leu Ser Phe Asn Pro
    50                  55                  60

Leu Lys Ile Leu Lys Ser Tyr Ser Phe Ser Asn Phe Ser Glu Leu Gln
65                  70                  75                  80

Trp Leu Asp Leu Ser Arg Cys Glu Ile Glu Thr Ile Glu Asp Lys Ala
                85                  90                  95

Trp His Gly Leu His His Leu Ser Asn Leu Ile Leu Thr Gly Asn Pro
            100                 105                 110

Ile Gln Ser Phe Ser Pro Gly Ser Phe Ser Gly Leu Thr Ser Leu Glu
            115                 120                 125

Asn Leu Val Ala Val Glu Thr Lys Leu Ala Ser Leu Glu Ser Phe Pro
    130                 135                 140

Ile Gly Gln Leu Ile Thr Leu Lys Lys Leu Asn Val Ala His Asn Phe
145                 150                 155                 160

Ile His Ser Cys Lys Leu Pro Ala Tyr Phe Ser Asn Leu Thr Asn Leu
                165                 170                 175

Val His Val Asp Leu Ser Tyr Asn Tyr Ile Gln Thr Ile Thr Val Asn
            180                 185                 190

Asp Leu Gln Phe Leu Arg Glu Asn Pro Gln Val Asn Leu Ser Leu Asp
            195                 200                 205

Met Ser Leu Asn Pro Ile Asp Phe Ile Gln Asp Gln Ala Phe Gln Gly
    210                 215                 220

Ile Lys Leu His Glu Leu Thr Leu Arg Gly Asn Phe Asn Ser Ser Asn
225                 230                 235                 240

Ile Met Lys Thr Cys Leu Gln Asn Leu Ala Gly Leu His Val His Arg
                245                 250                 255

Leu Ile Leu Gly Glu Phe Lys Asp Glu Arg Asn Leu Glu Ile Phe Glu
            260                 265                 270

Pro Ser Ile Met Glu Gly Leu Cys Asp Val Thr Ile Asp Glu Phe Arg
            275                 280                 285

Leu Thr Tyr Thr Asn Asp Phe Ser Asp Asp Ile Val Lys Phe His Cys
    290                 295                 300

Leu Ala Asn Val Ser Ala Met Ser Leu Ala Gly Val Ser Ile Lys Tyr
305                 310                 315                 320

Leu Glu Asp Val Pro Lys His Phe Lys Trp Gln Ser Leu Ser Ile Ile
                325                 330                 335

Arg Cys Gln Leu Lys Gln Phe Pro Thr Leu Asp Leu Pro Phe Leu Lys
            340                 345                 350

Ser Leu Thr Leu Thr Met Asn Lys Gly Ser Ile Ser Phe Lys Lys Val
            355                 360                 365

Ala Leu Pro Ser Leu Ser Tyr Leu Asp Leu Ser Arg Asn Ala Leu Ser
    370                 375                 380

Phe Ser Gly Cys Cys Ser Tyr Ser Asp Leu Gly Thr Asn Ser Leu Arg
385                 390                 395                 400

His Leu Asp Leu Ser Phe Asn Gly Ala Ile Ile Met Ser Ala Asn Phe
                405                 410                 415

Met Gly Leu Glu Glu Leu Gln His Leu Asp Phe Gln His Ser Thr Leu
            420                 425                 430

Lys Arg Val Thr Glu Phe Ser Ala Phe Leu Ser Leu Glu Lys Leu Leu
            435                 440                 445
```

```
Tyr Leu Asp Ile Ser Tyr Thr Asn Thr Lys Ile Asp Phe Asp Gly Ile
    450                 455                 460

Phe Leu Gly Leu Thr Ser Leu Asn Thr Leu Lys Met Ala Gly Asn Ser
465                 470                 475                 480

Phe Lys Asp Asn Thr Leu Ser Asn Val Phe Ala Asn Thr Thr Asn Leu
                485                 490                 495

Thr Phe Leu Asp Leu Ser Lys Cys Gln Leu Glu Gln Ile Ser Trp Gly
                500                 505                 510

Val Phe Asp Thr Leu His Arg Leu Gln Leu Leu Asn Met Ser His Asn
            515                 520                 525

Asn Leu Leu Phe Leu Asp Ser Ser His Tyr Asn Gln Leu Tyr Ser Leu
530                 535                 540

Ser Thr Leu Asp Cys Ser Phe Asn Arg Ile Glu Thr Ser Lys Gly Ile
545                 550                 555                 560

Leu Gln His Phe Pro Lys Ser Leu Ala Phe Phe Asn Leu Thr Asn Asn
                565                 570                 575

Ser Val Ala Cys Ile Cys Glu His Gln Lys Phe Leu Gln Trp Val Lys
                580                 585                 590

Glu Gln Lys Gln Phe Leu Val Asn Val Glu Gln Met Thr Cys Ala Thr
            595                 600                 605

Pro Val Glu Met Asn Thr Ser Leu Val Leu Asp Phe Asn Asn Ser Thr
            610                 615                 620

Cys Tyr Met Tyr Lys Thr Ile Ile Ser Val Ser Val Ser Val Ile
625                 630                 635                 640

Val Val Ser Thr Val Ala Phe Leu Ile Tyr His Phe Tyr Phe His Leu
                645                 650                 655

Ile Leu Ile Ala Gly Cys Lys Lys Tyr Ser Arg Gly Glu Ser Ile Tyr
                660                 665                 670

Asp Ala Phe Val Ile Tyr Ser Ser Gln Asn Glu Asp Trp Val Arg Asn
            675                 680                 685

Glu Leu Val Lys Asn Leu Glu Glu Gly Val Pro Arg Phe His Leu Cys
            690                 695                 700

Leu His Tyr Arg Asp Phe Ile Pro Gly Val Ala Ile Ala Ala Asn Ile
705                 710                 715                 720

Ile Gln Glu Gly Phe His Lys Ser Arg Lys Val Ile Val Val Ser
                725                 730                 735

Arg His Phe Ile Gln Ser Arg Trp Cys Ile Phe Glu Tyr Glu Ile Ala
                740                 745                 750

Gln Thr Trp Gln Phe Leu Ser Ser Arg Ser Gly Ile Ile Phe Ile Val
            755                 760                 765

Leu Glu Lys Val Glu Lys Ser Leu Leu Arg Gln Gln Val Glu Leu Tyr
770                 775                 780

Arg Leu Leu Ser Arg Asn Thr Tyr Leu Glu Trp Glu Asp Asn Pro Leu
785                 790                 795                 800

Gly Arg His Ile Phe Trp Arg Arg Leu Lys Asn Ala Leu Leu Asp Gly
                805                 810                 815
```

```
Lys Ala Ser Asn Pro Glu Gln Thr Ala Glu Glu Glu Gln Glu Thr Ala
            820                 825                 830

Thr Trp Thr
        835

<210> SEQ ID NO 2
<211> LENGTH: 160
<212> TYPE: PRT
<213> ORGANISM: Mus musculus

<400> SEQUENCE: 2

Met Leu Pro Phe Ile Leu Phe Ser Thr Leu Leu Ser Pro Ile Leu Thr
1               5                   10                  15

Glu Ser Glu Lys Gln Gln Trp Phe Cys Asn Ser Ser Asp Ala Ile Ile
            20                  25                  30

Ser Tyr Ser Tyr Cys Asp His Leu Lys Phe Pro Ile Ser Ile Ser Ser
        35                  40                  45

Glu Pro Cys Ile Arg Leu Arg Gly Thr Asn Gly Phe Val His Val Glu
    50                  55                  60

Phe Ile Pro Arg Gly Asn Leu Lys Tyr Leu Tyr Phe Asn Leu Phe Ile
65                  70                  75                  80

Ser Val Asn Ser Ile Glu Leu Pro Lys Arg Lys Glu Val Leu Cys His
                85                  90                  95

Gly His Asp Asp Asp Tyr Ser Phe Cys Arg Ala Leu Lys Gly Glu Thr
            100                 105                 110

Val Asn Thr Ser Ile Pro Phe Ser Phe Glu Gly Ile Leu Phe Pro Lys
        115                 120                 125

Gly His Tyr Arg Cys Val Ala Glu Ala Ile Ala Gly Asp Thr Glu Glu
    130                 135                 140

Lys Leu Phe Cys Leu Asn Phe Thr Ile Ile His Arg Arg Asp Val Asn
145                 150                 155                 160
```

COMPOSITIONS AND METHODS FOR MODULATING TLR4

CROSS-REFERENCES TO RELATED APPLICATIONS

This application is a continuation of International Appl. No. PCT/US2013/062298, filed Sep. 27, 2013, which claims the benefit of U.S. Provisional Appl. No. 61/706,294, filed Sep. 27, 2012, and U.S. Provisional Appl. No. 61/824,540, filed May 17, 2013, each of which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with government support under Grant No. HHSN272200900034C awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 48537-528N01US_ST25.TXT, created on Mar. 24, 2015, 9,086 bytes, machine format IBM-PC, MS Windows operating system, is hereby incorporated by reference.

BACKGROUND OF THE INVENTION

The innate immune response is the first line of defense against microbial pathogens such as viruses, bacteria, fungi, and protozoa. A critical component of the innate immune response is the $NF_\kappa B$ family of transcription factors. See e.g., Dev, A. et al., *Curr. Top. Microbiol. Immunol.* 2011, 34: 115-143; Li, Q. & Verma, I. M., *Nature Rev. Immunol.* 2002, 2:725-734). The Toll-like receptors (TLRs) are critical components of the innate immune system that regulate $NF_\kappa B$ activation. In general, the TLRs recognize macromolecules that are associated with pathogens and with cell stress. These pathogen-associated molecular patterns (PAMPs) and their corresponding TLRs include: lipopeptides (TLR2), double-stranded RNA (TLR3), lipopolysaccharide (LPS) (TLR4) (Fang, H. et al., *J. Biol. Chem.* 2011, 286:30393-30400), bacterial flagellin (TLR5), guanine and uridine-rich single-stranded RNA (TLR7, 8), and hypo-methylated CpG rich DNA (TLR9) (Hemmi, H. et al., *Nature* 2000, 408:740-745) Innate immune cells use pattern recognition receptors (PRRs) such as TLRs to promote a rapid response to perceived threats before pathogen-specific adaptive immunity can be established. Indeed, this rapid response, involving multiple components of the innate immune system, has been recognized to guide the type of adaptive immune response that is most effective for the specific pathogenic threat.

Provided herein, inter alia, are compounds and methods useful in modulating innate immune responses.

BRIEF SUMMARY OF THE INVENTION

In a first aspect, there is provided a pharmaceutical composition including a pharmaceutically acceptable excipient and compound having the formula:

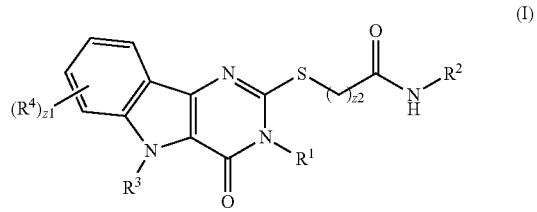

or a pharmaceutically acceptable salt thereof, wherein z1 is an integer from 0 to 4; z2 is an integer from 0 to 5; $R^1$ is substituted or unsubstituted cycloalkyl, substituted or unsubstituted heterocycloalkyl, substituted or unsubstituted aryl, or substituted or unsubstituted heteroaryl; $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, or substituted or unsubstituted alkyl; and $R^4$ is independently halogen, —CN, —SH, —OH, —COOH, —$NH_2$, —$CONH_2$, nitro, —$CF_3$, —$CCl_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In another aspect, there is provided a vaccine including an antigen and a compound having the formula:

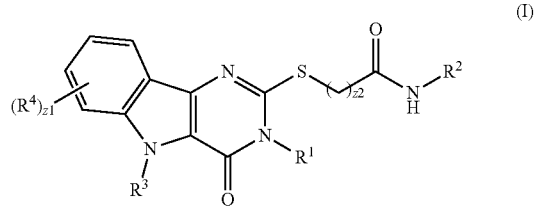

or a pharmaceutically acceptable salt thereof, wherein z1 is an integer from 0 to 4; z2 is an integer from 0 to 5; $R^1$ is substituted or unsubstituted cycloalkyl, substituted or unsubstituted heterocycloalkyl, substituted or unsubstituted aryl, or substituted or unsubstituted heteroaryl; $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, or substituted or unsubstituted alkyl; and $R^4$ is independently halogen, —CN, —SH, —OH, —COOH, —$NH_2$, —$CONH_2$, nitro, —$CF_3$, —$CCl_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In another aspect, there is provided a biological cell including a compound having the formula:

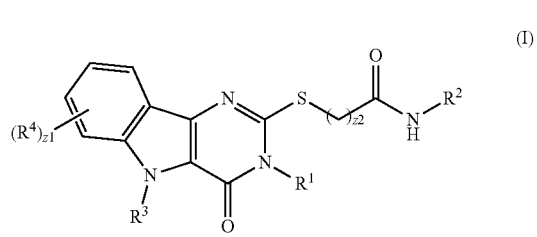

or a pharmaceutically acceptable salt thereof, wherein z1 is an integer from 0 to 4; z2 is an integer from 0 to 5; $R^1$ is substituted or unsubstituted cycloalkyl, substituted or unsubstituted heterocycloalkyl, substituted or unsubstituted aryl, or substituted or unsubstituted heteroaryl; $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, or substituted or unsubstituted alkyl; and $R^4$ is independently halogen, —CN, —SH, —OH, —COOH, —NH$_2$, —CONH$_2$, nitro, —CF$_3$, —CCl$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In another aspect, there is provided a mixture including a TLR modulator and a compound having the formula:

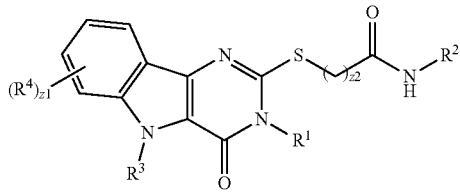

(I)

or a pharmaceutically acceptable salt thereof, wherein z1 is an integer from 0 to 4; z2 is an integer from 0 to 5; $R^1$ is substituted or unsubstituted cycloalkyl, substituted or unsubstituted heterocycloalkyl, substituted or unsubstituted aryl, or substituted or unsubstituted heteroaryl; $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, or substituted or unsubstituted alkyl; and $R^4$ is independently halogen, —CN, —SH, —OH, —COOH, —NH$_2$, —CONH$_2$, nitro, —CF$_3$, —CCl$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In another aspect, there is provided a method of modulating a Toll-like receptor 4 protein, the method including contacting the Toll-like receptor 4 protein with a compound having the formula:

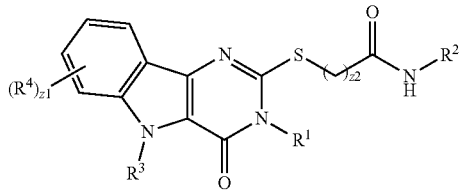

(I)

or a pharmaceutically acceptable salt thereof, wherein z1 is an integer from 0 to 4; z2 is an integer from 0 to 5; $R^1$ is substituted or unsubstituted cycloalkyl, substituted or unsubstituted heterocycloalkyl, substituted or unsubstituted aryl, or substituted or unsubstituted heteroaryl; $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, or substituted or unsubstituted alkyl; and $R^4$ is independently halogen, —CN, —SH, —OH, —COOH, —NH$_2$, —CONH$_2$, nitro, —CF$_3$, —CCl$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In another aspect, there is provided a method of modulating an immune response in a subject in need thereof, the method including administering to the subject an effective amount of a compound having the formula:

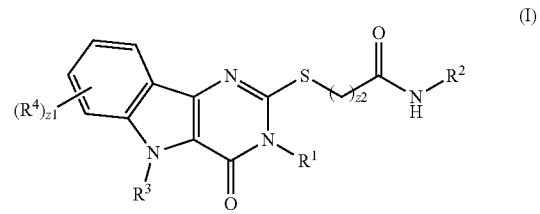

(I)

or a pharmaceutically acceptable salt thereof, wherein z1 is an integer from 0 to 4; z2 is an integer from 0 to 5; $R^1$ is substituted or unsubstituted cycloalkyl, substituted or unsubstituted heterocycloalkyl, substituted or unsubstituted aryl, or substituted or unsubstituted heteroaryl; $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, or substituted or unsubstituted alkyl; and $R^4$ is independently halogen, —CN, —SH, —OH, —COOH, —NH$_2$, —CONH$_2$, nitro, —CF$_3$, —CCl$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In another aspect, there is provided a method of decreasing inflammation in a subject in need thereof, the method including administering to the subject an effective amount of a compound having the formula:

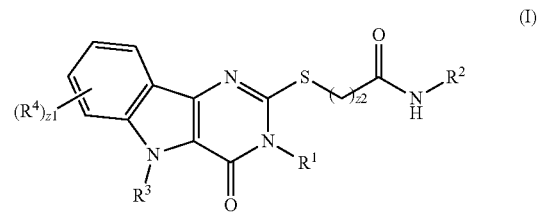

(I)

or a pharmaceutically acceptable salt thereof, wherein z1 is an integer from 0 to 4; z2 is an integer from 0 to 5; $R^1$ is substituted or unsubstituted cycloalkyl, substituted or unsubstituted heterocycloalkyl, substituted or unsubstituted aryl, or substituted or unsubstituted heteroaryl; $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, or substituted or unsubstituted alkyl; and $R^4$ is independently halogen, —CN, —SH, —OH, —COOH, —NH$_2$, —CONH$_2$, nitro, —CF$_3$, —CCl$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In another aspect, there is provided a compound having the formula:

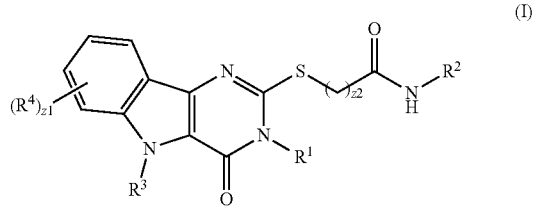
(I)

or a pharmaceutically acceptable salt thereof, wherein z1 is an integer from 0 to 4; z2 is an integer from 0 to 5; $R^1$ is substituted or unsubstituted cycloalkyl, substituted or unsubstituted heterocycloalkyl, substituted or unsubstituted aryl, or substituted or unsubstituted heteroaryl; $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, or substituted or unsubstituted alkyl; $R^4$ is independently halogen, —CN, —SH, —OH, —COOH, —NH$_2$, —CONH$_2$, nitro, —CF$_3$, —CCl$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein:
(i) the compound is not

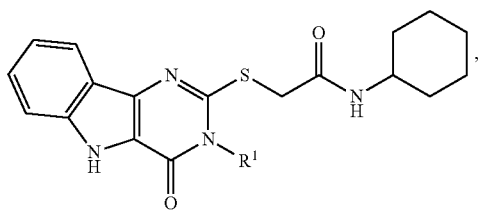

wherein $R^1$ is p-fluorophenyl or p-methylphenyl; (ii) wherein the compound is not

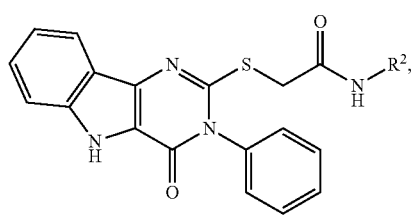

wherein $R^2$ is unsubstituted aryl, unsubstituted cyclohexyl, unsubstituted thiazole, or —CH$_2$-furanyl; or (iii) $R^3$ is not hydrogen.

BRIEF DESCRIPTION OF THE DRAWINGS

FIG. 3A: Histogram showing (in order left to right) Human TLR2, TLR3, TLR4/MD-2/CD14, TLR5, TLR7, TLR8, and TLR9. HEK293 Blue cells or NF-κB/SEAPorter cells were incubated with Cmpd 1 (10 μM) for 20-24 h, and activation was evaluated by SEAP secretion in the culture supernatants by colorimetric assay at OD$_{405}$. Data shown are mean±SEM of triplicates and representative of two to three independent experiments showing similar results. p<0.05 was considered significant compared to the vehicle control using Student's t test. Legend: Cmpd 1, closed box; vehicle, open box. FIGS. 3B, 3C: Mouse (FIG. 3B) or human (FIG. 3C) TLR4 HEK transfectomas were incubated with graded concentrations of Cmpd 1. TLR4 mediated NFκB activation was measured by SEAP secretion in the culture supernatant. FIG. 3D: WT and Tlr$^{-/-}$ mBMDC were incubated with Cmpd 1 (10 μM) for 18 h. IL-6 in the culture supernatants was measured by ELISA. FIG. 3E: Mouse TLR4 transfectoma cells were incubated with 2.5 μM compound 1 in the presence or absence of TLR4 antagonist LPS-RS. Histogram order (left to right); vehicle, zero, 12, 111, 1000 ng/mL LPS-RS). Activation of the TLR4/NFκB pathway was evaluated by SEAP secretion in the culture supernatants. * denotes p<0.05 considered as significant compared to vehicle using one way ANOVA with Dunnett's post hoc testing. FIGS. 3F, 3G: Histogram depicting WT and Cd14$^{-/-}$ mBMDC (left to right) were incubated with Cmpd 1 (3.7 μM) overnight. IL-6 in the culture supernatants was measured by ELISA (FIG. 3F) and type I IFN (IFN-β) measured by luciferase release from an ISRE reporter cell line (FIG. 3G). p<0.05 was considered as significant compared to vehicle using Student's t test. NS denotes "not significant". Data shown are mean±SEM of triplicates and representative of two independent experiments showing similar results.

were incubated with graded concentrations of the compounds for 18 h and compared with vehicle (0.5% DMSO) and MPLA (1 µg/mL). (FIG. 6A) IL-6 levels in the culture supernatants were determined by ELISA. (FIG. 6B) The cells were lysed after the overnight incubation with MTT reagents, and absorbance at 570 nm was measured, subtracting the reference absorbance at 650 nm. Data shown are mean±SEM of triplicates and are representative of two independent experiments showing similar results. Legend: Cmpd 1, closed box; Cmpd 42, open box; MPLA, star-symbol; vehicle, open circle.

FIG. 11A: Schematic showing that C57BL/6 mice were intraperitoneally injected with 500 nmol Cmpd. 42 (n=11) or Cmpd 33 (n=11). 40 µg MPLA (n=9) and vehicle (n=9) were used as positive and negative controls, respectively. Next day, mice were challenged with LPS (0.2 µg/animal) and galactosamine (12 mg/animal). FIG. 11B: Histogram showing results of sera collected 1.5 h post challenge and measured for TNFα. *:p<0.05 compared to vehicle treated mice.

FIG. 15G: IFNγ in the culture supernatant was measured. Legend (time courses FIGS. 15A-15B): Cmpd 42, closed box; Cmpd 33, triangle; 1V270, closed diamond; 1V270+Cmpd 42, closed circle, darker gray; MPLA/Alum, open diamond; vehicle, closed circle, lighter gray. Legend (histograms FIGS. 15C-15G): FIG. 15C: IgG1, day 14; FIG. 15D: IgG2c, day 14; FIG. 15E: IgG1, day 28; FIG. 15F: IgG2c, day 28. Symbols: C42: Cmpd 42; C33: Cmpd 33; 270: compound 1V270; 270+C42: combination of 1V270+Cmpd 42; MPL/Alum: combination of MPL+Alum; Veh: vehicle.

DETAILED DESCRIPTION OF THE INVENTION

I. Definitions

Figure 1:
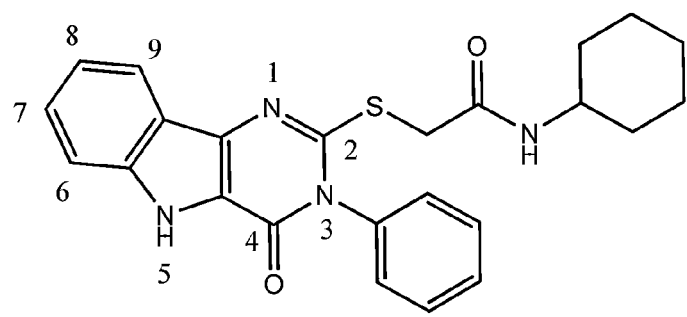
FIG. 1 depicts the structure of Cmpd 1.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two heteroatoms may be consecutive, such as, for example, —CH$_2$—NH—OCH$_3$.

The term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'.

Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (e.g., from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxyl)propyl, and the like).

The term "oxo," as used herein, means an oxygen that is double bonded to a carbon atom.

The term "alkylsulfonyl," as used herein, means a moiety having the formula —S(O)$_2$—R', where R' is an alkyl group as defined above. R' may have a specified number of carbons (e.g., "C$_1$-C$_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR)$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —CCl$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —CCl$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:
 (a) oxo, —OH, —NH$_2$, —SH, —CN, —CF$_3$, —CCl$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
 (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —CCl$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In some embodiments, a compound as described herein may include multiple instances of a substituent e.g. R$^{1A}$, R$^{1B}$, R$^{1C}$, R$^{2A}$, R$^{2B}$, R$^{2C}$, R$^{3A}$, R$^4$, R$^{4A}$, R$^{4B}$, R$^{4C}$, R$^{6A}$, R$^{6B}$, R$^{6C}$, R$^7$, R$^{7A}$, R$^{7B}$, and/or R$^{7C}$. In such embodiments, each substituent may optional be different at each occurrence and be appropriately labeled to distinguish each group for greater clarity. For example, where each R$^{1A}$ is different, they may be referred to as e.g., R$^{1A.1}$, R$^{1A.2}$, R$^{1A.3}$, R$^{1A.4}$, R$^{1A.5}$, and the like, wherein the definition of R$^{1A}$ is assumed by R$^{1A.1}$, R$^{1A.2}$, R$^{1A.3}$, R$^{1A.4}$, R$^{1A.5}$, and the like. Similarly, where any of R$^{1B}$, R$^{1C}$, R$^{2A}$, R$^{2B}$, R$^{2C}$, R$^{3A}$, R$^4$, R$^{4A}$, R$^{4B}$, R$^{4C}$, R$^{6A}$, R$^{6B}$, R$^{6C}$, R$^7$, R$^{7A}$, R$^{7B}$, and/or R$^{7C}$ multiply occur, the definition of each occurrence of R$^{1B}$, R$^{1C}$, R$^{2A}$, R$^{2B}$, R$^{2C}$, R$^{3A}$, R$^4$, R$^{4A}$, R$^{4B}$, R$^{4C}$, R$^{6A}$, R$^{6B}$, R$^{6C}$, R$^7$, R$^{7A}$, R$^{7B}$, and/or R$^{7C}$ assumes the definition of RIB, R$^{1C}$, R$^{2A}$, R$^{2B}$, R$^{2C}$, R$^{3A}$, R$^4$, R$^{4A}$, R$^{4B}$, R$^{4C}$, R$^{6A}$, R$^{6B}$, R$^{6C}$, R$^7$, R$^{7A}$, R$^{7B}$, and/or R$^{7C}$, respectively.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. A candidate molecule or compound described herein may be in an amount in a formulation or medicament, which is an amount that can lead to a biological effect, or lead to ameliorating, alleviating, lessening, relieving, diminishing or removing symptoms of a condition, e.g., disease, for example. The terms also can refer to reducing or stopping a cell proliferation rate (e.g., slowing or halting tumor growth) or reducing the number of proliferating cancer cells (e.g., removing part or all of a tumor). These terms also are applicable to reducing a titer of a microorganism (microbe) in a system (e.g., cell, tissue, or subject) infected with a microbe, reducing the rate of microbial propagation, reducing the number of symptoms or an effect of a symptom associated with the microbial infection, and/or removing detectable amounts of the microbe from the system. Examples of microbe include but are not limited to virus, bacterium and fungus.

The terms "subject," "patient" or "subject in need thereof" refers to a living organism suffering from or prone to a disease or condition that can be treated by administration of a compound, pharmaceutical composition, mixture or vaccine as provided herein. Non-limiting examples include humans, other mammals, bovines, rats, mice, dogs, monkeys, goat, sheep, cows, deer, and other non-mammalian animals. In some embodiments, a patient is human. In some embodiments, a patient is a domesticated animal. In some embodiments, a patient is a dog. In some embodiments, a patient is a parrot. In some embodiments, a patient is livestock animal. In some embodiments, a patient is a mammal. In some embodiments, a patient is a cat. In some embodiments, a patient is a horse. In some embodiments, a patient is bovine. In some embodiments, a patient is a canine. In some embodiments, a patient is a feline. In some embodiments, a patient is an ape. In some embodiments, a patient is a monkey. In some embodiments, a patient is a mouse. In some embodiments, a patient is an experimental animal. In some embodiments, a patient is a rat. In some embodiments, a patient is a hamster. In some embodiments, a patient is a test animal. In some embodiments, a patient is a newborn animal. In some embodiments, a patient is a newborn human. In some embodiments, a patient is a newborn mammal. In some embodiments, a patient is an elderly animal. In some embodiments, a patient is an elderly human. In some embodiments, a patient is an elderly mammal. In some embodiments, a patient is a geriatric patient.

The term "effective amount" as used herein refers to an amount effective to achieve an intended purpose. Accordingly, the terms "therapeutically effective amount" and the like refer to an amount of a compound, mixture or vaccine, or an amount of a combination thereof, to treat or prevent a disease or disorder, or to treat a symptom of the disease or disorder, in a subject in need thereof.

The term "antibody" or "antibodies" as used herein refers to all types of immunoglobulins, including IgG, IgM, IgA, IgD, and IgE, and any sub-isotype, including IgG1, IgG2a, IgG2b, IgG2c, IgG3 and IgG4, IgE1, IgE2, etc., and may include Fab or antigen-recognition fragments thereof. The antibodies may be monoclonal or polyclonal and may be of any species of origin, including e.g., mouse, rat, rabbit, horse, or human, or may be chimeric antibodies. See, e.g., M. Walker et al., *Molec. Immunol.* 1989, 26:403-11; Morrision et al., *Proc. Nat'l. Acad. Sci.,* 1984, 81:6851; Neuberger et al, *Nature,* 1984, 312:604. The antibodies may be recombinant monoclonal antibodies produced according to the methods disclosed in U.S. Pat. No. 4,474,893 (Reading) or U.S. Pat. No. 4,816,567 (Cabilly et al.). The antibodies may also be chemically constructed by specific antibodies made according to the method disclosed in U.S. Pat. No. 4,676,980 (Segel et al).

The term "antigen" refers, in the usual and customary sense, to a substance that binds specifically to an antibody or that can be recognized by antigen receptors (e.g., B-cell receptor, T-cell receptor and the like) of the adaptive immune system.

The terms "immune response" and the like refer, in the usual and customary sense, to a response by an organism that protects against disease. The response can be mounted by the innate immune system or by the adaptive immune system, as well known in the art.

The terms "modulating immune response" and the like refer to a change in the immune response of a subject as a consequence of administration of an agent, e.g., a compound with structure of Formula (I) as disclosed herein, including embodiments thereof. The term "modulating" as used herein refers to either increasing or decreasing the level of activity of the modulated entity, e.g., immune response. Accordingly, an immune response can be activated or deactivated as a consequence of administration of an agent, e.g., a compound with structure of Formula (I) as disclosed herein, including embodiments thereof. The term "activated" means an enhancement in the activity of the activated entity. The term "deactivated" means a diminution in the activity of the deactivated entity. In some embodiment, a deactivated immune response is nonetheless measurable, albeit at a reduced level compared to levels absent deactivation.

The term "TLR" refers to Toll-like receptors which are are critical components of the innate immune system that regulate NF$_\kappa$B activation, as well known in the art.

The terms "TLR modulator," "TLR immunomodulator" and the like as used herein refer, in the usual and customary sense, to compounds which agonize or antagonize a Toll Like Receptor. See e.g., PCT/US2010/000369, Hennessy, E. J., et al., *Nature Reviews* 2010, 9:283-307; PCT/US2008/001631; PCT/US2006/032371; PCT/US2011/000757. Accordingly, a "TLR agonist" is a TLR modulator which agonizes a TLR, and a "TLR antagonist" is a TLR modulator which antagonizes a TLR.

The term "TLR2" as used herein refers to the product (NCBI Accession AAH33756.1) of the TLR2 gene, and homologs and functional fragments thereof.

The term "TLR3" as used herein refers to the product (NCBI Accession ABC86910.1) of the TLR3 gene, and homologs and functional fragments thereof.

The term "TLR4" as used herein refers to the product of the TLR4 gene, and homologs, isoforms, and functional fragments thereof: Isoform 1 (NCBI Accession NP_612564.1); Isoform 2 (NCBI Accession NP_003257.1); Isoform 3 (NCBI Accession NP_612567.1).

The term "TLR5" as used herein refers to the product (NCBI Accession AAI09119) of the TLR5 gene, and homologs, and functional fragments thereof.

The term "TLR7" as used herein refers to the product (NCBI Accession AAZ99026) of the TLR7 gene, and homologs, and functional fragments thereof.

The term "TLR8" as used herein refers to the product (NCBI Accession AAZ95441) of the TLR8 gene, and homologs, and functional fragments thereof.

The term "TLR9" as used herein refers to the product (NCBI Accession AAZ95520) of the TLR9 gene, and homologs, and functional fragments thereof.

The terms "inflammation" and the like refer, in the usual and customary sense, to the pain, heat, erythema, swelling and/or loss of function that accompanies the complex biological response of tissues (e.g., vascular tissue) to harmful stimuli (e.g., pathogen invasion, damage to cells, irritants, and the like). Mediators of inflammation include plasma derived mediates such as bradykinin, C3, C5a, Factor XII, membrane attack complex, plasmin, and thrombin, as known in the art. Cell derived mediators of inflammation include lysosome granulates, histamine, IFN-γ, IL-8, leukotriene B4, nitric oxide, prostaglandins, TNF-α and IL-1. Accordingly, the terms "decrease inflammation" and the like mean that inflammation, as judged by assays well known in the art, is reduced relative to that observed in the absence of the compound having the structure of any one of Formulae (I) to (V) (e.g., Formulae (I) or (II)) as disclosed herein, including embodiments thereof, or a pharmaceutically acceptable salt thereof.

II. Compounds

In one aspect, there is provided a compound with structure of Formula (I):

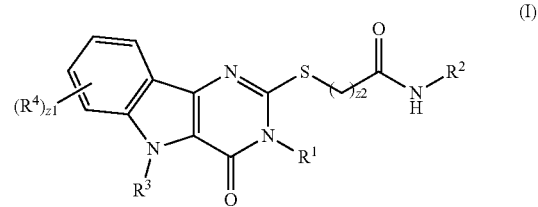

or a pharmaceutically acceptable salt thereof. In Formula (I), z1 is an integer from 0 to 4, and z2 is an integer from 0 to 5. $R^1$ is substituted or unsubstituted cycloalkyl, substituted or unsubstituted heterocycloalkyl, substituted or unsubstituted aryl, or substituted or unsubstituted heteroaryl. $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is hydrogen, or substituted or unsubstituted alkyl. $R^4$ is independently halogen, —CN, —SH, —OH, —COOH, —NH$_2$, —CONH$_2$, nitro, —CF$_3$, —CCl$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In one embodiment, $R^1$ is $R^{1A}$-substituted or unsubstituted cycloalkyl, $R^{1A}$ substituted or unsubstituted heterocycloalkyl, $R^{1A}$ substituted or unsubstituted aryl, or $R^{1A}$ substituted or unsubstituted heteroaryl. $R^{1A}$ is independently halogen, —CN, —CF$_3$, —CCl$_3$, —OH, —NH$_2$, —SO$_2$, —COOH, oxo, nitro, —SH, —CONH$_2$, $R^{1B}$-substituted or unsubstituted alkyl, $R^{1B}$-substituted or unsubstituted heteroalkyl, $R^{1B}$-substituted or unsubstituted cycloalkyl, $R^{1B}$-substituted or unsubstituted heterocycloalkyl, $R^{1B}$-substituted or unsubstituted aryl, or $R^{1B}$-substituted or unsubstituted heteroaryl. $R^{1B}$ is independently halogen, —CN, —CF$_3$, —CCl$_3$, —OH, —NH$_2$, —SO$_2$, —COOH, oxo, nitro, —SH, —CONH$_2$, $R^{1C}$-substituted or unsubstituted alkyl, $R^{1C}$-substituted or unsubstituted heteroalkyl, $R^{1C}$-substituted or unsubstituted cycloalkyl, $R^{1C}$-substituted or unsubstituted heterocycloalkyl, $R^{1C}$-substituted or unsubstituted aryl, or $R^{1C}$-substituted or unsubstituted heteroaryl. $R^{1C}$ is independently halogen, —CN, —CF$_3$, —CCl$_3$, —OH, —NH$_2$, —SO$_2$, —COOH, oxo, nitro, —SH, —CONH$_2$, unsubstituted alkyl, unsubstituted heteroalkyl, unsubstituted cycloalkyl, unsubstituted heterocycloalkyl, unsubstituted aryl, or unsubstituted heteroaryl.

Further to this embodiment, $R^2$ is $R^{2A}$-substituted or unsubstituted alkyl, $R^{2A}$ substituted or unsubstituted heteroalkyl, $R^{2A}$ substituted or unsubstituted cycloalkyl, $R^{2A}$ substituted or unsubstituted heterocycloalkyl, $R^{2A}$ substituted or unsubstituted aryl, or $R^{2A}$ substituted or unsubstituted heteroaryl. $R^{2A}$ is independently halogen, —CN, —CF$_3$, —CCl$_3$, —OH, —NH$_2$, —SO$_2$, —COOH, oxo, nitro, —SH, —CONH$_2$, $R^{2B}$-substituted or unsubstituted alkyl, $R^{2B}$-substituted or unsubstituted heteroalkyl, $R^{2B}$-substituted or unsubstituted cycloalkyl, $R^{2B}$-substituted or unsubstituted heterocycloalkyl, $R^{2B}$-substituted or unsubstituted aryl, or $R^{2B}$-substituted or unsubstituted heteroaryl. $R^{2B}$ is independently halogen, —CN, —CF$_3$, —CCl$_3$, —OH, —NH$_2$, —SO$_2$, —COOH, oxo, nitro, —SH, —CONH$_2$, $R^{2C}$-substituted or unsubstituted alkyl, $R^{2C}$-substituted or unsubstituted heteroalkyl, $R^{2C}$-substituted or unsubstituted cycloalkyl, $R^{2C}$-substituted or unsubstituted heterocycloalkyl, $R^{2C}$-substituted or unsubstituted aryl, or $R^{2C}$-substituted or unsubstituted heteroaryl. $R^{2C}$ is independently halogen, —CN, —CF$_3$, —CCl$_3$, —OH, —NH$_2$, —SO$_2$, —COOH, oxo, nitro, —SH, —CONH$_2$, unsubstituted alkyl, unsubstituted heteroalkyl, unsubstituted cycloalkyl, unsubstituted heterocycloalkyl, unsubstituted aryl, or unsubstituted heteroaryl.

Further to this embodiment, $R^3$ is hydrogen, or $R^{3A}$-substituted or unsubstituted alkyl. $R^{3A}$ is independently halogen, —CN, —CF$_3$, —CCl$_3$, —OH, —NH$_2$, —SO$_2$, —COOH, oxo, nitro, —SH, —CONH$_2$, unsubstituted alkyl, unsubstituted heteroalkyl, unsubstituted cycloalkyl, unsubstituted heterocycloalkyl, unsubstituted aryl, or unsubstituted heteroaryl.

Further to this embodiment, $R^4$ is independently halogen, —CN, —SH, —OH, —COOH, —NH$_2$, —CONH$_2$, nitro, —CF$_3$, —CCl$_3$, $R^{4A}$-substituted or unsubstituted alkyl, $R^{4A}$-substituted or unsubstituted heteroalkyl, $R^{4A}$ substituted or unsubstituted cycloalkyl, $R^{4A}$-substituted or unsubstituted heterocycloalkyl, $R^{4A}$ substituted or unsubstituted aryl, or $R^{4A}$-substituted or unsubstituted heteroaryl. $R^{4A}$ is independently halogen, —CN, —CF$_3$, —CCl$_3$, —OH, —NH$_2$, —SO$_2$, —COOH, oxo, nitro, —SH, —CONH$_2$, $R^{4B}$-substituted or unsubstituted alkyl, $R^{4B}$-substituted or unsubstituted heteroalkyl, $R^{4B}$-substituted or unsubstituted cycloalkyl, $R^{4B}$-substituted or unsubstituted heterocycloalkyl, $R^{4B}$-substituted or unsubstituted aryl, or $R^{4B}$-substituted or unsubstituted heteroaryl. $R^{4B}$ is independently halogen, —CN, —CF$_3$, —CCl$_3$, —OH, —NH$_2$, —SO$_2$, —COOH, oxo, nitro, —SH, —CONH$_2$, $R^{4C}$-substituted or unsubstituted alkyl, $R^{4C}$-substituted or unsubstituted heteroalkyl, $R^{4C}$-substituted or unsubstituted cycloalkyl, $R^{4C}$-substituted or unsubstituted heterocycloalkyl, $R^{4C}$-substituted or unsubstituted aryl, or $R^{4C}$-substituted or unsubstituted heteroaryl. $R^{4C}$ is independently halogen, —CN, —CF$_3$, —CCl$_3$, —OH, —NH$_2$, —SO$_2$, —COOH, oxo, nitro, —SH, —CONH$_2$, unsubstituted alkyl, unsubstituted heteroalkyl, unsubstituted cycloalkyl, unsubstituted heterocycloalkyl, unsubstituted aryl, or unsubstituted heteroaryl.

In another aspect, there is provided a compound of Formula (I) as disclosed above, provided, however, that: (i) the compound of Formula (I) is not

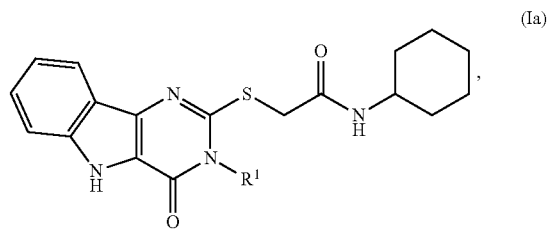

(Ia)

wherein $R^1$ is p-fluorophenyl or p-methylphenyl; or (ii) the compound is not

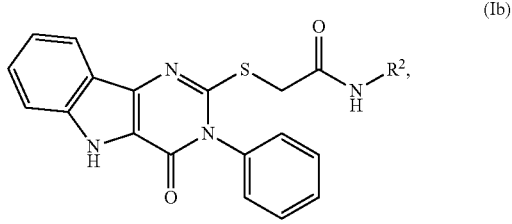

(Ib)

wherein $R^2$ is unsubstituted aryl, unsubstituted cyclohexyl, unsubstituted thiazole, or —CH$_2$-furanyl; or (iii) $R^3$ is not hydrogen.

Further to any aspect disclosed above, in one embodiment, $R^1$ is not substituted phenyl. In one embodiment, $R^1$ is not p-fluorophenyl or p-methylphenyl.

In one embodiment, the compound does not have the structure of Formula (Ia) wherein $R^1$ is substituted phenyl. In one embodiment, the compound does not have the structure of Formula (Ia) wherein $R^1$ is p-fluorophenyl or p-methylphenyl.

Further to any aspect disclosed above, in one embodiment, $R^2$ is not substituted or unsubstituted aryl, unsubstituted cyclohexyl, unsubstituted thiazole, or —CH$_2$-furanyl. In one embodiment, the compound does not have the structure of Formula (Ib) wherein $R^2$ is substituted or unsubstituted aryl, substituted or unsubstituted cyclohexyl, substituted or unsubstituted thiazole, or alkyl substituted with a substituted or unsubstituted furanyl. In one embodiment, $R^2$ is not unsubstituted aryl, unsubstituted cyclohexyl, unsubstituted thiazole, or —CH$_2$-furanyl.

Further to any aspect disclosed above, in one embodiment $R^1$ is substituted or unsubstituted cycloalkyl or substituted or unsubstituted aryl. In one embodiment, $R^1$ is unsubstituted cycloalkyl or unsubstituted aryl.

In one embodiment, $R^1$ is substituted or unsubstituted $C_6$-$C_8$ cycloalkyl or substituted or unsubstituted phenyl. In one embodiment, $R^1$ is substituted or unsubstituted $C_6$ cycloalkyl or substituted or unsubstituted phenyl.

In one embodiment, $R^1$ is $R^{1A}$-substituted or unsubstituted $C_6$ cycloalkyl or $R^{1A}$-substituted or unsubstituted phenyl, wherein $R^{1A}$ is a halogen. In one embodiment, $R^1$ is $R^{1A}$-substituted or unsubstituted phenyl, wherein $R^{1A}$ is a halogen. In one embodiment, $R^1$ is $R^{1A}$-substituted or unsubstituted phenyl, wherein $R^{1A}$ is a fluoro. In one embodiment, $R^1$ is unsubstituted phenyl.

Further to any aspect disclosed above, in one embodiment the compound does not have the structure of Formula (Ib) wherein $R^2$ is substituted or unsubstituted aryl, substituted or unsubstituted cyclohexyl, substituted or unsubstituted thiazole, or alkyl substituted with a substituted or unsubstituted furanyl.

In one embodiment, $R^2$ is substituted or unsubstituted $C_4$-$C_{12}$ cycloalkyl, substituted or unsubstituted $C_3$-$C_{12}$ alkyl, substituted or unsubstituted aryl, or substituted or unsubstituted heteroaryl. In one embodiment, $R^2$ is substituted or unsubstituted $C_4$-$C_{12}$ cycloalkyl, substituted or unsubstituted $C_4$-$C_{12}$ alkyl, substituted or unsubstituted aryl, or substituted or unsubstituted heteroaryl. In one embodiment, $R^2$ is substituted or unsubstituted $C_4$-$C_{12}$ cycloalkyl, substituted or unsubstituted $C_4$-$C_{12}$ branched alkyl, or substituted or unsubstituted phenyl. In one embodiment, $R^2$ is $R^{2A}$-substituted or unsubstituted $C_4$-$C_{12}$ cycloalkyl, $R^{2A}$-substituted or unsubstituted $C_4$-$C_{12}$ branched alkyl, or $R^{2A}$-substituted or unsubstituted phenyl, wherein $R^{2A}$ is halogen. In one embodiment, $R^2$ is $R^{2A}$-substituted or unsubstituted $C_4$-$C_{12}$ cycloalkyl, $R^{2A}$-substituted or unsubstituted $C_4$-$C_{12}$ branched alkyl, or $R^{2A}$-substituted or unsubstituted phenyl, wherein $R^{2A}$ is fluoro. In one embodiment, $R^2$ is unsubstituted $C_4$-$C_{12}$ cycloalkyl, unsubstituted $C_4$-$C_{12}$ branched alkyl, or $R^{2A}$-substituted or unsubstituted phenyl, wherein $R^{2A}$ is fluoro. In one embodiment, $R^2$ is unsubstituted $C_6$-$C_{12}$ cycloalkyl, unsubstituted $C_4$-$C_{12}$ branched alkyl, or unsubstituted phenyl. In one embodiment, $R^2$ is unsubstituted $C_6$-$C_{10}$ cycloalkyl. In one embodiment, $R^2$ is unsubstituted $C_6$-$C_8$ cycloalkyl. In one embodiment, $R^2$ is unsubstituted cyclohexyl.

In one embodiment, $R^3$ is hydrogen or substituted or unsubstituted alkyl. In one embodiment, $R^3$ is hydrogen or unsubstituted alkyl. In one embodiment, $R^3$ is hydrogen or unsubstituted $C_1$-$C_3$ alkyl. In one embodiment, $R^3$ is hydrogen, methyl or ethyl. In one embodiment, $R^3$ is methyl. In one embodiment, $R^3$ is ethyl. In one embodiment, $R^3$ is hydrogen.

In one embodiment, z1 is 0, 1, 2, 3, or 4. In one embodiment, z1 is 0 or 1. In one embodiment, z1 is 0. In one embodiment, z1 is 1. In one embodiment, z2 is 0, 1, 2, 3, 4, or 5. In one embodiment, z2 is 1.

In one embodiment, $R^4$ is independently substituted or unsubstituted alkyl. In one embodiment, $R^4$ independently is substituted alkyl. In one embodiment, $R^4$ is independently unsubstituted alkyl. In one embodiment, $R^4$ is independently substituted or unsubstituted heteroalkyl. In one embodiment, $R^4$ is independently substituted heteroalkyl. In one embodiment, $R^4$ is independently unsubstituted heteroalkyl.

Further to any aspect disclosed above, in one embodiment there is provided a compound with structure of Formula (II):

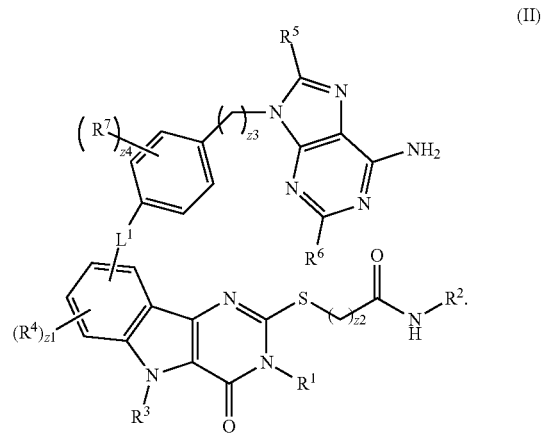

(II)

For Formula (II), $R^1$, $R^2$, $R^3$, $R^4$, z1 and z2 are as disclosed above for Formula (I), including embodiments thereof. The symbol z3 is an integer from 1 to 10. The symbol z4 is an integer from 0 to 4. $L^1$ is substituted or unsubstituted alkylene or substituted or unsubstituted heteroalkylene. $R^5$ is —$SR^{5A}$ or —$OR^{5A}$. $R^{5A}$ is hydrogen, substituted or unsubstituted alkyl, substituted or unsubstituted heteroalkyl, substituted or unsubstituted heterocycloalkyl, substituted or unsubstituted cycloalkyl, substituted or unsubstituted aryl, or substituted or unsubstituted heteroaryl. $R^6$ is hydrogen, halogen, nitro, —OH, —SH, —CN, —COOH, —$CONH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$ is independently halogen, —CN, —SH, —OH, —COOH, —$NH_2$, —$CONH_2$, nitro, —$CF_3$, —$CCl_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In one embodiment, $R^6$ is $R^{6A}$-substituted or unsubstituted alkyl, $R^{6A}$ substituted or unsubstituted heteroalkyl, $R^{6A}$ substituted or unsubstituted cycloalkyl, $R^{6A}$ substituted or unsubstituted heterocycloalkyl, $R^{6A}$ substituted or unsubstituted aryl, or $R^{6A}$ substituted or unsubstituted heteroaryl. $R^{6A}$ is independently halogen, —CN, —$CF_3$, —$CCl_3$, —OH, —$NH_2$, —$SO_2$, —COOH, oxo, nitro, —SH, —$CONH_2$, $R^{6B}$-substituted or unsubstituted alkyl, $R^{6B}$-substituted or unsubstituted heteroalkyl, $R^{6B}$-substituted or unsubstituted cycloalkyl, $R^{6B}$-substituted or unsubstituted heterocycloalkyl, $R^{6B}$-substituted or unsubstituted aryl, or $R^{6B}$-substituted or unsubstituted heteroaryl. $R^{6B}$ is independently halogen, —CN, —$CF_3$, —$CCl_3$, —OH, —$NH_2$, —$SO_2$, —COOH, oxo, nitro, —SH, —$CONH_2$, $R^{6C}$-substituted or unsubstituted alkyl, $R^{6C}$-substituted or unsubstituted heteroalkyl, $R^{6C}$-substituted or unsubstituted cycloalkyl, $R^{6C}$-substituted or unsubstituted heterocycloalkyl, $R^{6C}$-substituted or unsubstituted aryl, or $R^{6C}$-substituted or unsubstituted heteroaryl. $R^{6C}$ is independently halogen, —CN, —$CF_3$, —$CCl_3$, —OH, —$NH_2$, —$SO_2$, —COOH, oxo, nitro, —SH, —$CONH_2$, unsubstituted alkyl, unsubstituted heteroalkyl, unsubstituted cycloalkyl, unsubstituted heterocycloalkyl, unsubstituted aryl, or unsubstituted heteroaryl.

In one embodiment, $R^7$ at each occurrence is independently $R^{7A}$-substituted or unsubstituted alkyl, $R^{7A}$ substituted or unsubstituted heteroalkyl, R$^{7A}$ substituted or unsubstituted cycloalkyl, R$^{7A}$ substituted or unsubstituted heterocycloalkyl, R$^{7A}$ substituted or unsubstituted aryl, or R$^{7A}$ substituted or unsubstituted heteroaryl. R$^{7A}$ is independently halogen, —CN, —CF$_3$, —CCl$_3$, —OH, —NH$_2$, —SO$_2$, —COOH, oxo, nitro, —SH, —CONH$_2$, R$^{7B}$-substituted or unsubstituted alkyl, R$^{7B}$-substituted or unsubstituted heteroalkyl, R$^{7B}$-substituted or unsubstituted cycloalkyl, R$^{7B}$-substituted or unsubstituted heterocycloalkyl, R$^{7B}$-substituted or unsubstituted aryl, or R$^{7B}$-substituted or unsubstituted heteroaryl. R$^{7B}$ is independently halogen, —CN, —CF$_3$, —CCl$_3$, —OH, —NH$_2$, —SO$_2$, —COOH, oxo, nitro, —SH, —CONH$_2$, R$^{7C}$-substituted or unsubstituted alkyl, R$^{7C}$-substituted or unsubstituted heteroalkyl, R$^{7C}$-substituted or unsubstituted cycloalkyl, R$^{7C}$-substituted or unsubstituted heterocycloalkyl, R$^{7C}$-substituted or unsubstituted aryl, or R$^{7C}$-substituted or unsubstituted heteroaryl. R$^{7C}$ is independently halogen, —CN, —CF$_3$, —CCl$_3$, —OH, —NH$_2$, —SO$_2$, —COOH, oxo, nitro, —SH, —CONH$_2$, unsubstituted alkyl, unsubstituted heteroalkyl, unsubstituted cycloalkyl, unsubstituted heterocycloalkyl, unsubstituted aryl, or unsubstituted heteroaryl.

In one embodiment, z3 is an integer from 1 to 3. In one embodiment, z3 is 1. In one embodiment, z4 is 0.

In one embodiment, R$^5$ is —OH. In one embodiment, R$^{5A}$ is hydrogen.

In one embodiment, L$^1$ is R$^{11}$-substituted or unsubstituted alkylene, or R$^{11}$-substituted or unsubstituted heteroalkylene. R$^{11}$ is independently halogen, —CN, —CF$_3$, —CCl$_3$, —OH, —NH$_2$, —SO$_2$, —COOH, oxo, nitro, —SH, —CONH$_2$, unsubstituted alkyl, unsubstituted heteroalkyl, unsubstituted cycloalkyl, unsubstituted heterocycloalkyl, unsubstituted aryl, or unsubstituted heteroaryl. In one embodiment, L$^1$ is R$^{11}$-substituted alkylene. In one embodiment, L1 is unsubstituted alkylene. In one embodiment, L$^1$ is R$^{11}$-substituted heteroalkylene. In one embodiment, L$^1$ is unsubstituted heteroalkylene. In one embodiment, L$^1$ is enzymatically cleavable. The terms "enzymatically cleavable" and the like refer, in the usual and customary sense, to a chemical moiety which can undergo bond scission by the action of an enzyme, e.g., hydrolase, esterase, lipase, peptidase, amidase and the like. Scission can occur at a terminal bond of L$^1$ or a non-terminal bond within L$^1$. Bond scission of L$^1$ can be accompanied by bond rearrangement of the resulting fragments of L$^1$ and bond addition, e.g., addition of water (e.g., under the action of a hydrolase, esterase, lipase, peptidase, amidase and the like). Enzymatic cleavage can occur under physiological conditions, e.g., under the action of a physiological enzyme within an organism. Enzymatic cleavage can occur within a cell, e.g., a biological cell as disclosed herein. Enzymatic cleavage can occur extracellularly, e.g., in the circulatory system of a subject. Enzymatic cleavage can occur under in vitro conditions.

In one embodiment, L$^1$ is —C(O)—X$^1$-L$^{1A}$-X$^2$—C(O)—, wherein X$^1$ and X$^2$ are —O— or —NH—, and L$^{1A}$ is substituted or unsubstituted alkylene or substituted or unsubstituted heteroalkylene. In one embodiment, L$^{1A}$ is -L$^{1B}$-(CH$_2$CH$_2$O)$_n$— wherein n is an integer from 1 to 100, and L$^{1B}$ is unsubstituted C$_1$-C$_{10}$ alkylene. In one embodiment, n is an integer in the range of about 1 to 100, 1 to 90, 1 to 80, 1 to 70, 1 to 60, 1 to 50, 1 to 40, 1 to 30, 1 to 20, or 1 to 10. In one embodiment, n is about 100, 90, 80, 70, 60, 50, 40, 30, 20, 18, 16, 14, 12, 10, or 9, 8, 7, 6, 5, 4, 3, or 2. In one embodiment, n is an integer in the range of about 1 to 100, 1 to 90, 1 to 80, 1 to 70, 1 to 60, 1 to 50, 1 to 40, 1 to 30, 1 to 20, or 1 to 10, and L$^{1B}$ is ethylene. In one embodiment, n is an integer from 1 to 10, and L$^{1B}$ is ethylene. In one embodiment, L$^1$ is —C(O)O—CH$_2$CH$_2$—(OCH$_2$CH$_2$)$_n$—NH—C(O)—, wherein n is 1 to 10, e.g., 1, 2, 3, 4, 5, 6, 7, 8, 9, or 10.

In another aspect, there is provided a compound with structure of Formula (III):

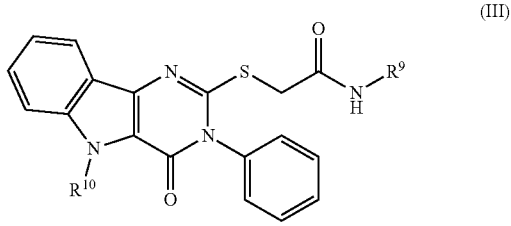

(III)

For Formula (III), R$^9$ is substituted or unsubstituted alkyl, or substituted or unsubstituted cycloalkyl; and R$^{10}$ is substituted or unsubstituted alkyl. In one embodiment, R$^9$ is unsubstituted cycloalkyl, preferably cyclohexyl, cycloheptyl or cyclooctyl. In one embodiment, R$^9$ is unsubstituted alkyl, preferably 3,3-dimethylbutyl. In one embodiment, R$^{10}$ is unsubstituted alkyl. In one embodiment, R$^{10}$ is an alkyl ester.

In another aspect, there is provided a compound with structure of Formula (IV):

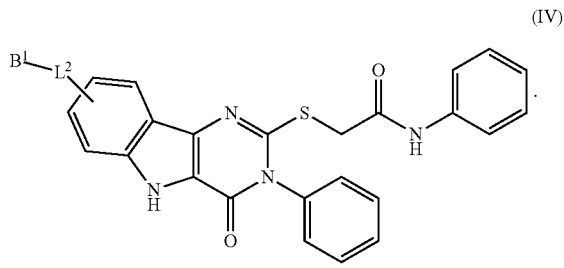

(IV)

For Formula (IV), L$^2$ is a linker, and B$^1$ is a purine base or analog thereof.

In one embodiment, L$^2$ is a substituted or unsubstituted alkylene, or a substituted or unsubstituted heteroalkylene. In one embodiment, L$^2$ includes a water soluble polymer. A "water soluble polymer" means a polymer which is sufficiently soluble in water under physiologic conditions of e.g., temperature, ionic concentration and the like, as known in the art, to be useful for the methods described herein. An exemplary water soluble polymer is polyethylene glycol. In one embodiment, the water soluble polymer is —(OCH$_2$CH$_2$)$_m$— wherein m is 1 to 100. In one embodiment, L$^2$ includes a cleavage element. A "cleavage element" is a chemical functionality which can undergo cleavage (e.g., hydrolysis) to release the compound of Formula (IV), optionally including remnants of linker L$^2$, and B$^1$, optionally including remnants of linker L$^2$.

A representative schematic synthesis of a compound of Formula (IV) is depicted in Scheme 4 following, wherein element (i) is a modified versatile intermediate TLR4 ligand, element (ii) is a TLR7 ligand with linker, and element (iii) is a TLR4-TLR7 dual ligand conjugate (cleavable linkage shown) with structure of Formula (IV). Methods of conjugation of elements (i) and (ii) are well known in the art to afford the resulting dual ligand conjugate with the structure of Formula (IV).

Scheme 4

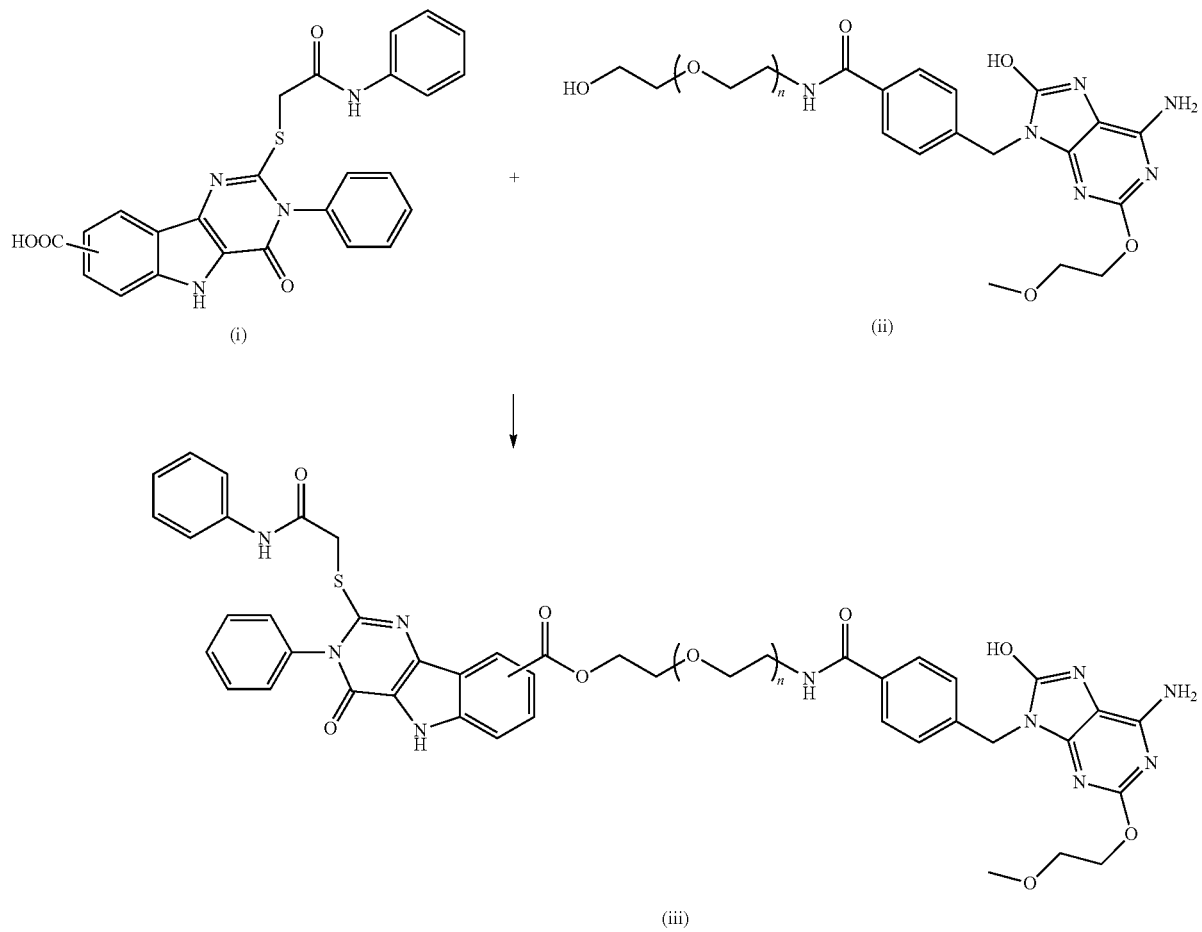

In another aspect, there is provided a compound with structure of Formula (V):

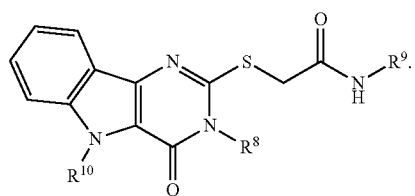

(V)

For Formula (V), $R^9$ and $R^{10}$ are as disclosed for Formula (III). $R^8$ is substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

III. Pharmaceutical Compositions

In another aspect, there is provided a pharmaceutical composition including a pharmaceutically acceptable excipient and a compound having the structure of any one of Formulae (I) to (V) (e.g., Formulae (I) or (II)) as disclosed herein, including embodiments thereof.

The terms "pharmaceutically acceptable" and the like refer, in the usual and customary sense, to a compound or composition which can be administered to a subject without causing a significant adverse toxicological effect, as judged by a medical or veterinary professional.

Accordingly, the terms "pharmaceutically acceptable excipient" and "pharmaceutically acceptable carrier" refer to a substance that aids the administration of an active agent to and absorption by a subject and can be included in the compositions of the present invention without causing a significant adverse toxicological effect on the subject. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and coloring agents, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The pharmaceutical compositions include optical isomers, diastereomers, or pharmaceutically acceptable salts of the compounds disclosed herein. For example, in some embodiments, the pharmaceutical compositions include a compound of the present invention and citrate as a pharmaceutically acceptable salt. The compounds included in the pharmaceutical composition may be covalently attached to a carrier moiety. Alternatively, the compound included in the pharmaceutical composition is not covalently linked to a carrier moiety.

The compounds of the invention can be administered alone or can be coadministered to the subject. Coadministration is meant to include simultaneous or sequential administration of the compounds individually or in combination (more than one compound). The preparations can also be combined, when desired, with other active substances (e.g. to reduce metabolic degradation).

In one embodiment, the pharmaceutical composition includes a compound with structure of Formula (I) as disclosed herein, including embodiments thereof. In one embodiment, the pharmaceutical composition includes a compound with structure of Formula (II) as disclosed herein.

In one embodiment, the pharmaceutical composition further includes an antigen as disclosed below. In one embodiment, the pharmaceutical composition further includes a TLR modulator as disclosed below.

In another aspect, there is provided a pharmaceutical composition including a compound with structure of Formulae (III) or (IV), and a pharmaceutically acceptable excipient.

A. Formulations

The compounds of the present invention can be prepared and administered in a wide variety of oral, parenteral, and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention, i.e., "pharmaceutical formulation."

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds of the invention can also be incorporated into liposomes or administered via transdermal pumps or patches. Pharmaceutical admixtures suitable for use in the present invention include those described, for example, in PHARMACEUTICAL SCIENCES (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.01 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include:

Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

B. Effective Dosages

Pharmaceutical compositions provided by the present invention include compositions wherein the active ingredient is contained in a therapeutically effective amount. The actual amount effective for a particular application will depend, inter alia, on the condition being treated. For example, when administered in methods to treat cancer, such compositions will contain an amount of active ingredient effective to achieve the desired result (e.g. decreasing the number of cancer cells in a subject).

The dosage and frequency (single or multiple doses) of compound administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds of the invention.

For any compound described herein, the therapeutically effective amount can be initially determined from cell culture assays. Target concentrations will be those concentrations of active compound(s) that are capable of eliciting innate immune response as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring effectiveness and adjusting the dosage upwards or downwards, as described above.

Dosages may be varied depending upon the requirements of the patient and the compound being employed. The dose administered to a patient, in the context of the present invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

IV. Vaccines

In another aspect, there is provide a vaccine including an antigen and a compound with structure of any one of Formulae (I) to (V) (e.g., Formulae (I) or (II)) as disclosed herein, including embodiments thereof. The terms "vaccine" and the like as used herein refer, in the usual and customary sense, to a biological preparation that improves immunity to a disease in a subject. A vaccine can contain an agent (e.g., antigen) that resembles a disease-causing microorganism, e.g., a killed or weakened form of the disease-causing microorganism, or a toxin, protein (e.g., surface protein) or other component of a disease-causing microorganism. The term "resembles" in this context means that the agent is sufficiently similar in structure to a disease-causing microorganism (e.g., bacteria, virus), or component thereof, such that the vaccine can improve immunity to a disease in a subject.

As well known in the art, vaccines can include a suspending fluid (e.g., sterile water, saline, or fluids containing protein); excipients (e.g., preservatives and stabilizers), and adjuvants or enhancers (e.g., a compound with structure of Formula (I) including embodiments thereof) that help improve the effectiveness of the vaccine. Vaccines also may contain small amounts of the culture material used to grow the virus or bacteria used in the vaccine, e.g., chicken egg protein and the like.

The terms "vaccine excipient" and the like refer to a pharmaceutically acceptable excipient used in the formulation of vaccines. As known in the art, vaccine excipient and adjuvants include, without limitation: 2-phenoxyethanol, acetone, albumin, alcohol, aluminum hydroxide, aluminum hydroxyphosphate sulfate, aluminum phosphate, aluminum potassium sulfate, aluminum potassium sulfate, amino acid supplement, amino acids, ammonium phosphate, ammonium sulfate, amorphous aluminum hydroxyphosphate sulfate, amphotericin B, anhydrous lactose, arginine, ascorbic acid, asparagine, benzethonium chloride, beta-propiolactone, beta-propiolactone, bovine albumin, bovine calf serum, bovine calf serum, bovine extract, bovine muscle tissue, bovine serum albumin, calcium carbonate, calcium chloride, calf serum, calf serum protein, carbohydrates, casamino acids, casein, castor oil, cell culture media, cellulose acetate phthalate, chick embryo cell culture, chicken protein, chlortetracycline, citric acid, CMRL 1969 medium (supplemented with calf serum), dextran, dextrose, D-fructose, dibasic potassium phosphate, dibasic sodium phosphate, disodium phosphate, D-mannose, Dulbecco's Modified Eagle Medium (DMEM) human serum albumin, Dulbecco's Modified Eagle's Medium, Eagle MEM modified medium, EDTA, egg protein, ethylene diamine tetraacetic acid (EDTA), FD&C Yellow #6 aluminum lake dye, Fenton medium (containing bovine extract), fetal bovine serum, formaldehyde, formalin, Franz complete medium, galactose, gelatin, gentamicin sulfate, glutamate, glutaraldehyde, glycerin, hemin chloride, hexadecyltrimethylammonium bromide, human albumin, human diploid cell cultures, human serum albumin, human-diploid fibroblast cell cultures (WI-38), hydrocortisone, hydrolyzed gelatin, hydrolyzed porcine gelatin, inorganic salts and sugars, insect cell and viral protein, iron ammonium citrate, lactalbumin hydrolysate, lactose, Latham medium derived from bovine casein, L-histidine, lipids, magnesium stearate, magnesium sulfate, mannitol, micro crystalline cellulose, mineral salts, modified Latham medium (derived from bovine casein), modified Mueller and Miller medium, modified Mueller's growth medium, modified Mueller's media (containing bovine extracts), modified Mueller-Miller casamino acid medium (without beef heart infusion), modified Mueller-Miller casamino acid medium without beef heart infusion, modified Stainer-Scholte liquid medium, monkey kidney cells, monobasic potassium phosphate, monobasic sodium phosphate, monosodium glutamate, monosodium L-glutamate, monosodium phosphate, MRC-5 (human diploid) cells, MRC-5 cells, MRC-5 cellular proteins, MRC-5 human diploid cells, Mueller and Miller medium, Mueller Hinton agar, Mueller's Growth Medium, Mueller-Miller casamino acid medium (without beef heart infusion), neomycin, neomycin sulfate, nicotinamide adenine dinucleotide, nonylphenol ethoxylate, octylphenol ethoxylate (Triton™ X-100), ovalbumin, peptone, phenol, phosphate, phosphate buffer, phosphate buffers, phosphate buffers, plasdone C, polacrilin potassium, polydimethylsiloxane, polygeline (processed bovine 14 gelatin), polymyxin, polymyxin B, polymyxin B sulfate, polysorbate 20, polysorbate 80, potassium aluminum sulfate, potassium chloride, potassium glutamate, potassium phosphate, potassium phosphate dibasic, potassium phosphate monobasic, protamine sulfate, recombinant human albumin, residual components of MRC-5 cells including DNA and protein, sodium bicarbonate, sodium borate, sodium citrate, sodium deoxycholate, sodium dihydrogen phosphate dehydrate, sodium hydroxide, sodium metabisulphite, sodium phosphate, sodium phosphate dibasic, sodium phosphate monobasic, sodium phosphate monobasic monohydrate, sodium taurodeoxycholate, sorbitol, soy peptone, Stainer-Scholte liquid medium, Stainer-Scholte medium, Stainer-Scholte medium (modified by the addition of casamino acids and dimethyl-beta-cyclodextrin), streptomycin, succinate buffer, sucrose, thimerosal, Vero (monkey kidney) cells, vitamins, Watson Scherp media, WI-38 human diploid lung fibroblasts, xanthan, yeast, yeast extract, yeast protein, α-tocopheryl hydrogen succinate, and β-propiolactone. In one embodiment, an adjuvant is a compound with structure of Formula (I) as disclosed herein, including embodiments thereof.

In one embodiment, the vaccine includes including an antigen, a compound with structure of any one of Formulae (I) to (V) (e.g., Formulae (I) or (II)) as disclosed herein, including embodiments thereof, and at least one vaccine excipient as disclosed herein. In one embodiment, the vaccine includes including an antigen, a compound with structure of any one of Formulae (I) to (V) (e.g., Formulae (I) or (II)) as disclosed herein, including embodiments thereof, and a plurality of vaccine excipients as disclosed herein.

In one embodiment, the vaccine further includes a TLR modulator.

There are three general categories of Toll-like receptor (TLR) ligands: proteins, nucleic acids and lipid-based elements. See e.g., Kanzler, H., et al., *Nature Med.* 2007, 13:552-559. As known in the art, TLRs recognize conserved structures of microbes and endogenous (host-derived) molecules. TLRs that recognize bacterial and fungal components are localized on the cell surface, whereas TLRs that recognize viral or microbial nucleic acids are localized to intracellular membranes such as endosomes or phagosomes. Thus, different TLRs are amenable to targeting by different types of agents. Cell surface TLRs can be targeted by small molecules (for example, eritoran that inhibits TLR4) and antibodies (for example, OPN-305, which targets TLR2), whereas the intracellular nucleic-acid sensing TLRs is responsive to targeting with modified oligonucleotides. See e.g., Hennessey 2010 (Id.)

Specifically, TLR2 is expressed on monocytes, mature macrophages and dendritic cells, and mast cells. It specifically recognizes components from Gram-positive bacteria, including lipoteichoic acid (LTA) with the assistance of the scavenger receptor CD36. TLR2 can form a heterodimer with either TLR1 to recognize triacylated lipopeptides, such as the synthetic ligand Pam3CSK4, or TLR6 to recognize diacylated lipopeptides like MALP-2. TLR1, TLR2 and TLR6 are highly similar and arose from an evolutionary gene duplication event. See e.g., Hughes, A. L. & Piontkivska, H., *Immunogenetics* 2008, 60:249-256. The dimerization of these TLRs allows the recognition of a more specific and wider array of microbial components. See e.g., Underhill, D., et al., *Nature* 1999, 401:811-815. It is reported that TLR2 and TLR4 are stimulated upon contact with P-MAPA (Protein aggregated Magnesium-Ammonium Phospholinoleate-Palmitoleate Anhydride, as known in the art. See e.g., Favro, W. J., et al., *Infectious Agents and Cancer* 2012, 7:14. Reported TLR2 antagonists include OPN-305 (Arsian F., et al., *Circ. Cardiovasc. Interv.* 2012, 5:279-287) and OPN-401 (Hennessey 2010, Id.)

TLR3 is an endosomal TLR expressed in dendritic cells. It recognizes double stranded RNA, which is produced by replicating viruses and the synthetic ligand polyriboinosinic polyribocytidylic acid (poly I:C). See e.g., Muzio, M., et al., *J. Immunol.* 2000, 164:5998-6004; Zarember, K. A. & Godowski, P. J., *J. Immunol.* 2002, 168:554-561. Reported TLR3 agonists include Rintatolimod (Jasani, B., et al., *Vaccine* 2009, 27:3401-3404).

TLR4 recognizes lipopolysaccharide (LPS) from Gram-negative bacteria. The recognition process is enhanced by LPS-binding protein (LBP), which carries LPS to the CD14 molecule, where it is then presented to the MD-2-TLR4 complex. See e.g., Latz, E., et al., *J. Biol. Chem.* 2002, 277:47834-47843. TLR4 is expressed predominately on monocytes, mature macrophages and dendritic cells, mast cells and the intestinal epithelium. TLR modulators (antagonists) for TLR4 include NI-0101 (Hennessy 2010, Id.), 1A6 (Ungaro, R., et al., *Am. J. Physiol. Gastrointest. Liver Physiol.* 2009, 296:G1167-G1179), AV411 (Ledeboer, A., et al., *Neuron Glia Biol.* 2006, 2:279-291; Ledeboer, A., et al., *Expert Opin. Investig. Drugs* 2007, 16:935-950), Eritoran (Mullarkey, M., et al., *J. Pharmacol. Exp. Ther.* 2003, 305:1093-1102), and TAK-242 (Li, M., et al., *Mol. Pharmacol.* 2006, 69:1288-1295). TLR modulators (agonists) for TLR4 include Pollinex® Quattro (Baldrick, P., et al., *J. Appl. Toxicol.* 2007, 27:399-409; DuBuske, L., et al., *J. Allergy Clin. Immunol.* 2009, 123:S216).

TLR5 binds flagellin, a constituent of bacterial flagella. TLR5 is expressed primarily on cells of the intestinal epithelium and in monocytes, macrophages and dendritic cells. See e.g., Medzhitov, R. & Janeway, G. J., *Trends Microl.* 2000, 8:452-456. Reported TLR5 agonists include VAX-102 (Huleatt, J. W., et al., *Vaccine* 2008, 26:201-214).

TLR7 and TLR8 are found in endosomes of monocytes and macrophages, with TLR7 also being expressed on plasmacytoid dendritic cells, and TLR8 also being expressed in mast cells. Both these receptors recognize single stranded RNA from viruses. Synthetic ligands, such as R-848 and imiquimod, can be used to activate the TLR7 and TLR8 signaling pathways. See e.g., Caron, G., et al., *J. Immunol.* 2005, 175:1551-1557. TLR9 is expressed in endosomes of monocytes, macrophages and plasmacytoid dendritic cells, and acts as a receptor for unmethylated CpG islands found in bacterial and viral DNA. Synthetic oligonucleotides that contain unmethylated CpG motifs are used to activate TLR9. For example, class A oligonucleotides target plasmacytoid dendritic cells and strongly induce IFNα production and antigen presenting cell maturation, while indirectly activating natural killer cells. Class B oligonucleotides target B cells and natural killer cells and induce little interferon-α (IFNα). Class C oligonucleotides target plasmacytoid dendritic cells and are potent inducers of IFNα. This class of oligonucleotides is involved in the activation and maturation of antigen presenting cells, indirectly activates natural killer cells and directly stimulates B cells. See e.g., Vollmer, J., et al., *Eur. J. Immunol.* 2004, 34:251-262; Strandskog, G., et al., *Dev. Comp. Immunol.* 2007, 31:39-51. Reported TLR modulators (agonist) for TLR7 include ANA772 (Kronenberg, B. & Zeuzem, S., *Ann. Hepatol.* 2009, 8:103-112), Imiquimod (Somani, N. & Rivers, J. K., *Skin Therapy Lett.* 2005, 10:1-6), and AZD8848 (Hennessey 2010, Id.) TLR modulators (agonist) for TLR8 include VTX-1463 (Hennessey 2010, Id.) TLR modulators (agonist) for TLR7 and TLR8 include Resiquimod (Mark, K. E., et al., *J. Infect. Dis.* 2007, 195:1324-1331; Pockros, P. J., et al., *J. Hepatol.* 2007, 47:174-182). TLR modulators (antagonists) for TLR7 and TLR9 include IRS-954 (Barrat, F. J., et al., *Eur. J. Immunol.* 2007, 37:3582-3586), and IMO-3100 (Jiang, W., et al., *J. Immunol.* 2009, 182:48.25). TLR9 agonists include SD-101 (Barry, M. & Cooper, C., *Expert Opin. Biol. Ther.* 2007, 7:1731-1737), IMO-2125 (Agrawal, S. & Kandimalla, E. R., *Biochem. Soc. Trans.* 2007, 35:1461-1467), Bio Thrax plus CpG-7909 (Gu, M., et al., *Vaccine* 2007, 25:526-534), AVE0675 (Parkinson, T., *Curr. Opin. Mol. Ther.* 2008, 10:21-31), QAX-935 (Panter, G., et al., *Curr. Opin. Mol Ther.* 2009, 11:133-145), SAR-21609 (Parkinson 2008, Id.), and DIMS0150 (Pastorelli, L., et al., *Expert Opin. Emerg. Drugs* 2009, 14:505-521).

Accordingly, in one embodiment the vaccine further includes a TLR modulator, wherein the TLR modulator is an agonist of TLR2, TLR3, TLR4, TLR5, TLR7, TLR8 or TLR9. In one embodiment, the vaccine further comprises a TLR modulator, wherein the TLR modulator is an antagonist of TLR2, TLR3, TLR4, TLR5, TLR7, TLR8 or TLR9. In one embodiment, the vaccine further includes a TLR modulator selected from TLR modulators for TLR2, TLR3, TLR4, TLR5, TLR7, TLR8 or TLR9. In one embodiment, the vaccine further includes a plurality of TLR modulators selected from TLR modulators for TLR2, TLR3, TLR4, TLR5, TLR7, TLR8 or TLR9.

In one embodiment, the compound with structure of any one of Formulae (I) to (V) (e.g., Formulae (I) or (II)) as disclosed herein, including embodiments thereof, is present in the vaccine in an amount sufficient to synergistically increase the activity of the TLR modulator. The terms "synergistically," "synergy", "synergism," "synergistic" and like refer to a measured effect of compounds administered in combination where the measured effect is greater than the sum of the individual effects of each of the compounds administered alone as a single agent. In one embodiment, the vaccine further includes a TLR modulator, wherein the TLR modulator is an agonist of TLR2, TLR3, TLR4, TLR5, TLR7, TLR8 or TLR9, and the vaccine activity is greater than the sum of the individual effects of each of i) a compound with structure of Formula (I) as disclosed herein, including embodiments thereof, and ii) the TLR modulator, each administered without the other. In one embodiment, the TLR modulator is a TLR2 agonist. In one embodiment, the TLR modulator is a TLR3 agonist. In one embodiment, the TLR modulator is a TLR4 agonist. In one embodiment, the TLR modulator is a TLR5 agonist. In one embodiment, the TLR modulator is a TLR7 agonist. In one embodiment, the TLR modulator is a TLR8 agonist. In one embodiment, the TLR modulator is a TLR9 agonist. In one embodiment, the TLR modulator is a TLR2 antagonist. In one embodiment, the TLR modulator is a TLR3 antagonist. In one embodiment, the TLR modulator is a TLR4 antagonist. In one embodiment, the TLR modulator is a TLR5 antagonist. In one embodiment, the TLR modulator is a TLR7 antagonist. In one embodiment, the TLR modulator is a TLR8 antagonist. In one embodiment, the TLR modulator is a TLR9 antagonist.

V. Biological Cells

In another aspect, there is provided a biological cell which includes a compound with structure of any one of Formulae (I) to (V) (e.g., Formulae (I) or (II)) as disclosed herein, including embodiments thereof. The term "biological cell" and the like refer, in the usual and customary sense, to the basic unit of living organisms, both unicellular and multicellular. The biological cell can be an isolated biological cell removed from the original host organism (e.g., in cell culture, explanted and the like), or a biological cell within the host organism (i.e., not removed from the host organism). In one embodiment, the biological cell is an isolated biological cell. In one embodiment, the biological cell forms part of an organism. In one embodiment, the organism is a human. In one embodiment, the biological cell is a diseased biological cell.

VI. Mixtures

In another aspect, there is provided a mixture including a TLR modulator and a compound with the structure of any one of Formulae (I) to (V) (e.g., Formulae (I) or (II)) as disclosed herein, including embodiments thereof, or pharmaceutically acceptable salt thereof. In one embodiment, the mixture is contained within a single vessel or container. In one embodiment, the mixture is diluted in a liquid (e.g., a liquid pharmaceutically acceptable excipient) for administration to a subject. In one embodiment, the mixture is a pharmaceutical formulation as disclosed herein.

The TLR modulator can be an antagonist or agonist of a TLR. Thus, in one embodiment, the TLR modulator is an antagonist of TLR2, TLR3, TLR4, TLR5, TLR7, TLR8 or TLR9. In one embodiment, the TLR modulator is an agonist of TLR2, TLR3, TLR4, TLR5, TLR7, TLR8 or TLR9.

In one embodiment, the mixture is a liquid mixture or a powder mixture. In one embodiment, the mixture is a liquid pharmaceutically acceptable formulation. In one embodiment, the mixture is a powder pharmaceutically acceptable formulation.

In one embodiment, the compound with structure of Formula (I), including embodiments thereof, is present in the mixture in an amount sufficient to increase the TLR modulator activity in a biological cell. The terms "TLR activity" and the like refer to the biological activity of any of TLR2, TLR3, TLR4, TLR5, TLR7, TLR8 or TLR9. The term "increase the TLR modulator activity" means increasing the antagonist activity of a TLR modulator, or increasing the agonist activity of a TLR modulator, relative to the absence of the compound. Conversely, the term "decrease the TLR modulator activity" means decreasing the antagonist activity of a TLR modulator, or decreasing the agonist activity of a TLR modulator, relative to the absence of the compound. Accordingly, in one embodiment, the compound is present in an amount sufficient to agonize the TLR activity in a biological cell. In one embodiment, the compound is present in an amount sufficient to antagonize the TLR activity in a biological cell.

In one embodiment, the compound with structure of any one of Formulae (I) to (V) (e.g., Formulae (I) or (II)) as disclosed herein, including embodiments thereof, is present in the mixture in an amount sufficient to synergistically increase TLR agonist activity in a biological cell. In one embodiment, the TLR is one of TLR2, TLR3, TLR4, TLR5, TLR7, TLR8 or TLR9. In one embodiment, the TLR modulator is an agonist of TLR7. In one embodiment, the observed increase in immunoglobulin or IFN-γ is greater than the observed sum of the individual effects of i) a compound with structure of Formula (I) and ii) the TLR modulator, when administered alone as single agents. In one embodiment, the TLR modulator is an agonist of the TLR. In one embodiment, the TLR modulator is an agonist of TLR7. See Example 13.

In one embodiment, the mixture agonizes one or more TLRs. In one embodiment, the mixture antagonizes one or more TLRs.

In one embodiment, the biological cell is in an organism (e.g., a human). In one embodiment, the biological cell is in a human. In one embodiment, TLR agonistic activity is increased. In one embodiment, the TLR4 receptor is agonized. In one embodiment, the TLR is agonized, and the innate immune is activated to provide a rapid response to perceived threats before pathogen-specific adaptive immunity can be established. In one embodiment, the TLR is antagonized, and the innate immune response is not activated or is activated at a reduced level compared to the absence of TLR antagonism.

VII. Methods of Modulating TLRs

In another aspect, there is provided a method of modulating a TLR4 protein, including contacting the TLR4 protein with a compound having the structure of any one of Formulae (I) to (V) (e.g., Formulae (I) or (II)) as disclosed herein, including embodiments thereof, or pharmaceutically acceptable salt thereof. In one embodiment, the compound has the structure of Formula (II).

In one embodiment, the activity of the TLR4 protein is increased (i.e., agonized) upon contact with a compound having the structure of any one of Formulae (I) to (V) (e.g., Formulae (I) or (II)) as disclosed herein, including embodiments thereof. In one embodiment, the agonized TLR4 protein activates the innate immune response.

In one embodiment, the activity of the TLR4 protein is decreased (i.e., antagonized) upon contact with a compound having the structure of any one of Formulae (I) to (V) (e.g., Formulae (I) or (II)) as disclosed herein, including embodiments thereof. In one embodiment, the antagonized TLR4 protein fails to activate the innate immune response, or the innate immune response is decreased compared to the absence of TLR4 antagonism.

In embodiments, the modulating occurs in a biological cell. The biological cell may form part of an organism, such as a human. In other embodiments, the modulating occurs in vitro.

VIII. Methods of Modulating Immune Response

In another aspect, there is provided a method of modulating an immune response in a subject in need thereof. The method includes administering to the subject an effective amount of a compound having the structure of any one of Formulae (I) to (V) (e.g., Formulae (I) or (II)) as disclosed herein, including embodiments thereof, or a pharmaceutically acceptable salt thereof.

In one embodiment, the immune response is increased in response to agonism of a TLR (e.g., TLR2, TLR3, TLR4, TLR5, TLR7, TLR8 or TLR9, preferably TLR4). In one embodiment, the immune response is decreased in response to antagonism of a TLR (e.g., TLR2, TLR3, TLR4, TLR5, TLR7, TLR8 or TLR9, preferably TLR4).

In one embodiment, the subject is a cancer patient and the modulating includes increasing an immune response to a cancer cell, relative to the absence of the compound. Thus, in embodiments, a method for treating cancer in a patient in need thereof is provided. The method includes administering to the patient an effective amount (e.g., a therapeutically effective amount) of a compound having the structure of Formula (I), including embodiments thereof.

In one embodiment, the cancer is a cancer of the colorectum, breast, lung, liver, pancreas, lymph nodes, colon, prostate, brain, head and neck, skin, kidney or heart. In one embodiment, the cancer is a hematopoietic neoplastic disorder involving hyperplastic/neoplastic cells of hematopoietic origin (e.g., arising from myeloid, lymphoid or erythroid lineages, or precursors cells thereof). In one embodiment, the cancer arises from poorly differentiated acute leukemias, e.g., erythroblastic leukemia and acute megakaryoblastic leukemia. In one embodiment, the cancer is a myeloid disorder, e.g., acute promyeloid leukemia (APML), acute myelogenous leukemia (AML) and chronic myelogenous leukemia (CML). In one embodiment, the cancer is a lymphoid malignancy, e.g., acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). In one embodiment, the cancer is a malignant lymphoma, e.g., non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. In one embodiment, the cancer is a cell proliferative disorder, e.g., non-endocrine tumor or endocrine tumor. Representative non-endocrine tumors include adenocarcinomas, acinar cell carcinomas, adenosquamous carcinomas, giant cell tumors, intraductal papillary mucinous neoplasms, mucinous cystadenocarcinomas, pancreatoblastomas, serous cystadenomas, solid and pseudopapillary tumors. An endocrine tumor may be an islet cell tumor.

In one embodiment, the subject is an infectious disease patient and the modulating includes increasing an immune response to a pathogen, relative to the absence of the compound. Thus, in embodiments, a method for treating an infectious disease in a patient in need thereof is provided. The method includes administering to the patient an effective amount (e.g., a therapeutically effective amount) of a compound having the structure of Formula (I), including embodiments thereof.

In one embodiment, the infectious disease is a viral disease. In one embodiment, the infectious disease is acquired immunodeficiency syndrome, adenoviridae infections, alphavirus infections, arbovirus infections, Borna disease, bunyaviridae infections, caliciviridae infections, chickenpox, coronaviridae infections, coxsackievirus infections, cytomegalovirus infections, dengue, DNA Virus infections, ecthyma, contagious, encephalitis, arbovirus, Epstein-Barr virus infections, erythema infectiosum, hantavirus infections, hemorrhagic fevers, viral, hepatitis, viral, human, herpes simplex, herpes zoster, herpes zoster oticus, herpesviridae infections, infectious mononucleosis, influenza, e.g., in birds or humans, Lassa fever, measles, Molluscum contagiosum, mumps, paramyxoviridae infections, phlebotomus fever, polyomavirus infections, rabies, respiratory syncytial virus Infections, Rift Valley fever, RNA Virus Infections, rubella, slow virus diseases, smallpox, subacute sclerosing panencephalitis, tumor virus infections, warts, West Nile fever, virus diseases and Yellow Fever.

In one embodiment, the infectious disease is a bacterial infection. In one embodiment, the bacterial infection is a staphylococcal infection, e.g., methicillin-resistance *Staphylococcus aureus* (MRSA). In one embodiment, the infectious disease is anthrax, pertussis, Lyme disease, brucellosis, acute enteritis, community-acquired respiratory infection, nongonococcal urethritis, psittacosis, botulism, pseudomembranous colitis, gas gangrene, tetanus, diphtheria, urinary tract infection associated with *E. coli*, Traveler's diarrhea, hemorrhagic colitis, tularemia, bacterial meningitis, peptic ulcer, Legionnaire's disease, Pontiac fever, leptospirosis, listeriosis, leprosy, tuberculosis, mycoplasma pneumonia, gonorrhea, meningococcal disease, Waterhouse-Friderichsen syndrome, Rocky Mountain spotted fever, salmonellosis, bacillary dysentery, cystitis, otitis media, sinusitis, streptococcal pharyngitis, scarlet fever, rheumatic fever, impetigo, puerperal fever, necrotizing fasciitis, syphilis and cholera.

In one embodiment, the subject is an autoimmune disease patient and the modulating includes decreasing an immune response to an endogenous antigen causing the autoimmune disease, relative to the absence of the compound. Thus, in embodiments, a method for treating an autoimmune disease in a patient in need thereof is provided. The method includes administering to the patient an effective amount (e.g., a therapeutically effective amount) of a compound having the structure of Formula (I), including embodiments thereof. In one embodiment, the autoimmune disease is autoimmune encephalomyelitis, colitis, autoimmune insulin dependent diabetes mellitus (IDDM), Wegener granulomatosis, Takayasu arteritis, autoimmune hemolytic anemia, autoimmune hepatitis, autoimmune inner ear disease, Crohn's disease, inflammatory bowel disease, lupus, or multiple sclerosis.

IX. Methods of Decreasing Inflammation

In another aspect, there is provided a method of decreasing inflammation in a subject in need thereof. The method includes administering to the subject an effective amount of a compound having the structure of any one of Formulae (I) to (V) (e.g., Formulae (I) or (II)) as disclosed herein, including embodiments thereof, or a pharmaceutically acceptable salt thereof.

Thus, in embodiments, a method for treating inflammation in a patient in need thereof is provided. The method includes administering to the patient an effective amount (e.g., a therapeutically effective amount) of a compound having the structure of Formula (I), including embodiments thereof.

In one embodiment, the inflammation is associated with acne vulgaris, asthma, autoimmune diseases and disorders, celiac disease, chronic inflammation, chronic prostatitis, glomerulonephritis, hypersensitivities, inflammatory bowel disease, myopathy (e.g., in combination with systemic sclerosis, dermatomyositis, polymyositis, and/or inclusion body myositis), pelvic inflammatory disease, reperfusion injury, rheumatoid arthritis, sarcoidosis, transplant rejection, vasculitis, interstitial cystitis, atherosclerosis, allergies, leukocyte defects (e.g., Chediak-Higashi syndrome), chronic granulomatous disease, or cancer.

In one embodiment, the subject is a cancer patient. As known in the art, inflammation plays a critical role in the microenvironment of tumors and contributes to proliferation, survival and migration. Balancing these activities, the immune system can suppress cancer. Accordingly, if an activated immune response suppresses cancer, then the inflammation arising from the cancer can be decreased. Accordingly, in one embodiment the subject is a cancer patient, and administration of an effective amount of a compound having the structure of Formula (I) as disclosed herein, or a pharmaceutically acceptable salt thereof, results in an increase in the innate immune response, an increase in the activity of the adaptive immune system, and consequent reduction in tumor size and associated inflammation.

In one embodiment, the disease is pathogen invasion, wherein the innate immune response is activated, and the pathogen is neutralized, thereby reducing inflammation. In one embodiment, the disease is pathogen invasion, wherein the innate immune response is activated, thereby facilitating an adaptive immune response resulting in reduced inflammation. In embodiments, the pathogen is a bacterial pathogen, and the infectious disefase is as disclosed herein. In embodiments, the pathogen is a viral pathogen, and the infectious disease is as disclosed herein.

X. Examples

Abbreviations used herein include the following. AUC, area under the curve; HTS, high throughput screen; TLR, Toll-like receptor; IL, interleukin; TNF, tumor necrosis factor; LPS, lipopolysaccharide; MyD88, myeloid differentiation primary response gene 88; MD-2, myeloid differentiation protein-2; MPLA, monophosphoryl lipid A; PBMC, peripheral blood mononuclear cells; EtOH, ethanol; THF, tetrahydrofuran; TMSCl, trimethylsilyl chloride or chlorotrimethylsilane; DOPE, 1,2-dioleoyl-sn-glycero-3-phosphoethanolamine; DMF, N,N-dimethylformamide; HATU, O-(7-azabenzotriazol-1-yl)-N,N,N$^O$,N$^O$-tetramethyluronium-hexafluorophosphate; DCM, di-chloromethane; MeOH, methanol; TEA, triethylamine; BMDC, bone marrow derived dendritic cells; BMDM, bone marrow derived macrophages; NFκB, nuclear factor κB; MTT, 3-(4,5-dimethylthiazol-2-yl)-2,5-diphenyltetrazolium bromide; ISRE, interferon response element; IFN, interferon; SEAP, secreted embryonic alkaline phosphatase; ELISA, enzyme-linked immunosorbent assay; IP-10, interferon γ-induced protein 10; PRR, pattern-recognition receptors.

As part of the studies disclosed herein on small molecules that can activate TLRs a high through-put screening (HTS) campaign was conducted in which a library of compounds was screened in a human cell-based $NF_\kappa B$ activation assay. Many innate signaling pathways converge on the transcription factor $NF_\kappa B$. Hence it was used in the primary screen as a broad indicator of small molecule agonism of innate immunity. The specific innate receptor for the lead compounds was determined using genetically modified cells and primary mouse and human blood or bone marrow mononuclear cells. There is disclosed herein the discovery and structure-activity relationship (SAR) studies of the pyrimido [5,4-b]indole class of ligands and their characterization as TLR4/MD-2 agonists. See e.g., Chan, M., et al., *J. Med. Chem.* 2013, 56:4206-4223, incorporated herein by reference in its entirety and for all purposes.

Compound Design

High-Throughput Screen (HTS) Study Design.

A library of compounds was acquired which consisted of about 170,000 compounds from eight commercially available sub-libraries that included Bioactives, Diversity, Kinase-targeted compounds, and others. The library was screened in three phases at a commercial HTS screening facility using a cell type that is known to express most of the innate immune receptors of interest. For this purpose we selected the human THP-1 cell line that contains a μ-lactamase reporter gene under the control of the NFκB response element that has been stably integrated into the cells. This reporter uses a dual-fluorophore FRET assay format, as known in the art. All screens were performed in activator mode using lipopolysaccharide (LPS) as a positive control, achieving typical Z' values above 0.75. The three-phase screening process consisted of 1) a pilot screen of about 10,000 compounds selected as representative of the entire primary library; 2) the primary screen of the entire library; and 3) a confirmation screen of about 2,000 hits found in the primary screen. Compounds identified as active in two screens were considered to be confirmed hits. We have recently described the detailed analysis of this HTS process relative to hit selection using cluster enrichment methods[9].

Discovery of Pyrimido[5,4-b]Indoles as Activators of NFκB.

Following the cluster enrichment analysis, 225 compounds were selected for further in vitro biological evaluation involving cytokine induction assays in primary mouse cells and cell lines including mouse splenocytes, mouse bone marrow derived dendritic cells (mBMDC), and mouse bone marrow derived macrophages (mBMDM), as well as in primary human cells including human peripheral blood mononuclear cells (hPBMC). The cytokines selected for assay were those that are known to be important for promoting vaccine adjuvant activity, such as inflammatory cytokines (IL-6, IL-12, etc.) and Type 1 interferon. See e.g., Coffman, R. L., et al., *Immunity* 2010, 33:492-503. These cells were incubated in triplicate, with each of the 225 compounds at a single concentration (1 μM for splenocytes and 5 μM for all other mouse cells and human cells), and the supernatants were tested for the presence of NFκB dependent cytokines, IL-8 or IL-6, released from the human or mouse cells, respectively. Thirty-nine of the 225 compounds stimulated the human and mouse cells to secrete IL-8 or IL-6 above the detectable limit. To further confirm activity, these compounds were repurchased and retested by stimulating hPBMC and mBMDC with titrated doses and assaying for IL-8 and IL-6.

A few structurally diverse library scaffolds were identified in these cytokine assays as having reproducible responses in mouse and human stimulation assays. Among these scaffolds, the pyrimido[5,4-b]indoles emerged as the most potent and diverse class of compounds in the mouse cell assays with clear evidence of SAR. Within this scaffold cluster, the leading hit from the initial primary and secondary screens was a substituted acetamide attached to the pyrimidoindole ring system through a thioether linkage. See FIG. 1. Thus, Cmpd 1 provided a starting point for structure-activity studies.

Figure 3A:
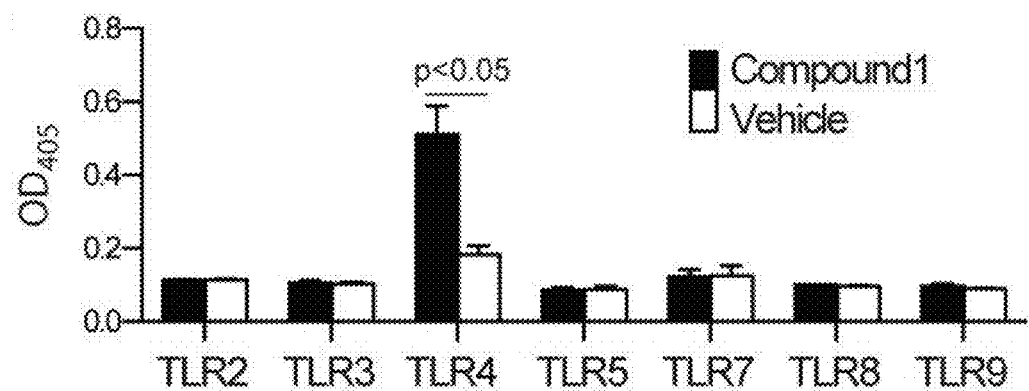
FIGS. 3A-3G depict target identification studies of Cmpd 1 using human TLR HEK293 reporter cell lines and genetically deficient cells.
Figure 3B:
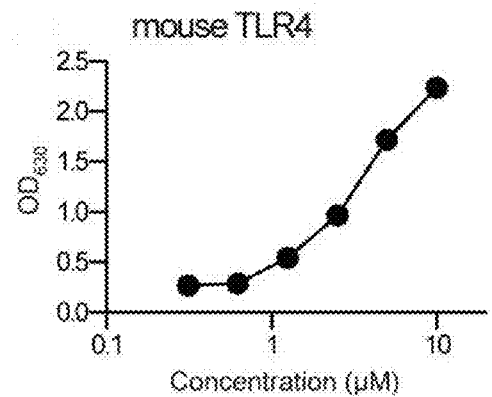
Figure 3C:
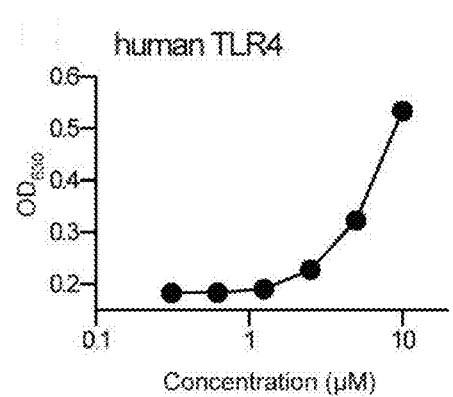

Target Receptor Identification. To identify the target receptor, we used HEK293 cells stably transfected with individual human (h) TLRs: TLR2, TLR3, TLR4/MD-2/CD14, TLR5, TLR7, TLR8, or TLR9 expressing HEK293 cells, along with an NFκB activation reporter producing secreted embryonic alkaline phosphatase (SEAP). Among the tested TLR transfected cells, only those expressing TLR4/MD-2/CD14 responded to pyrimidoindoles, as shown in FIG. 3A for Cmpd 1. Because TLR4/MD-2/CD14 was the receptor complex for the active compounds in this series, it was important to rule out the possibility that activity might have been caused by LPS contamination. Therefore, Cmpd 1 (and all active derivatives) was assayed for LPS (endotoxin) levels using a commercially available detection system and found to contain less than 10 endotoxin units (EU)/μmol compound. To further exclude contamination, Cmpd 1 was resynthesized according to Scheme 1. Both samples of Cmpd 1 displayed indistinguishable physicochemical and biological properties, indicating that the positive biological activity was not due to LPS or another contaminant. Full titration curves of the resynthesized compound were performed using the SEAP assay with mouse and human TLR4 transfected HEK293 cell lines, confirming dose-dependent activation. See FIGS. 3B, 3C.

Figure 3D:
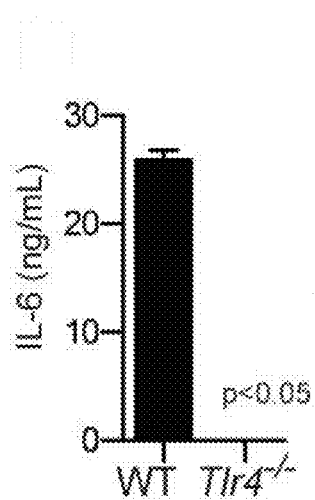
Figure 3E:
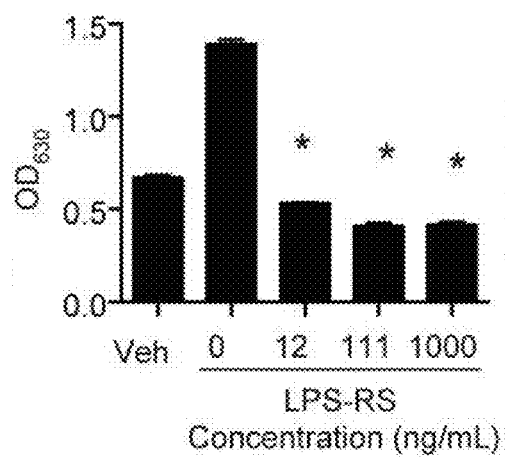

To confirm that TLR4 was indeed the receptor, Cmpd 1 was assayed for IL-6 production in mBMDCs from wild-type and TLR4 deficient mice (FIG. 3D). Genetic disruption of TLR4 completely abrogated IL-6 secretion induced by Cmpd 1. The binding of Cmpd 1 to the TLR4/MD-2/CD14 complex was further confirmed using a competitive antagonist for the TLR4 binding complex, LPSRS (LPS from *Rhodococcus sphaeroides*). See e.g., Coats, S. R., et al., *J. Immunol.* 2005, 175:4490-4498. LPS-RS inhibited the activation by Cmpd 1 in a dose-dependent manner, indicating that Cmpd 1 bound to the TLR4 complex. See FIG. 3E.

Without wishing to be bound by any theory, it is believed that TLR4 signals through two distinct pathways, leading respectively to NFκB dependent cytokines and type I interferon (IFN) production. Several naturally occurring TLR4 ligands and MPLA have been reported to require CD14 to activate the type I IFN regulatory pathway. See e.g., Jiang, Z., et al., *Nature Immunol.* 2005, 6:565-570.

Figure 3F:
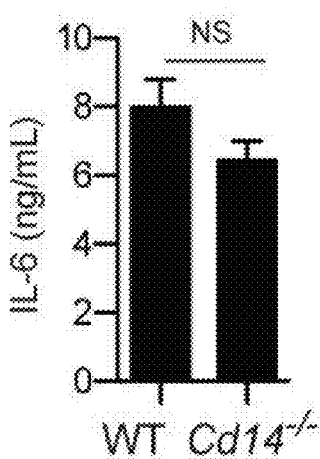
Figure 7A:
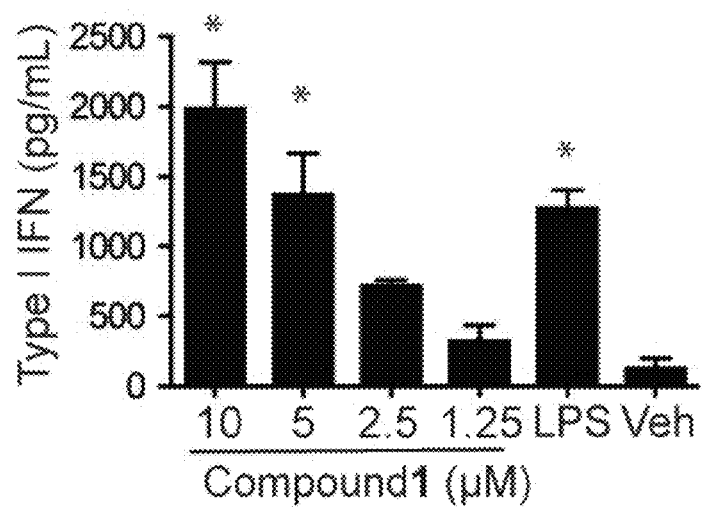
FIGS. 7A-7B depict type I IFN induction by Cmpd 1. Wild type BMDC were incubated with graded concentrations of Cmpd 1 overnight. 0.5% DMSO in saline served as a vehicle controls. The levels type I IFN were determined using L929-ISRE luciferase reporter cell line using murine IFN beta standard (FIG. 7A). IP-10 levels were determined by ELISA (FIG. 7B). Data shown are mean±SEM of triplicates in representative of two independent experiments showing similar results. * denotes p<0.05 was considered as significant compared to vehicle using one way ANOVA with Dunnett's post hoc testing.
Figure 7B:
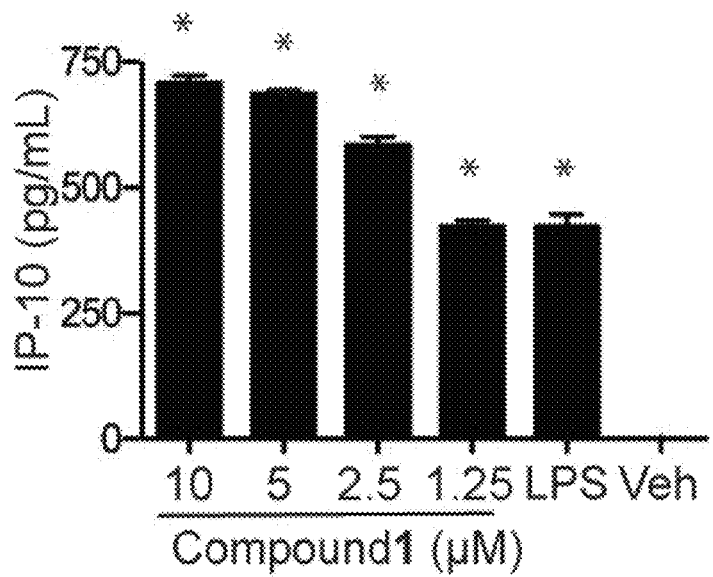

The hTLR4 transfected HEK293 cell line (FIG. 3A) also overexpresses MD-2 and CD14, which are TLR4 accessory proteins. See e.g., Wright, S. D., et al., *Science* 1990, 249:1431-1433; Nagai, Y., et al., *Nature Immunol.* 2002, 3:667-672. Cmpd 1, however, was not dependent on CD14 for either IL-6 or type I IFN production, as demonstrated using CD14 deficient cells. See FIGS. 3F, 3G. The supernatants from mBMDCs stimulated with graded doses of Cmpd 1 were also tested for IP-10 as a surrogate marker of type I IFN release. Results showed a dose-dependent response for type I IFN (FIG. 7A) production, which paralleled that of IP-10 (FIG. 7B).

Figure 4A:
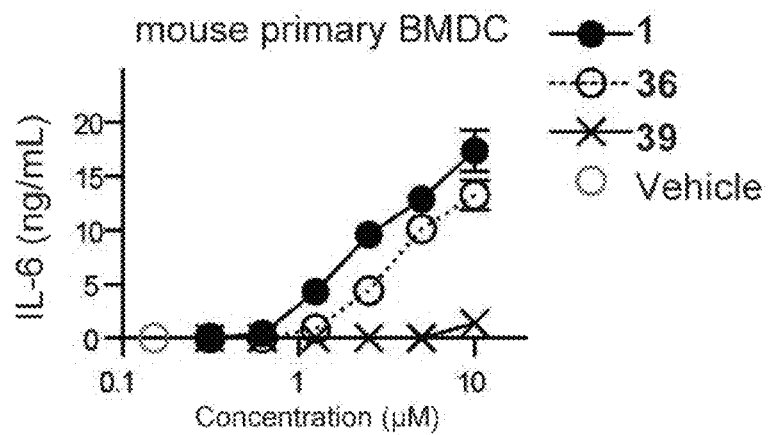
FIGS. 4A-4B depict representative data of SAR compound screening using mouse primary dendritic cells. Biological screening of SAR compounds were evaluated using mouse primary BMDC (mBMDC). The cells were incubated with graded concentrations of indicated Cmpds 1, 36, and 39 (FIG. 4A) or 11 and 12 (FIG. 4B). 0.5% DMSO in saline served as a vehicle control. IL-6 levels in the culture supernatant of BMDC were measured by ELISA. Data shown are mean±SEM of triplicate data in representative of two independent experiments showing similar results. Legend (FIG. 4A): Cmpd 1, solid circle; Cmpd 36 open circle with dotted line; Cmpd 39, X-symbol; vehicle, open circle near origin. Legend (FIG. 4B): Cmpd 1, solid circle; Cmpd 12, open circle with dotted line; Cmpd 11, X-symbol; vehicle, open circle near origin.
Figure 4B:
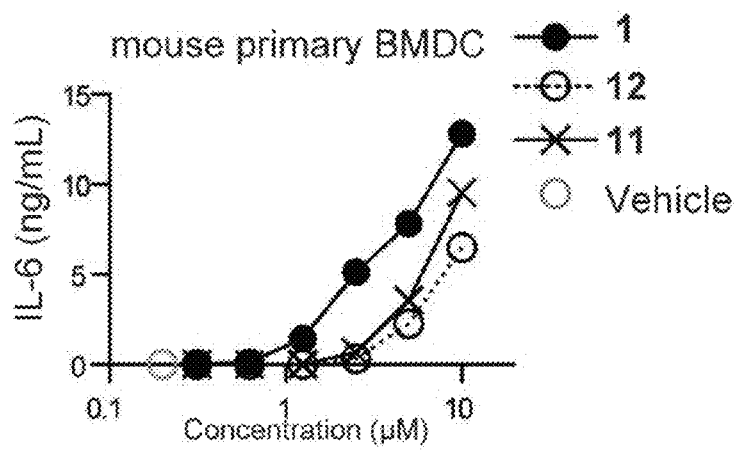
Figure 5A:
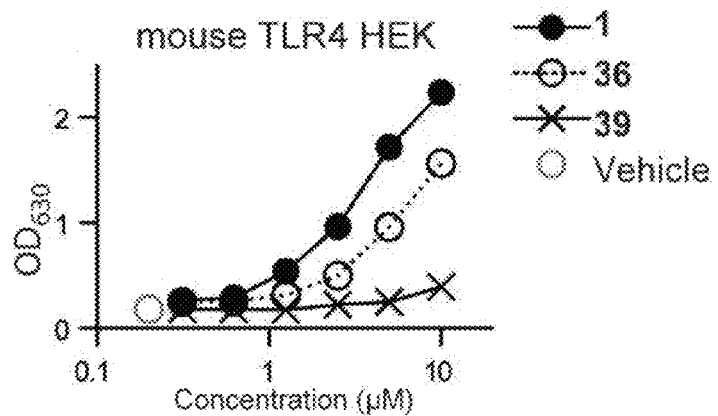
FIGS. 5A-5D depict representative data of SAR compound screening using TLR4 transfectomas. Mouse TLR4 (FIGS. 5A, 5C) and hTLR4 (FIGS. 5B, 5D) HEK transfectomas were incubated with graded concentrations of the indicated compounds 1, 36, and 39 (A) or 11 and 12 (B) for 18 h. DMSO 0.5% served as the vehicle control. The specific activation of the reporter cell lines was measured by SEAP activity in the supernatant by absorption at 630 nm. Data shown are mean±SEM of triplicate data. Legend (FIGS. 5A, 5B): Cmpd 1, closed circle; Cmpd 36, open circle; Cmpd 39, X-symbol; vehicle, open circle near origin. Legend (FIGS. 5C, 5D): Cmpd 1, closed circle; Cmpd 12, open circle; Cmpd 11, X-symbol; vehicle, open circle at left.
Figure 5B:
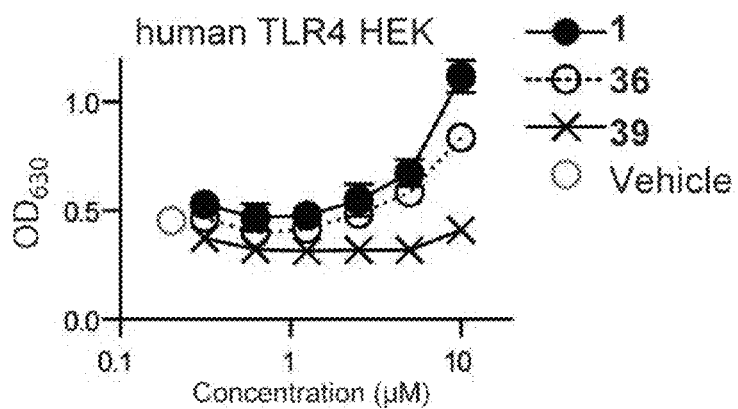
Figure 5C:
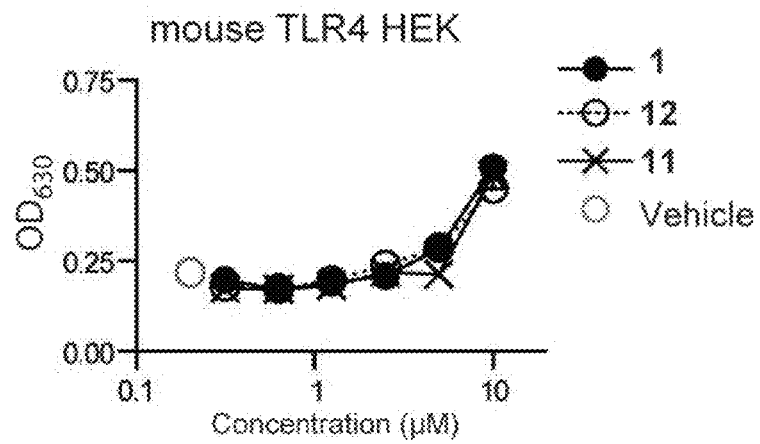
Figure 5D:
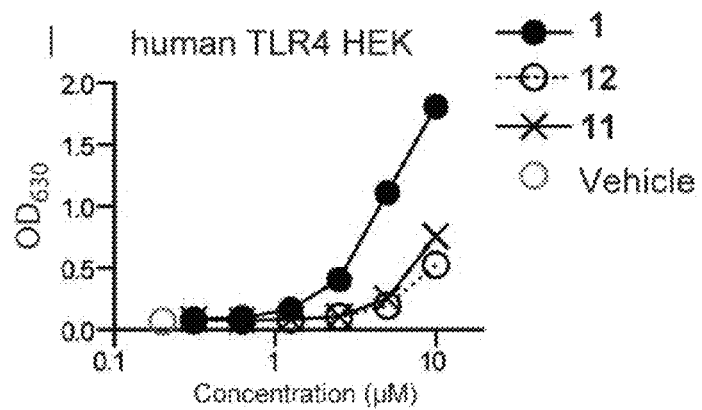

The above assays were utilized to compare the derivatives of the lead pyrimidoindole for their ability to activate mouse and human TLR4. Mouse TLR4 activation was assessed using primary mBMDC and IL-6 release (FIGS. 4A-4B) and confirmed using mTLR4 transfected HEK293 cells (FIGS. 5A, 5C). The values shown in the Tables 1-3 for IL-6 release, and mTLR4 activation are area under the curve (AUC) values for titrated doses of compounds from 312 nM to 10 µM. Each cytokine induction curve was first converted to a percent activity curve, and then the AUC of the percent activity curve was calculated. The process of converting to a percent activity curve allowed subtracting background and adjusting for plate-to-plate variation. Finally, the AUC values were normalized to the activity of Cmpd 1 within each experiment, set at 100. Human TLR4 activation is shown for stimulation of PBMC (IL-8) and hTLR4 HEK293 transfectomas (FIGS. 5B, 5D) at 10 µM, as these assays were not sufficiently sensitive at lower concentrations to make AUC comparisons. The levels of hTLR4 activation by SAR derivatives are expressed relative to Cmpd 1, set at 100.

SAR Studies.

Figure 2:
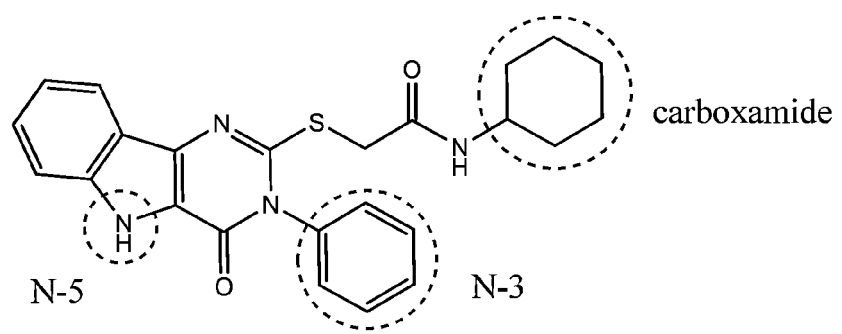
FIG. 2 depicts SAR regions of modification of Cmpd 1.

The primary compound library contained a family of about five hundred compounds in the pyrimido[5,4-b]indole class and therefore represented a valuable initial indication of structural features important for activation of NFκB. Upon inspection of the NFκB activation values relative to these structural features, several trends were apparent. There is a preference for a hydrophobic moiety in the region of the cyclohexyl group of Cmpd 1. In this same region, the carboxamide function is essential. Furthermore, a hydrophobic group at N-3, preferably a phenyl group, is also preferred for activity. All other things being equal in Cmpd 1, substitutions on the N-3 phenyl, other than fluorine atoms, result in loss of activity. Removal of the benzo ring of the indole portion of the scaffold also results in loss of activity. When the C-4 oxo is replaced by NH to form a triazine ring, loss of activity is observed. Finally, exchange of the entire acetamide moiety on the C-2 thiol with the N-3 phenyl group, such that the acetamide is attached at N-3 and the phenyl is attached at the C-2 thiol, results in loss of activity. With these SAR features as an initial guide, we investigated modifications of Cmpd 1 at three regions while maintaining the core pyrimido[5,4-b]indole ring system: the N-substitution of the S-acetamide; the N-3 substituent; and the N-5 substituent. See FIG. 2.

N-substitutions at the carboxamide moiety were first undertaken to probe the limitations of the hydrophobic group requirement at this position with respect to optimization of cytokine induction (Table 1). While keeping all other structural features of hit Cmpd 1 constant, we prepared a substitutions series of carboxamides substituted with various alkyl, cycloalkyl, aromatic, and heteroaromatic groups. The synthesis began with construction of the appropriately substituted pyrimido[5,4-b]indole ring system as shown in Scheme 1. 2-Amino-benzonitrile (2) reacted with ethyl bromoacetate to yield ethyl 2-((2-cyanophenyl)amino)acetate (3) followed by base catalyzed ring closure to the aminoindole. See e.g., Devani, M. B. et al. *J. Pharm. Sci.* 1976, 65:660-664; Thurkauf, A. & Hutchison, A., U.S. Pat. No. 5,326,868, filed Aug. 12, 1993, issued Jul. 5, 1994. At this point in the synthesis, a variety of substituents, represented by $R^1$ in the scheme, may be introduced that will determine the respective N-3 substituent following annulation of the pyrimidine ring. Thus, reaction of Cmpd 4 with an isothiocyanate, such as phenylisothiocyanate, provided the substituted thioureidoindole (Devani, M. B. et al., *J. Pharm. Sci.* 1976, 65:660-664; Monge, A. et al., *An. Quim., Ser. C: Quim. Org. Bioquim.* 1985, 81:267-270), where $R^1$ was phenyl in this example. Ring closure of 5 using polyphosphoric acid yielded the pyrimido[5,4-b]indole (6) bearing the N-3 substituent $R^1$. Alkylation of the 2-thioxo function with chloroacetic acid provided the versatile intermediate 7, which was then used to prepare the final test compounds (8) bearing a variety of N-substitutions at the acetamide moiety, designated as $R^2$ in Scheme 1. Compounds 1, 13, 14, 15, 16, 17, as well as the N-3 derivatives 37 and 38, discussed below, were registered with Chemical Abstracts Service, but no literature references were found for any of these compounds. Cmpd 1 was resynthesized according to Scheme 1, as discussed above. Thus, by this synthetic method, compounds shown in Table 1, with $R^1$ held constant as a phenyl group, were prepared and evaluated in a cytokine induction assay for IL-6 in mBMDC and compared to Cmpd 1. Examples of the data obtained from typical cytokine induction assays and NFκB activation assays are shown in FIGS. 4A-4B and 5A-5D, wherein compounds 1, 11, 12, 36, and 39 are compared for IL-6 production by mBMDC and hPBMC.

Conditions for Scheme 1: Reagents and conditions: (a) BrCH$_2$COOEt, EtOH, reflux; (b) tert-BuOK, THF, <30° C.; (c) $R^1$—NCS, EtOH, reflux; (d) PPA, room temp; (e) ClCH$_2$COOH, KOH/EtOH, reflux; (f) $R^2$—NH, HATU, DMF, room temp.

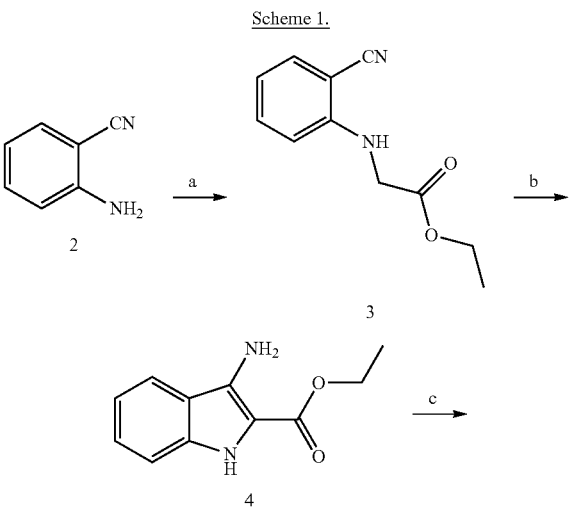

Scheme 1.

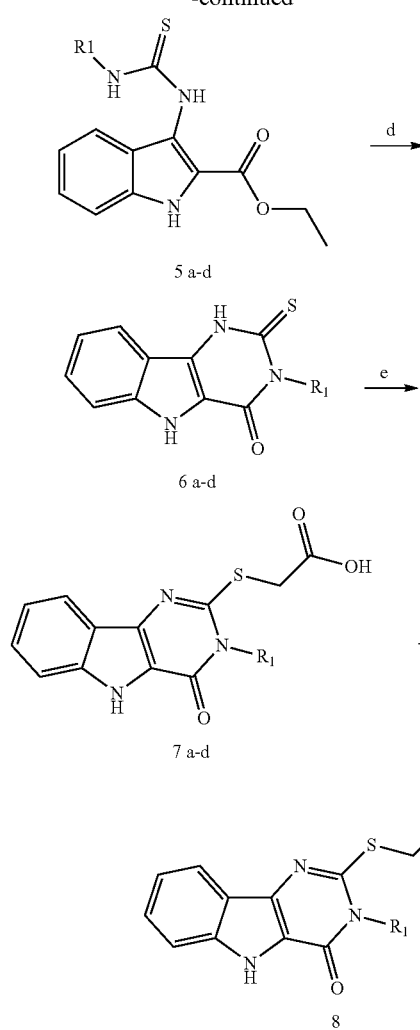

series a; R₁ = phenyl
b; R₁ = cyclohexyl
c; R₁ = 2-naphthyl
d; R₁ = phenethyl

TABLE 1

N-substituted carboxamide derivatives

| Compound | R² | mouse IL-6$^a$ | IP-10$^b$ | TLR4$^a$ | human IL-8$^c$ | TLR4$^c$ |
|---|---|---|---|---|---|---|
| 1 | cyclohexyl* | 100 | 100 | 100 | 100 | 100 |

TABLE 1-continued

N-substituted carboxamide derivatives

| Compound | R² | mouse IL-6$^a$ | IP-10$^b$ | TLR4$^a$ | human IL-8$^c$ | TLR4$^c$ |
|---|---|---|---|---|---|---|
| 9 | cycloheptyl* | 126 | 107 | 99 | 118 | 100 |
| 10 | cyclooctyl* | 114 | 98 | 95 | 73 | 64 |
| 11 | cyclopentyl* | 53 | 52 | 28 | 5 | 23 |
| 12 | cyclobutyl* | 35 | 66 | 18 | 19 | 32 |
| 13 | phenyl* | 11 | 44 | 21 | 15 | 31 |
| 14 | 4-F-phenyl* | 103 | 70 | 81 | 107 | 108 |
| 15 | 2-F-phenyl* | 36 | 54 | 43 | 61 | 71 |
| 16 | 3-F-phenyl* | 14 | 45 | 11 | 13 | 39 |
| 17 | 3-methylphenyl* | 19 | 55 | 13 | 54 | 116 |
| 18 | 2-naphthyl* | <1 | <1 | 2 | <1 | 21 |

TABLE 1-continued

N-substituted carboxamide derivatives

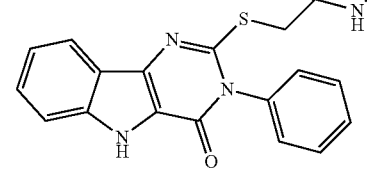

| Compound | R² | mouse IL-6[a] | mouse IP-10[b] | mouse TLR4[a] | human IL-8[c] | human TLR4[c] |
|---|---|---|---|---|---|---|
| 19 | furan-2-ylmethyl | 18 | 26 | 5 | 15 | 27 |
| 20 | 1H-indazol-6-yl | 3 | <1 | <1 | 7 | <1 |
| 21 | thiazol-2-yl | 1 | <1 | 2 | 5 | 12 |
| 22 | ethyl | <1 | <1 | <1 | 4 | 8 |
| 23 | butyl | 49 | 61 | 31 | 29 | 32 |
| 24 | pentyl | 40 | 40 | 42 | 25 | 23 |
| 25 | hexyl | <1 | <1 | 4 | 7 | 8 |
| 26 | iso-butyl | 44 | 53 | 24 | 11 | 21 |
| 27 | isopentyl | 61 | 62 | 56 | 53 | 38 |
| 28 | 3,3-dimethylbutyl | 99 | 85 | 126 | 95 | 72 |
| 29 | 3-methylpentyl | 30 | 45 | 29 | 23 | 17 |
| 30 | sec-butyl | 12 | 55 | 17 | 6 | 13 |
| 31 | pentan-3-yl | 10 | 26 | 8 | <1 | 11 |
| 32 | tert-butyl | <1 | <1 | <1 | 5 | 6 |
| 33 | tetrahydrofuran-2-ylmethyl | 23 | 54 | 21 | 8 | 13 |
| 34 | piperidin-4-yl | <1 | <1 | <1 | 17 | <1 |
| 35 | DOPE | <1 | <1 | <1 | <1 | <1 |

[a]Area under curve (AUC) values normalized to Cmpd 1
[b]All compounds tested at 5 μM, values normalized to Cmpd 1
[c]All compounds tested at 10 μM, values normalized to Cmpd 1

Inspection of the IL-6 AUC values relative to the hydrophobic group R² reveals that in general, compounds bearing the larger cycloalkyl groups, such as cyclooctyl (9), cycloheptyl (10), and cyclohexyl (1), are the most active, followed by branched alkyls, and then straight chain alkyls and aromatic and heteroaromatic groups. A notable exception would be the p-fluorophenyl (14) and o-fluorophenyl (15) compounds. For the R² group, there appears to be a strict "hydrophobic volume" requirement for activity. Hence the 3,3-dimethylbutyl compound (28) is among the most active of the alkyls, with isopentyl (27), butyl (23) and iso-butyl (26) being somewhat less active. Interestingly, when the alkyl chain length of R² is extended to more than 5 carbons or reduced to 3 or fewer carbons, whether branched or not, significant loss of activity is observed.

Encouraged by the SAR trends at the carboxamide moiety, we then addressed the N-3 position. As mentioned above, data from the NFκB primary screen indicated that a hydrophobic group at N-3, preferably an unsubstituted phenyl, is required for activity. However, in order to draw that conclusion with confidence, more examples of compounds bearing similar hydrophobic groups than were represented in the primary compound collection were needed. We therefore elected to prepare and evaluate a few additional derivatives of hit Cmpd 1 with variation only at N-3. Thus, the $R^1$ group in Cmpd 5 was varied by reaction of 4 with the appropriate isothiocyanate and the remaining three steps for each derivative were completed as outlined in Scheme 1, this time maintaining the $R^2$ group as cyclohexyl. Table 2 compares the IL-6 activity of Cmpd 1 with the N-3 derivatives. As the IL-6 data indicates, replacing the N-3 phenyl in Cmpd 1 with a cyclohexyl group (36) causes some loss of activity, while substitution on the N-3 phenyl (37 and 38) results in greater loss of activity. Replacing N-3 phenyl with a larger aromatic, such as naphthyl (39), or extending the phenyl with an alkyl chain, as in phenethyl (40), yields total loss of activity. The combined substitution of $R^1$ with cyclohexyl, and $R^2$ with cyclopentyl (41), results in partial loss of activity.

TABLE 2

N-3 derivatives

| Compound | $R^1$ | mouse IL-6$^a$ | mouse IP-10$^b$ | mouse TLR4$^a$ | human IL-8$^c$ | human TLR4$^c$ |
|---|---|---|---|---|---|---|
| 1 | phenyl | 100 | 100 | 100 | 100 | 100 |
| 36 | cyclohexyl | 71 | 61 | 56 | 27 | 40 |
| 37 | 4-F-phenyl | 48 | 72 | 41 | 5 | 51 |
| 38 | 4-methylphenyl | <1 | <1 | 2 | 6 | 2 |
| 39 | naphthyl | 3 | <1 | 6 | <1 | 3 |
| 40 | phenethyl | <1 | <1 | 1 | 5 | 1 |
| 41 | N-cyclopentyl (cyclohexyl $R^1$) | 47 | 47 | 19 | 14 | 33 |

$^a$Area under curve (AUC) values normalized to Cmpd 1
$^b$All compounds tested at 5 μM, values normalized to Cmpd 1
$^c$All compounds tested at 10μM, values normalized to Cmpd 1

Figure 6A:
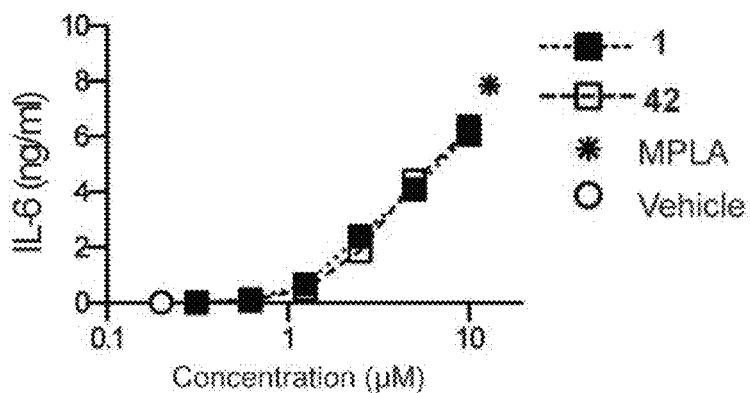
FIGS. 6A-6B depict assessment of cytotoxicity of Cmpds 1 and 42. Cytotoxicity of the compounds was evaluated by MTT assay as a measure of viability. mBMDC (10$^5$/well)
Figure 6B:
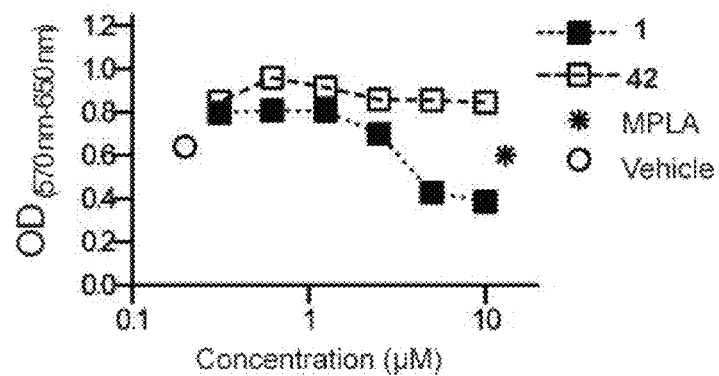

The third area of interest for modification was the N-5 position. None of the compounds in the original HTS library had modifications at this position to guide the SAR. We elected to prepare a few simple N-5 alkyl derivatives of Cmpd 1. The N-5 indole-like nitrogen can be alkylated if the proton is first removed by a strong base, such as sodium hydride. Starting from Cmpd 1, Scheme 2 following shows the preparation of the N-5 methyl derivative (42) that also produced a dimethyl side product (43) wherein the second methylation occurred at the carboxamide function, yielding the N,N-disubstituted derivative. The N-5 methyl butyrate ester (44) of Cmpd 1 was also prepared by this method. Table 3 compares the IL-6 inducing activity of the N-5 derivatives relative to Cmpd 1. Interestingly, simple methylation at N-5 did not abrogate the immune stimulatory activity of Cmpd 1. Moreover, methylation at N-5 decreased the toxicity of Cmpd 1 (FIGS. 6A-6B) as measured by 3-(4,5-dimethylthiazol-2-yl)-2,5-diphenyltetrazolium bromide (MTT) viability assay. Dimethylation, on the other hand, resulted in total loss of IL-6 activity for Cmpd 43. To further probe the N-5 position, we elected to study a few N-5 alkylated derivatives of Cmpd 1 while avoiding dialkylation in the process. Accordingly, we prepared the t-butyl ester of 7a (Cmpd 45) and then alkylated the N-5 position with several primary alkyl halides, as depicted in Scheme 3 following. The resulting t-butyl esters (Cmpds 46a-d) were easily hydrolyzed to the corresponding free carboxylic acids (Cmpds 47a-d) and then converted to the N-cyclohexylcarboxamides (Cmpds 48-51) by the same method as described for Cmpd 1. Thus, using this strategy, the N-5 n-propyl, n-pentyl, n-dodecyl, and cyanomethyl derivatives were prepared. Finally, the cyanomethyl derivative (Cmpd 51) was converted to the N-5 acetamide derivative (Cmpd 52). All N-5 alkyl derivatives were found to be less active than the N-5 methyl (Cmpd 42), with the n-propyl (Cmpd 48) being the next most active of the series. The trend in the toxicity profile for these N-5 alkyl derivatives was confirmed, at least for the shorter chain alkyls, in that the N-5 methyl (Cmpd 42), cyanomethyl (Cmpd 51), and n-propyl (Cmpd 48) derivatives did not reduce cell viability at concentrations up to 10 μM (FIGS. 6A-6B, shown for Cmpd 42, data not shown for Cmpds 48 and 51).

Conditions for Scheme 2: (a) NaH, DMF, room temp, then $CH_3I$; (b) NaH, DMF, then $Br(CH_2)_3COOCH_3$.

Scheme 2. N-5 Derivatives
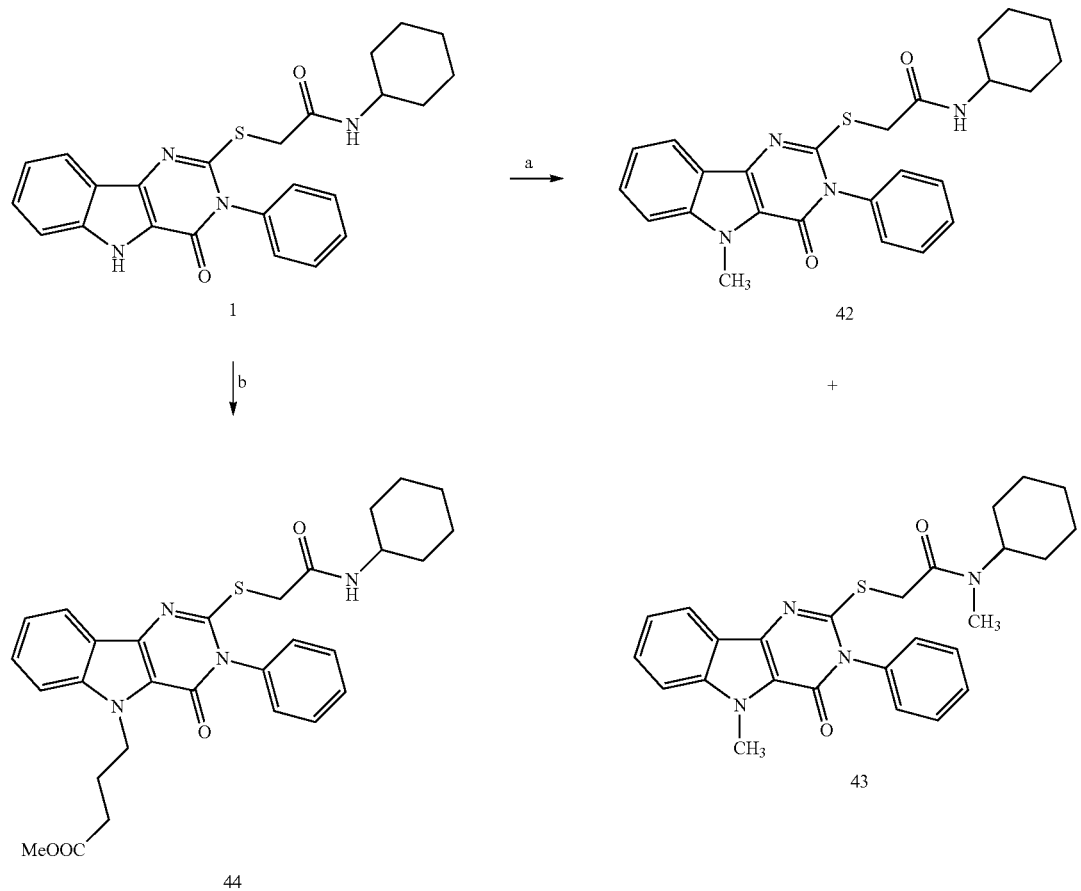
Conditions for Scheme 3: (a) BrCH₂COO t-Bu; (b) NaH, DMF, then R³X; (c) TFA, DCM or CH₃CN; (d) cyclohexyl-NH₂, HATU, DMF, room temp; (e) LiAlH₄, THF; (f) H₂SO₄, H₂O.
Scheme 3. N-5 Alkyl Derivatives
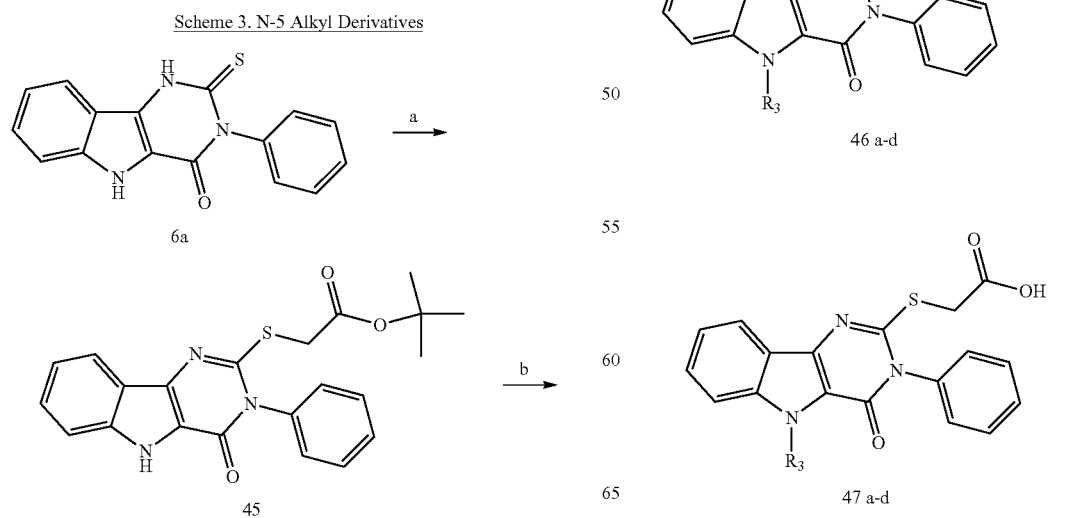

49
-continued

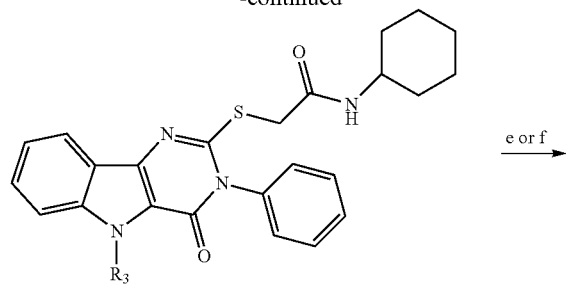

48, R₃ = n-propyl
49, R₃ = n-pentyl
50, R₃ = n-dodecyl
51, R₃ = CH₂CN e or f
→

50
-continued

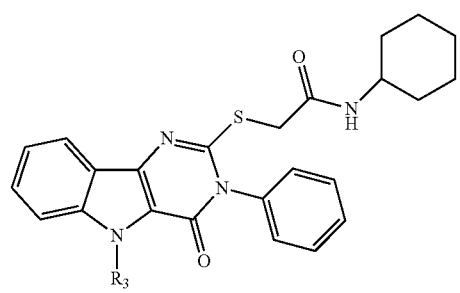

52, R₃ = CH₂CH₂NH₂
53, R₃ = CH₂CONH₂

TABLE 3

N-5 Derivatives

|  |  | mouse | | | human | |
|---|---|---|---|---|---|---|
| Compound | R³ | IL-6[a] | IP-10[b] | TLR4[a] | IL-8[c] | TLR4[c] |
| 1 | H | 100 | 100 | 100 | 100 | 100 |
| 42 | CH₃ | 101 | 99 | 100 | 79 | 92 |
| 43 | CH₃, N-methyl | <1 | <1 | 1 | 5 | <1 |
| 44 | MeO-C(O)-CH₂CH₂CH₂-* | 4 | 19 | 9 | 124 | 19 |
| 48 | n-propyl | 49 | 45 | 43 | 83 | 117 |
| 49 | n-pentyl | 5 | <1 | 6 | 1 | 11 |
| 50 | n-dodecyl | <1 | <1 | 4 | <1 | 10 |
| 51 | N≡C-CH₂-* | 98 | 64 | 55 | 30 | 19 |
| 52 | H₂N-C(O)-CH₂-* | 1 | 1 | 8 | 4 | 11 |

[a] Area under curve (AUC) values normalized to Cmpd 1
[b] All compounds tested at 5 μM, values normalized to Cmpd 1
[c] All compounds tested at 10 μM, values normalized to Cmpd 1

Figure 3G:
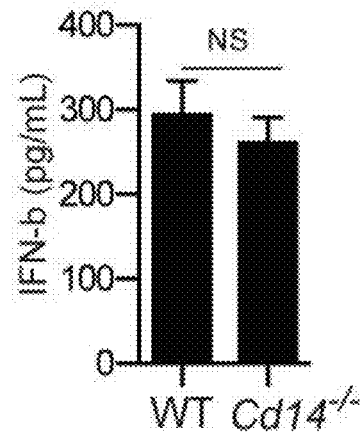

All derivatives prepared for the SAR studies were evaluated in both mouse and human TLR4 HEK reporter assays and results are depicted in Tables 1-3, with values normalized to Cmpd 1, set at 100 in both systems. In the human system, all compounds were tested at 10 micromolar and AUC is not used. It is noted here that these values are not absolute values but are expressed relative to each other within the particular assay system only. Thus, if compared on an absolute basis between both systems, the values obtained for mouse TLR4 transduction would be about ten times greater than those for the human TLR4, indicating that these compounds, in general, are more specific for mouse than for human TLR4 interaction. Furthermore, as one might expect, the IL-6 activity of the compounds correlated well with their respective activities in both TLR4 transfectoma cell lines. That is, with few exceptions, the most active compounds in the IL-6 assays were also those that showed the highest activity in the TLR4 cell lines. One notable exception is observed for Cmpd 44. Cmpd 44 produces very little IL-6 but has good activity in both mouse and human TLR4 reporter cells. The reason for this exception remains unclear, but may be related to the specific binding mode of the compound in the mouse and human TLR4 complex that involves TLR4, MD-2, and CD14. Moreover, it is anticipated that these small molecules bind primarily to the MD-2 protein in the complex essentially in the same manner as that of a portion of the natural ligand LPS. Indeed, follow up studies in mice deficient in CD14 revealed that Cmpd 1 retains IL-6 activity in these mice, suggesting that CD14 is not required for immunoactivity of these small molecules (FIG. 3G).

In addition to the production of inflammatory cytokines (IL-6, IL-12, TNFα, etc.) mediated by NFκB activation, TLR4 signaling can result in the production of type I interferons, a feature that is not only important for activation of dendritic cells leading to good adjuvant activity, but would also be important for rapid defense against a variety of pathogens, particularly viruses. Cmpd 1 was evaluated in graded doses for ability to induce type 1 IFN and IP-10, a surrogate marker for type 1 IFN, in mouse primary cells using a luciferase reporter assay of the resulting supernatants (FIGS. 7A-7B). Results show a dose-dependent response for IFN production (FIG. 7A) and for IP-10 (FIG. 7B). To determine the relative ability of all compounds to induce the production of type 1 IFN, each was evaluated in mouse bone marrow derived dendritic cells as shown in Tables 1-3.

Finally, the activity of each compound in primary human cells was then examined by incubating PBMC from healthy donors with compounds and assaying for IL-8 levels in supernatants by ELISA.

Computational Studies

Without wishing to be bound by any theory, it is believed that TLR4, in association with MD-2, is responsible for the physiological recognition of LPS. See e.g., Shimazu, et al., *J. Exp. Med.* 1999, 189:1777-1782; Medzhitov, R., et al., *Nature* 1997, 388:394-396. The structural basis of receptor specificity and of the mechanism of activation by LPS have recently been elucidated by determining the crystal structure of the TLR4/MD-2-LPS complex at 3.1 A resolution. See e.g., Park, B. S., et al., *Nature* 2009. 458:1191-1195. Binding of agonistic ligands such as LPS causes dimerization of the extracellular domains to form a TLR4/MD-2-LPS macromolecular complex. Like the extracellular domains of other TLRs, TLR4 contains leucine-rich repeats and adopts a characteristic horseshoe-like shape. MD-2 is noncovalently bound to the side of the horseshoe ring and also directly interfaces with the ligand. MD-2 has a β-cup fold structure composed of two antiparallel β-sheets forming a large hydrophobic pocket for ligand binding. LPS binds to this pocket and directly mediates dimerization of the two TLR4/MD-2 complexes. TLR4 can be activated by structurally diverse LPS molecules, which have been predicted to occupy this pocket in MD-2.

Figure 8:
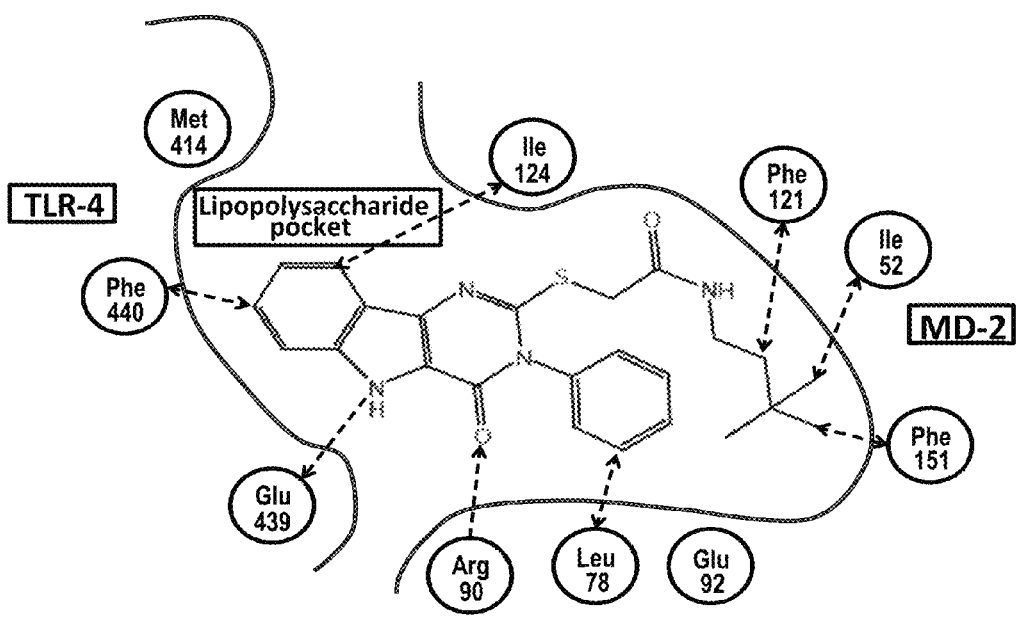
FIG. 8 depicts predicted binding mode of Cmpd 28 to mouse TLR4-MD-2 complex. Sequence legend: (Protein Data Bank entry 2Z64) SEQ ID NOs:1-2. The numbering of SEQ ID NO:1 as described herein is modified by the addition of two residue numbers. For example, Glu439 described herein is residue Glu437 in Protein Data Bank entry 2Z64 (SEQ ID NO:1).
Figure 9:
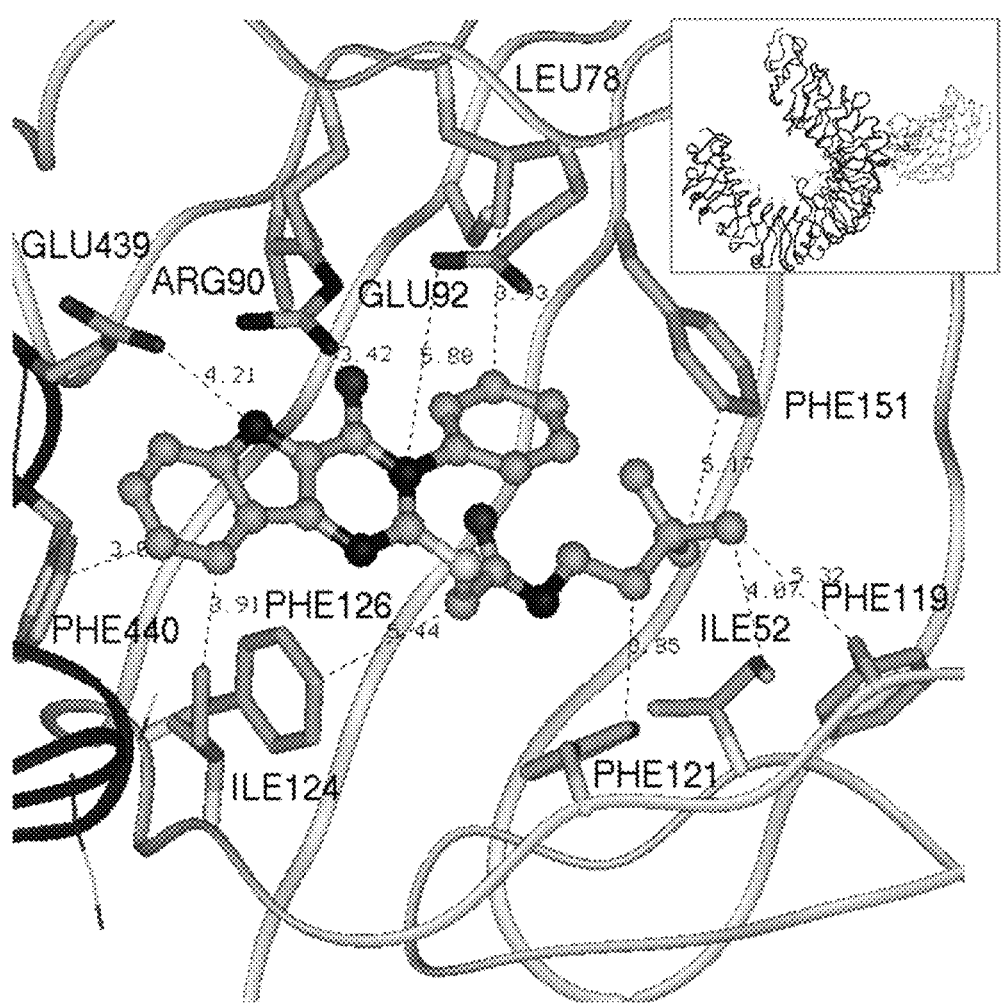
FIG. 9 depicts predicted binding interactions of Cmpd 28 with mouse TLR4-MD-2 complex. Inset: Ribbon diagram of TLR4-MD2 complex.

Small molecule hit compounds discovered in the present study were also thought to bind to the TLR4/MD-2 complex in such a way as to facilitate dimerization. Accordingly, we examined the predicted binding mode(s) of one of the most active compounds to the murine TLR4/MD-2 complex by conducting molecular docking of Cmpd 28 to the crystal structure of the mouse complex (PDB 2Z64, SEQ ID NOs: 1-2) using the programs HEX and AMPAC. See e.g., Macindoe, G., et al., Nucleic Acids Res. 2010, 38:W445-W449; Dewar, M. J. S., *Mod. Tech. Comput. Chem.: MOTECC*-91 1991, 445-467. We selected the best configurations of Cmpd 28 bound to this complex based on molecular surface shape complementarity and the most favorable intermolecular energy of interactions. It is noteworthy that the best docking position for Cmpd 28 was within the LPS pocket. See Park 2009 (Id.) FIG. 8 shows the predicted binding mode of Cmpd 28 in the TLR4/MD-2 model, and the set of binding interactions that may keep the compounds in the MD-2 pocket bound to both TLR2 and MD-2 is depicted in FIG. 9. There is a set of favorable electrostatic interactions resulting in possible hydrogen bonds formed by the residues Glu439 of TLR4 (SEQ ID NO:1) and Arg90 (SEQ ID NO:2) of MD-2 with Cmpd 28, although the former would approach a hydrogen bond interaction due to the flexibility of the Glu439 side chain. There are also multiple potential hydrophobic interactions with MD-2 and TLR4. It is believed that such interactions of the compound with two proteins can improve the free energy of complex formation by approximately 8-10 kcal/mol.

Interestingly, the predicted binding model for the pyrimidoindoles is similar to that proposed for tricyclic antidepressant, amitriptyline. See e.g., Hutchinson, M. R., et al., *Neuroscience* 2010, 168:551-563. This molecule also has some TLR4/MD-2 binding and has a similar three-ring scaffold. Other small molecules such as paclitaxel, opioids, and a peptide have also been reported to bind to the MD-2 binding pocket. See e.g., Zimmer, S. M., et al., *J. Biol. Chem.* 2008, 283:27916-27926; Hutchinson, M. R., et al., *Brain Behav. Immun.* 2009, 24:83-95; Liu, L., et al., *Chem Bio Chem* 2011, 12:1827-1831.

Conclusion.

In the course of an HTS designed to identify activators of innate immunity, a series of substituted pyrimido[5,4-b] indoles were discovered as selective TLR4 ligands. Small molecules of this class are unique among TLR4 activators in that they are "non-lipid-like". Structure-activity evaluation in both mouse and human cells revealed that, to maintain activity, the carboxamide region of this scaffold can contain a hydrophobic moiety of significant "volume". Interestingly, a subset of the compounds bearing phenyl and substituted phenyl carboxamides induced lower NFκB-dependent inflammatory cytokine release while maintaining interferon-dependent IP-10 production. Varying the substituents at N-3 indicated an even greater restriction for a hydrophobic moiety at this position, with a phenyl group being preferred for activity. Finally, N-5 substitution revealed that short alkyl substituents at this position attenuate cell toxicity relative to the corresponding nonsubstituted derivative while maintaining TLR4 activity. Both the inflammatory cytokine and type I IFN inducing activities of these compounds were CD14-independent. Computational studies with one of the active compounds predicted binding primarily to MD-2 in the murine TLR4/MD-2 complex. Lead optimization studies to improve the activity of the compounds using computational methods can be conducted. Here we have described a panel of small molecules that stimulate immune cells to produce distinct profiles of NFκB and interferon associated cytokines Without wishing to be bound by any theory, it is believed that the classes of molecules disclosed herein can allow for differential analysis of the relative pathway induction needed for adequate immunoprotection and immunotherapy for diverse pathogens. Moreover, it is believed that compounds identified by processes disclosed herein (and derivatives thereof) are useful as in a variety of indications, including vaccine adjuvants, anticancer agents, and in the treatment of inflammatory and autoimmune disorders. Other indications include 1) use to improve the effectiveness of vaccines, 2) use as "tolerance inducers" in autoimmune and inflammatory disorders; 3) use as immunotherapeutic agents; and 4) use to stimulate an immune response against cancer.

Chemistry

Materials.

Reagents were purchased as at least reagent grade from Sigma-Aldrich (St. Louis, Mo.) unless otherwise specified and used without further purification. Solvents were purchased from Fischer Scientific (Pittsburgh, Pa.) and were either used as purchased or redistilled with an appropriate drying agent. HTS compound library was obtained from UCSF Small Molecule Discovery Center (San Francisco, Calif.). Cmpds 13, 14, 15, 16, 17, 37, and 38 were purchased from Life Chemicals (Burlington, ON, Canada). All synthesized compounds, intermediates, and purchased compounds from Life Chemicals were determined to be >95% pure by HPLC utilizing an Agilent 1100 LC/MSD. Endotoxin levels of active compounds were measured with The Endosafe®-PTS™ (Charles River, Wilmington, Mass.) and found to have less than 10 EU/μmol. Reaction room temperature was maintained between 22 and 24° C.

Instrumentation.

Analytical TLC was performed using precoated TLC silica gel 60 F254 aluminum sheets purchased from EMD (Gibbstown, N.J.) and visualized using UV light. Flash chromatography was carried out on EMD silica gel 60 (40-63 μm) system or with a Biotage Isolera™ One (Charlotte, N.C.) using the specified solvent. Reactions were monitored using an 1100 LC/MSD (Agilent Technologies, Inc., Santa Clara, Calif.) with either a Supelco Discovery® HS C18 column (Sigma-Aldrich) or an Onyx Monolithic C18 (Phenomenex, Torrance, Calif.) with purity above 98% by percent area. All synthesized compounds and intermediates were analyzed by high resolution MS using an Agilent 6230 ESI-TOFMS (Santa Clara, Calif.). 1H NMR spectra were obtained on a Varian Mercury 300 (Varian, Inc., Palo Alto, Calif.). The chemical shifts are expressed in parts per million (ppm) using suitable deuterated NMR solvents in reference to TMS at 0 ppm. The 3D structures were prepared and optimized using the AMPAC semiempirical quantum chemistry program (Accelrys, San Diego, Calif.).

Example 1

General Procedure A for the Synthesis of Cmpd 5

To a solution of Cmpd 4 (1 eq) in warm EtOH was added the appropriate isothiocyanate (1.1 eq) dropwise with stirring. The reaction was refluxed for 6 h and cooled overnight. Solids were filtered, washed with EtOH, dried overnight in vacuo to give Cmpd5.

Example 2

General Procedure B for the Synthesis of Cmpd 6b-d

Cmpd 5 was dissolved in polyphosphoric acid and stirred at 110° C. for 3.5 h. Solution was added to ice cold water and extracted with EtOAc and dried over $MgSO_4$. The solid was then dried in vacuo overnight to give Cmpd 6.

Example 3

General Procedure C for the Synthesis of Cmpd 7

In a flame dried flask, Cmpd 6a (1 eq) and KOH (2 eq) were dissolved in anhydrous EtOH with heat. In a separate flame dried flask, chloroacetic acid (1 eq) was added to anhydrous EtOH. Chloroacetic acid solution was then added to the reaction mixture and refluxed for 6 h. The reaction was concentrated by half and acidified with 3M HCl to pH 4. The solids were collected, washed with water and dried in vacuo to give Cmpd7.

Example 4

General Procedure D for the Synthesis of Cmpd 8

Cmpd 7 (1 eq), triethylamine (2 eq) and the appropriate amine (1.1 eq) were dissolved in anhydrous DMF. To this solution, HATU (1.1 eq) dissolved in DMF was added and stirred until complete and concentrated in vacuo. The crude material was then recrystallized in MeOH to give Cmpd 8.

Example 5

General Procedure E for the Synthesis of Cmpd 46

NaH (1.1 eq) was added to a solution of Cmpd 45 (1 eq) in DMF. The reaction mixture was stirred for 5 min and then the appropriate alkyl halide (1.1 eq) was added and stirred until complete. The crude product was extracted with EtOAc and dried over $MgSO_4$. Crude material was finally recrystallized with MeOH to give Cmpd 46.

Example 6

General Procedure F for the Synthesis of Cmpd 47

Cmpd 46 was dissolved in 1:1 acetonitrile/trifluoroacetic acid and stirred at room temperature overnight. Depending on alkyl halide, crude material either precipitated as pure product or was purified by chromatography to give Cmpd 47.

Example 7

Synthesis of Specified Compounds

N-cyclohexyl-2-((4-oxo-3-phenyl-4,5-dihydro-3H-pyrimido[5,4-b]indol-2-yl)thio)acetamide (1)

Cmpd 7a (50 mg, 0.14 mmol), triethylamine (40 μL, 0.28 mmol), and cyclohexylamine (18 μL, 0.16 mmol) were dissolved in anhydrous DMF (1 mL). HATU (59.5 mg, 0.16 mmol) dissolved in 0.2 mL of DMF was added to the reaction mixture and stirred for 20 min and then concentrated in vacuo. The crude material was recrystallized with MeOH to give 61 mg in near quantitative yield. $^1$H NMR (300 MHz, DMSO-$d_6$) δ ppm 0.97-1.33 (m, 4H), 1.51 (d, J=8.53 Hz, 1H), 1.56-1.80 (m, 4H), 3.48 (m, 1H), 3.87 (s, 2H), 7.24 (t, J=7.29 Hz, 1H), 7.38-7.67 (m, 6H), 8.05 (d, J=7.98 Hz, 1H), 8.15 (d, J=7.70 Hz, 1H), 12.09 (s, 1H). HRMS calcd for $C^{24}H^{24}N^4O^2SNa$ (M+Na)$^+$, 455.1512. found, 455.1511.

Ethyl 2-((2-cyanophenyl)amino)acetate (3)

Anthranilonitrile (30.29 g, 256 mmol), ethyl bromoacetate (29.46 mL, 267 mmol), and sodium bicarbonate (25.6 g, 300 mmol) were combined in anhydrous EtOH (90 mL) and refluxed for 42 h. After cooling slightly, solution was decanted from precipitate into a prewarmed flask. Further cooling of the decantate yielded crystals, which were then filtered and washed with cold water to give 23.6 g of white crystalline product. $^1$H NMR (500 MHz, DMSO-$d_6$) δ ppm 1.13-1.27 (m, 3H), 4.04 (d, J=6.41 Hz, 2H), 4.12 (q, J=7.22 Hz, 2H), 6.36 (t, J=6.25 Hz, 1H), 6.64 (d, J=8.54 Hz, 1H), 6.69 (t, J=7.47 Hz, 1H), 7.41 (t, J=7.78 Hz, 1H), 7.49 (dd, J=7.93, 1.53 Hz, 1H). HRMS calcd for $C_{11}H_{12}N_2O_2Na$ (M+Na)$^+$, 227.0791. found, 227.0794.

Ethyl 3-amino-1H-indole-2-carboxylate (4)

In a flame-dried flask, a suspension of potassium t-butoxide (7.124 g, 63.5 mmol) in anhydrous THF was stirred and maintained below 30° C. under argon. To this solution was added a solution of Cmpd 3 (16 g, 63.5 mmol) in anhydrous THF over 45 min and stirred for an additional 2 h. The reaction was then poured into ice water, extracted with EtOAc, and dried over MgSO$_4$. The solid was then dissolved in minimal EtOH, and water was added dropwise until just cloudy and allowed to precipitate at room temperature. Precipitate was filtered and washed with cold EtOH to give 6.6 g of Cmpd 4 in 51% yield. $^1$H NMR (500 MHz, DMSO-$d_6$) δ ppm 1.33 (t, J=7.02 Hz, 3H), 4.29 (q, J=7.12 Hz, 2H), 5.68 (s, 2H), 6.88 (ddd, J=8.08, 5.80, 1.98 Hz, 1H), 7.15-7.25 (m, 2H), 7.74 (d, J=7.93 Hz, 1H), 10.34 (s, 1H). HRMS calcd for $C_{11}H_{12}N_2O_2$ (M+H)$^+$, 205.0972. found, 205.0973.

Ethyl 3-(3-phenylthioureido)-1H-indole-2-carboxylate (5a)

Cmpd 4 (5.21 g, 25.5 mmol) was reacted with phenyl isothiocyanate (3.36 mL, 28.1 mmol) in warm EtOH (75 mL) according to general procedure A to give 6.732 g Cmpd 5a in 75% yield. $^1$H NMR (400 MHz, DMSO-$d_6$) δ ppm 1.32 (t, J=7.07 Hz, 3H), 4.32 (q, J=7.31 Hz, 2H), 7.09 (dt, J=14.75, 7.50 Hz, 2H), 7.22-7.38 (m, 3H), 7.43 (d, J=8.29 Hz, 1H), 7.51 (d, J=7.80 Hz, 2H), 7.56 (d, J=8.29 Hz, 1H), 9.40 (s, 1H), 9.69 (br s, 1H), 11.79 (s, 1H). HRMS calcd for $C_{18}H_{17}N_3O_2SNa$ (M+Na)$^+$, 362.0934. found, 362.0935.

Ethyl 3-(3-cyclohexylthioureido)-1H-indole-2-carboxylate (5b)

Cmpd 4 (100 mg, 0.49 mmol) was reacted with cyclohexyl isothiocyanate (169.15 mg, 0.54 mmol) in warm EtOH (750 μL) according to general procedure A to give 104 mg of Cmpd 5b in 61.8% yield. $^1$H NMR (400 MHz, DMSO-$d_6$) δ ppm 1.01-1.42 (m, 9H), 1.49-1.62 (m, 1H), 1.62-1.74 (m, 2H), 1.77-1.96 (m, 2H), 4.13 (br s, 1H), 4.29 (q, J=7.09 Hz, 2H), 7.05 (t, J=7.33 Hz, 1H), 7.25 (t, J=8.07 Hz, 1H), 7.41 (d, J=8.07 Hz, 1H), 7.49 (d, J=8.07 Hz, 1H), 8.91 (s, 1H), 11.71 (br s, 1H). HRMS calcd for $C_{18}H_{23}N_3O_2S$ (M+H)$^+$, 345.1511. found, 345.15142.

Ethyl 3-(3-(naphthalen-1-yl)thioureido)-1H-indole-2-carboxylate (5c)

Cmpd 4 (50 mg, 0.28 mmol) was reacted with 1-naphthyl isothiocyanate (49.9 mg, 0.27 mmol) in warm EtOH (750 μL) according to general procedure A to give 58.6 mg of Cmpd 5c in 61.5% yield. HRMS calcd for $C_{22}H_{19}N_3O_2SNa$ (M+Na)$^+$, 412.1090. found, 412.1091.

Ethyl 3-(3-benzylthioureido)-1H-indole-2-carboxylate (5d)

Cmpd 4 (100 mg, 0.49 mmol) was reacted with phenethyl isothiocyanate (80.4 μL, 0.54 mmol) in warm EtOH (1.5 mL) according to general procedure A to give 147 mg of Cmpd 5d in 81.8% yield. $^1$H NMR (400 MHz, DMSO-$d_6$) δ ppm 1.31 (t, J=6.97 Hz, 3H), 4.27 (q, J=7.21 Hz, 2H), 7.06 (t, J=7.70 Hz, 1H), 7.09-7.33 (m, 7H), 7.43 (dd, J=8.07, 4.03 Hz, 2H), 7.56 (br s, 1H), 9.12 (br s, 1H), 11.79 (br s, 1H). HRMS calcd for $C_{20}H_{22}N_3O2S$ (M+H)$^+$, 368.1427. found, 368.1431.

3-Phenyl-2-thioxo-2,3-dihydro-1H-pyrimido[5,4-b]indol-4(5H)-one (6a)

To a flame-dried flask with cold anhydrous EtOH (75 mL) was added cold acetyl chloride (7 mL, 98.5 mmol) under argon with stirring. In a separate flame-dried flask charged with argon, Cmpd 5a (6.5 g, 19 mmol) was dissolved in anhydrous EtOH (25 mL) and added to the acetyl chloride solution. The reaction was refluxed for 12 h and cooled upon completion. Precipitate was filtered and recrystallized with EtOH to give 3.77 g of Cmpd 6a in 75% yield. $^1$H NMR (400 MHz, DMSO-$d_6$) δ ppm 7.09-7.31 (m, 3H), 7.31-7.61 (m, 6H), 8.20 (d, J=8.07 Hz, 1H), 12.17 (br s, 1H). HRMS calcd for $C_{16}H_{12}N_3OS$ (M+H)$^+$, 294.0696. found, 294.0698.

3-Cyclohexyl-2-thioxo-2,3-dihydro-1H-pyrimido[5,4-b]indol-4(5H)-one (6b)

Cmpd 5b (70 mg, 0.2 mmol) and 1 mL of polyphosphoric acid was reacted according to general procedure B to give 60.6 mg of Cmpd 6b in quantitative yield. $^1$H NMR (400 MHz, DMSO-$d_6$) δ 6 ppm 1.07-1.49 (m, 5H), 1.53-1.70 (m, 1H), 1.70-1.84 (m, 2H), 2.01 (s, 2H), 3.86-4.09 (m, 1H), 7.11 (t, J=8.07 Hz, 1H), 7.29-7.54 (m, 2H), 7.87 (d, J=8.07 Hz, 1H), 8.06 (d, J=6.97 Hz, 1H), 11.60 (s, 1H). HRMS calcd for $C_{16}H_{18}N_3OS$ (M+H)$^+$, 300.1165. found, 300.1169.

3-(Naphthalen-1-yl)-2-thioxo-2,3-dihydro-1H-pyrimido[5,4-b]indol-4(5H)-one (6c)

Cmpd 5c (150 mg, 0.38 mmol) and 1 mL of polyphosphoric acid was reacted according to general procedure B to give 132 mg of Cmpd 6c in quantitative yield. $^1$H NMR (400 MHz, DMSO-$d_6$) δ ppm 7.02-7.18 (m, 1H), 7.33-7.48 (m, 2H), 7.48-7.67 (m, 3H), 7.74 (d, J=8.07 Hz, 1H), 7.87 (d, J=8.07 Hz, 1H), 7.84 (d, J=7.70 Hz, 1H), 7.94-8.03 (m, 1H), 8.03-8.18 (m, 1H), 11.83 (s, 1H). HRMS calcd for C$_{20}$H$_{14}$N$_3$OS (M+H)$^+$, 344.0852. found, 344.0855.

3-Phenethyl-2-thioxo-2,3-dihydro-1H-pyrimido[5,4-b]indol-4(5H)-one (6d)

Cmpd 5d (50.7 mg, 0.138 mmol) and 1 mL of polyphosphoric acid was reacted according to general procedure B. Crude product was purified by automated flash chromatography (Biotage) (DCM/MeOH=99:1) to give 27.1 mg of Cmpd 6d in 61.1% yield. $^1$H NMR (400 MHz, DMSO-d$_6$) δ ppm 2.95 (t, J=7.33 Hz, 2H), 3.67 (t, J=6.20 Hz, 2H), 6.96-7.63 (m, 8H), 7.91 (d, J=7.70 Hz, 1H), 8.31 (d, J=4.77 Hz, 1H), 11.50-11.89 (m, 1H). HRMS calcd for C$_{18}$H$_{15}$N$_3$OS (M+H)$^+$, 321.0936. found, 321.0939.

2-((4-Oxo-3-phenyl-4,5-dihydro-3H-pyrimido[5,4-b]indol-2-yl)thio)acetic acid (7a)

Cmpd 6a (3.77 g, 12.9 mmol), KOH (1.44 g, 25.8 mmol), chloroacetic acid (1.25 g, 12.9 mmol, 6.5 mL of anhydrous EtOH), and 115 mL of anhydrous EtOH were reacted according to general procedure C to give 3.66 g of Cmpd 7a in 81% yield. IR: 3251 (OH), 1702 (CO carboxyl), 1660 (CO amide) cm$^{-1}$. $^1$H NMR (400 MHz, DMSO-d$_6$) δ ppm 3.94 (s, 2H), 7.14-7.36 (m, 1H), 7.38-7.84 (m, 7H), 7.93 (d, J=7.70 Hz, 1H), 12.09 (br s, 1H). HRMS calcd for C$_{18}$H$_{13}$N$_3$O$_3$SNa (M+Na)$^+$, 374.0570. found, 374.0572.

2-((3-cyclohexyl-4-oxo-4,5-dihydro-3H-pyrimido[5,4-b]indol-2-yl)thio)acetic acid (7b)

Cmpd 6b (165.8 mg, 0.55 mmol), KOH (62 mg, 1.1 mmol), chloroacetic acid (52.3 mg, 0.55 mmol, 3 mL of anhydrous EtOH), and 62 mL of anhydrous EtOH were reacted according to general procedure C to give 35.6 mg of Cmpd 7b in 17.9% yield. $^1$H NMR (400 MHz, DMSO-d$_6$) δ ppm 1.05-1.52 (m, 4H), 1.59-2.05 (m, 6H), 3.94 (s, 2H), 4.20-4.46 (m, 1H), 7.15 (t, J=7.33 Hz, 1H), 7.30-7.59 (m, 2H), 7.88 (d, J=8.07 Hz, 1H), 11.79 (br s, 1H). HRMS calcd for C$_{18}$H$_{19}$N$_3$O$_3$SNa (M+Na)$^+$, 380.1039. found, 380.1042.

2-((3-(naphthalen-2-yl)-4-oxo-4,5-dihydro-3H-pyrimido[5,4-b]indol-2-yl)thio)acetic acid (7c)

Cmpd 6c (120 mg, 0.35 mmol), KOH (39.1 mg, 70 mmol), chloroacetic acid (33 mg, 0.35 mmol, 3 mL of anhydrous EtOH), and 62 mL of anhydrous EtOH were reacted according to general procedure C to give 67.1 mg of Cmpd 7c in 47.8% yield. $^1$H NMR (400 MHz, DMSO-d$_6$) δ ppm 3.90 (s, 2H), 7.26 (t, J=7.40 Hz, 1H), 7.33-7.66 (m, 5H), 7.67-7.80 (m, 2H), 7.98 (d, J=7.70 Hz, 1H), 8.09 (d, J=8.43 Hz, 1H), 8.17 (t, J=4.77 Hz, 1H), 12.14 (br s, 1H). HRMS calcd for C$_{22}$H$_{15}$N$_3$O$_3$SNa (M+Na)$^+$, 424.0726. found, 424.0730.

2-((4-Oxo-3-phenethyl-4,5-dihydro-3H-pyrimido[5,4-b]indol-2-yl)thio)acetic acid (7d)

Cmpd 6d (271 mg, 0.84 mmol), KOH (94.5 mg, 1.69 mmol), chloroacetic acid (79.8 mg, 0.84 mmol, 3 mL of anhydrous EtOH), and 62 mL of anhydrous EtOH were reacted according to general procedure C to give 160 mg of Cmpd 7d in 50% yield. $^1$H NMR (400 MHz, DMSO-d$_6$) δ ppm 3.02 (t, J=7.80 Hz, 2H), 4.02 (s, 2H), 4.35 (t, J=7.31 Hz, 2H), 6.87-7.83 (m, 8H), 7.95 (d, J=7.31 Hz, 1H), 11.92 (br s, 1H). HRMS calcd for C$_{20}$H$_{17}$N$_3$O$_3$SNa (M+Na)$^+$, 402.0883. found, 402.0885.

N-Cycloheptyl-2-((4-oxo-3-phenyl-4,5-dihydro-3H-pyrimido[5,4-b]indol-2-yl)thio)acetamide (9)

Cmpd 7a (50 mg, 0.14 mmol), cycloheptylamine (39.86 μL, 0.16 mmol), triethylamine (39.63 μL, 0.28 mmol), and HATU (59.52 mg, 0.16 mmol) were reacted according to general procedure D to give 12.46 mg in 18.5% yield. $^1$H NMR (300 MHz, DMSO-d$_6$) δ ppm 1.18-1.65 (m, 10H), 1.66-1.88 (m, 2H), 3.59-3.77 (m, 1H), 3.87 (s, 2H), 7.25 (t, J=7.01 Hz, 1H), 7.40-7.55 (m, 4H), 7.56-7.68 (m, 3H), 8.06 (d, J=7.98 Hz, 1H), 8.20 (d, J=7.70 Hz, 1H), 12.10 (s, 1H). $^{13}$C NMR (126 MHz, DMSO-d$_6$) δ ppm 24.12, 28.28, 34.69, 37.17, 50.51, 113.31, 119.7, 120.48, 120.78, 120.81, 127.77, 130.00, 130.01, 130.32, 136.51, 137.68, 139.35, 153.01, 155.39, 165.92. HRMS calcd for C$_{25}$H$_{26}$N$_4$O$_2$SNa (M+Na)$^+$, 469.1669. found, 469.1670.

N-cyclooctyl-2-((4-oxo-3-phenyl-4,5-dihydro-3H-pyrimido[5,4-b]indol-2-yl)thio)acetamide (10)

Cmpd 7a (25 mg, 0.07 mmol), cyclooctylamine (24.15 μL, 0.08 mmol), triethylamine (19.82 μL, 0.14 mmol), and HATU (29.76 mg, 0.08 mmol) were reacted according to general procedure D to give 30.77 mg in quantitative yield. $^1$H NMR (400 MHz, DMSO-d$_6$) δ ppm 1.23-1.89 (m, 14H), 3.68-3.82 (m, 1H), 3.87 (s, 2H), 7.24 (t, J=6.97 Hz, 1H), 7.37-7.75 (m, 7H), 8.06 (d, J=8.07 Hz, 1H), 8.18 (d, J=7.70 Hz, 1H), 12.10 (br s, 1H). $^{13}$C NMR (126 MHz, DMSO-d$_6$) δ ppm 23.75, 25.47, 27.25, 31.87, 37.16, 49.49, 113.32, 119.7, 120.48, 120.78, 120.81, 127.78, 130.00, 130.01, 130.32, 136.51, 137.68, 139.36, 153.02, 155.39, 165.90. HRMS calcd for C$_{26}$H$_{29}$N$_4$O$_2$S (M+H)$^+$, 461.2006. found, 461.2010.

N-cyclopentyl-2-((4-oxo-3-phenyl-4,5-dihydro-3H-pyrimido[5,4-b]indol-2-yl)thio)acetamide (11)

Cmpd 7a (50 mg, 0.14 mmol), cyclopentylamine (31 μL, 0.16 mmol), triethylamine (39.63 μL, 0.28 mmol), and HATU (59.52 mg, 0.16 mmol) were reacted according to general procedure D to give 48.9 mg in 76% yield. $^1$H NMR (300 MHz, DMSO-d$_6$) δ ppm 1.32-1.55 (m, 4H), 1.55-1.70 (m, 2H), 1.71-1.86 (m, 2H), 3.87 (s, 2H), 3.97 (dd, J=13.07, 6.46 Hz, 1H), 7.25 (t, J=7.29 Hz, 1H), 7.35-7.72 (m, 7H), 8.05 (d, J=7.98 Hz, 1H), 8.26 (d, J=6.88 Hz, 1H), 12.10 (s, 1H). $^{13}$C NMR (126 MHz, DMSO-d$_6$) δ ppm 23.95, 32.74, 37.13, 51.12, 113.32, 119.69, 120.5, 120.76, 120.79, 127.77, 129.99, 130.01, 130.32, 136.50, 137.67, 139.35, 153.02, 155.39, 166.64. HRMS calcd for C$_{25}$H$_{26}$N$_4$O$_2$SNa (M+Na)$^+$, 441.1356. found, 441.1367.

N-cyclobutyl-2-((4-oxo-3-phenyl-4,5-dihydro-3H-pyrimido[5,4-b]indol-2-yl)thio)acetamide (12)

Cmpd 7a (50 mg, 0.14 mmol), cyclobutylamine (26.73 μL, 0.16 mmol), triethylamine (39.63 μL, 0.28 mmol), and HATU (59.52 mg, 0.16 mmol) were reacted according to general procedure D to give 41.6 mg in 73.5% yield. $^1$H NMR (300 MHz, DMSO-d$_6$) δ ppm 1.48-1.72 (m, 2H), 1.93 (q, J=9.70 Hz, 2H), 2.05-2.26 (m, 2H), 3.85 (s, 2H), 4.08-4.26 (m, 1H), 7.26 (t, J=7.29 Hz, 1H), 7.37-7.70 (m, 6H), 8.07 (d, J=7.98 Hz, 1H), 8.56 (d, J=7.70 Hz, 1H), 12.10 (s, 1H). $^{13}$C NMR (126 MHz, DMSO-d$_6$) δ ppm 15.11, 30.72, 37.03, 44.72, 113.32, 119.70, 120.52, 120.81, 127.78, 130.00, 130.01, 130.33, 136.49, 137.69, 139.35, 152.95, 155.4, 166.21. HRMS calcd for $C_{22}H_{20}N_4O_2SNa$ (M+Na)$^+$, 427.1199. found, 427.1200.

N-(naphthalen-2-yl)-2-((4-oxo-3-phenyl-4,5-dihydro-3H-pyrimido[5,4-b]indol-2-yl)thio)acetamide (18)

Cmpd 7a (50 mg, 0.14 mmol), 2-aminonaphthalene (44.82 mg, 0.16 mmol), triethylamine (39.63 μL, 0.28 mmol), and HATU (59.52 mg, 0.16 mmol) were reacted according to general procedure D to give 40.8 mg in 61% yield. $^1$H NMR (400 MHz, DMSO-d$_6$) δ ppm 4.16 (br s, 2H), 7.11 (t, J=7.70 Hz, 1H), 7.26-8.07 (m, 14H), 8.31 (br s, 1H), 10.65 (br s, 1H), 12.10 (br s, 1H). $^{13}$C NMR (126 MHz, DMSO-d$_6$) δ ppm 37.99, 113.27, 115.48, 119.71, 120.21, 120.49, 120.68, 120.72, 125.07, 126.92, 127.71, 127.74, 127.90, 128.89, 130.01, 130.06, 130.18, 130.41, 133.84, 136.49, 137.16, 137.63, 139.30, 152.89, 155.37, 166.96. HRMS calcd for $C_{28}H_{20}N_4O_2SNa$ (M+Na)$^+$, 499.1199. found, 499.1201.

N-(furan-2-ylmethyl)-2-((4-oxo-3-phenyl-4,5-dihydro-3H-pyrimido[5,4-b]indol-2-yl)thio)acetamide (19)

Cmpd 7a (50 mg, 0.14 mmol), furfurylamine (27.66 μL, 0.16 mmol), triethylamine (39.63 μL, 0.28 mmol), and HATU (59.52 mg, 0.16 mmol) were reacted according to general procedure D to give 50.37 mg in 83.6% yield. $^1$H NMR (400 MHz, DMSO-d$_6$) δ ppm 3.95 (s, 2H), 4.29 (d, J=5.50 Hz, 2H), 6.25 (d, J=3.30 Hz, 1H), 6.32 (t, J=2.57 Hz, 1H), 7.24 (t, J=6.97 Hz, 1H), 7.35-7.72 (m, 7H), 7.97 (d, J=7.70 Hz, 1H), 8.73 (t, J=5.32 Hz, 1H), 12.10 (br s, 1H). $^{13}$C NMR (126 MHz, DMSO-d$_6$) δ ppm 36.46, 36.76, 107.46, 107.48, 107.49, 110.86, 110.87, 110.89, 113.23, 119.71, 120.60, 120.80, 120.88, 127.76, 130.01, 130.02, 130.34, 136.50, 137.69, 139.34, 142.64, 152.32, 152.81, 155.41, 167.44. HRMS calcd for $C_{23}H_{18}N_4O_3SNa$ (M+Na)$^+$, 453.0992. found, 453.0995.

N-(1H-indazol-6-yl)-2-((4-oxo-3-phenyl-4,5-dihydro-3H-pyrimido[5,4-b]indol-2-yl)thio)acetamide (20)

Cmpd 7a (50 mg, 0.14 mmol), 2-aminoindazole (41.68 mg, 0.16 mmol), triethylamine (39.63 μL, 0.28 mmol), and HATU (59.52 mg, 0.16 mmol) were reacted according to general procedure D to give 32.7 mg in 50% yield. $^1$H NMR (400 MHz, DMSO-d$_6$) δ ppm 4.11 (s, 2H), 7.09 (t, J=7.33 Hz, 1H), 7.17 (d, J=8.43 Hz, 1H), 7.32-7.77 (m, 9H), 7.87-8.01 (m, 2H), 8.11 (s, 1H), 10.55 (br s, 1H), 12.07 (br s, 1H). $^{13}$C NMR (126 MHz, DMSO-d$_6$) δ ppm 38.00, 99.22, 113.29, 114.43, 119.60, 119.65, 120.55, 120.69, 121.03, 121.24, 127.81, 129.95, 130.10, 130.45, 133.80, 136.42, 137.66, 137.73, 139.31, 140.74, 148.09, 152.88, 155.37, 162.89, 167.00. HRMS calcd for $C_{25}H_{18}N_6O_2SNa$ (M+Na)$^+$, 489.1104. found, 489.1106.

2-((4-oxo-3-phenyl-4,5-dihydro-3H-pyrimido[5,4-b]indol-2-yl)thio)-N-(thiazol-2-yl)acetamide (21)

Cmpd 7a (50 mg, 0.14 mmol), 2-aminothiazole (31.35 mg, 0.16 mmol), triethylamine (39.63 μL, 0.28 mmol), and HATU (59.52 mg, 0.16 mmol) were reacted according to general procedure D to give 12.82 mg in 21.1% yield. $^1$H NMR (400 MHz, DMSO-d$_6$) δ ppm 4.17 (s, 2H), 6.90-7.27 (m, 2H), 7.30-7.78 (m, 8H), 7.83 (d, J=7.70 Hz, 1H), 12.03-12.16 (m, 1H). $^{13}$C NMR (126 MHz, DMSO-d$_6$) δ ppm 20.55, 28.58, 36.97, 46.95, 113.30, 119.71, 120.54, 120.77, 120.80, 127.76, 130.01, 130.32, 136.49, 137.68, 139.35, 152.91, 155.40, 167.27. HRMS calcd for $C_{21}H_{15}N_5O_2S_2Na$ (M+Na)$^+$, 456.0559. found, 456.0562.

N-ethyl-2-((4-oxo-3-phenyl-4,5-dihydro-3H-pyrimido[5,4-b]indol-2-yl)thio)acetamide (22)

Cmpd 7a (50 mg, 0.14 mmol), ethylamine (17.73 μL, 0.16 mmol), triethylamine (39.63 μL, 0.28 mmol), and HATU (59.52 mg, 0.16 mmol) were reacted according to general procedure D to give 22.9 mg in 43.3% yield. $^1$H NMR (400 MHz, DMSO-d$_6$) δ ppm 1.02 (t, J=7.15 Hz, 3H), 3.04-3.16 (m, 2H), 3.88 (s, 2H), 7.26 (t, J=7.33 Hz, 1H), 7.39-7.54 (m, 3H), 7.56-7.69 (m, 3H), 8.05 (d, J=8.07 Hz, 1H), 8.26 (m, 1H), 12.11 (s, 1H). $^{13}$C NMR (126 MHz, DMSO-d$_6$) δ ppm 15.12, 34.34, 37.01, 113.30, 119.70, 120.59, 120.74, 120.81, 127.76, 130.01, 130.32, 136.49, 137.68, 139.35, 152.88, 155.41, 167.02. HRMS calcd for $C_{20}H_{18}N_4O_2SNa$ (M+Na)$^+$, 401.1043. found, 401.1046.

N-butyl-2-((4-oxo-3-phenyl-4,5-dihydro-3H-pyrimido[5,4-b]indol-2-yl)thio)acetamide (23)

Cmpd 7a (50 mg, 0.14 mmol), butylamine (30.94 μL, 0.16 mmol), triethylamine (39.63 μL, 0.28 mmol), and HATU (59.52 mg, 0.16 mmol) were reacted according to general procedure D to give 18.6 mg in 44.7% yield. $^1$H NMR (400 MHz, DMSO-d$_6$) δ ppm 0.78 (t, J=7.31 Hz, 3H), 1.17-1.30 (m, 2H), 1.32-1.46 (m, 2H), 2.98-3.13 (m, 2H), 3.89 (s, 2H), 7.25 (t, J=6.83 Hz, 1H), 7.39-7.55 (m, 4H), 7.60 (m, J=5.40, 5.40 Hz, 3H), 8.04 (d, J=7.80 Hz, 1H), 8.17-8.25 (m, 1H), 12.10 (s, 1H). $^{13}$C NMR (126 MHz, DMSO d$_6$) δ ppm 13.61, 19.53, 31.2, 36.52, 38.7, 112.84, 119.26, 120.08, 120.32, 120.38, 127.3, 129.54, 129.55, 129.86, 136.05, 137.25, 138.93, 152.43, 154.96, 166.7. HRMS calcd for $C_{22}H_{22}N_4O_2SNa$ (M+Na)$^+$, 429.1356. found, 429.1359.

2-((4-oxo-3-phenyl-4,5-dihydro-3H-pyrimido[5,4-b]indol-2-yl)thio)-N-pentylacetamide (24)

Cmpd 7a (25 mg, 0.07 mmol), namylamine (20 μL, 0.16 mmol), triethylamine (19.82 μL, 0.14 mmol), and HATU (29.76 mg, 0.08 mmol) were reacted according to general procedure D to give 19.5 mg in 66% yield. $^1$H NMR (300 MHz, DMSO-d$_6$) δ ppm 0.74 (t, J=7.15 Hz, 3H), 1.07-1.25 (m, 4H), 1.31-1.45 (m, 2H), 2.98-3.15 (m, 2H), 3.88 (s, 2H), 7.24 (t, J=6.88 Hz, 1H), 7.40-7.54 (m, 3H), 7.56-7.68 (m, 3H), 8.04 (d, J=7.98 Hz, 1H), 8.20 (t, J=5.36 Hz, 1H), 12.10 (s, 1H). $^{13}$C NMR (126 MHz, DMSO-d$_6$) δ ppm 14.26, 22.29, 29.03, 29.25, 36.92, 113.27, 119.69, 120.52, 120.78, 120.81, 127.76, 130.00, 130.32, 136.48, 137.69, 139.35, 152.85, 155.40, 167.16. HRMS calcd for $C_{23}H_{25}N_4O_2S$ (M+H)$^+$, 421.1693. found, 421.1689.

N-hexyl-2-((4-oxo-3-phenyl-4,5-dihydro-3H-pyrimido[5,4-b]indol-2-yl)thio)acetamide (25)

Cmpd 7a (25 mg, 0.07 mmol), hexylamine (21 μL, 0.16 mmol), triethylamine (19.82 μL, 0.14 mmol), and HATU (29.76 mg, 0.08 mmol) were reacted according to general procedure D to give 20 mg in 65% yield. $^1$H NMR (300 MHz, DMSO-d$_6$) δ ppm 0.76 (t, J=6.46 Hz, 3H), 1.01-1.49 (m, 8H), 3.06 (q, J=6.60 Hz, 2H), 3.87 (s, 2H), 7.24 (t, J=6.80 Hz, 1H), 7.41-7.55 (m, 3H), 7.55-7.66 (m, 3H), 8.05 (d, J=7.70 Hz, 1H), 8.19 (t, J=5.23 Hz, 1H), 12.10 (s, 1H). $^{13}$C NMR (126 MHz, DMSO-d$_6$) δ ppm 14.29, 22.40, 26.49, 29.51, 31.40, 36.82, 113.28, 119.63, 120.55, 120.79, 120.81, 127.82, 129.94, 130.04, 130.36, 136.41, 137.72, 139.36, 152.80, 155.41, 167.33. HRMS calcd for $C_{24}H_{27}N_4O_2S$ (M+H)$^+$, 435.1849. found, 435.1846.

N-isobutyl-2-((4-oxo-3-phenyl-4,5-dihydro-3H-pyrimido[5,4-b]indol-2-yl)thio)acetamide (26)

Cmpd 7a (50 mg, 0.14 mmol), isobutylamine (31.11 µL, 0.16 mmol), triethylamine (39.63 µL, 0.28 mmol), and HATU (59.52 mg, 0.16 mmol) were reacted according to general procedure D to give 17.71 mg in 31% yield. $^1$H NMR (400 MHz, DMSO-d$_6$) δ ppm 0.72-0.92 (m, 6H), 1.68 (dt, J=13.47, 6.64 Hz, 1H), 2.91 (t, J=6.60 Hz, 2H), 3.93 (s, 2H), 7.25 (t, J=6.97 Hz, 1H), 7.40-7.56 (m, 3H), 7.61 (d, J=6.23 Hz, 3H), 8.04 (d, J=7.70 Hz, 1H), 8.23 (t, J=6.23 Hz, 1H), 12.11 (br s, 1H). $^{13}$C NMR (126 MHz, DMSO-d$_6$) δ ppm 20.55, 28.58, 36.97, 46.95, 113.30, 119.71, 120.54, 120.77, 120.80, 127.76, 130.01, 130.32, 136.49, 137.68, 139.35, 152.91, 155.40, 167.27. HRMS calcd for $C_{22}H_{22}N_4O_2SNa$ (M+Na)$^+$, 429.1356. found, 429.1359.

N-isopentyl-2-((4-oxo-3-phenyl-4,5-dihydro-3H-pyrimido[5,4-b]indol-2-yl)thio)acetamide (27)

Cmpd 7a (25 mg, 0.07 mmol), isopentylamine (20 µL, 0.16 mmol), triethylamine (19.82 µL, 0.14 mmol), and HATU (29.76 mg, 0.08 mmol) were reacted according to general procedure D to give 20 mg in 67% yield. $^1$H NMR (300 MHz, DMSO-d$_6$) δ ppm 0.78 (d, J=6.60 Hz, 6H), 1.29 (q, J=6.88 Hz, 2H), 1.54 (tt, J=13.38, 6.84 Hz, 1H), 3.08 (s, 2H), 3.88 (s, 2H), 7.24 (t, J=7.01 Hz, 1H), 7.36-7.68 (m, 6H), 8.04 (d, J=7.98 Hz, 1H), 8.17 (t, J=5.50 Hz, 1H), 12.10 (s, 1H). $^{13}$C NMR (126 MHz, DMSO-d$_6$) δ ppm 22.71, 25.45, 36.86, 37.68, 38.43, 113.29, 119.64, 120.55, 120.77, 120.80, 127.83, 129.95, 130.03, 130.35, 136.42, 137.71, 139.34, 152.82, 155.40, 167.23. HRMS calcd for $C_{23}H_{25}N_4O_2S$ (M+H)$^+$, 421.1693. found, 421.1689.

N-(3,3-dimethylbutyl)-2-((4-oxo-3-phenyl-4,5-dihydro-3H-pyrimido[5,4-b]indol-2-yl)thio)acetamide (28)

Cmpd 7a (25 mg, 0.07 mmol)), 3,3-dimethylbutylamine (20 µL, 0.16 mmol), triethylamine (19.82 µL, 0.14 mmol), and HATU (29.76 mg, 0.08 mmol) were reacted according to general procedure D and purified by reverse-phase chromatography (C18, 10:90 to 90:10 water:methanol gradient) to give 18 mg in 60% yield. $^1$H NMR (300 MHz, DMSO-d$_6$) δ ppm 0.83 (s, 9H), 1.26-1.47 (m, 2H), 3.00-3.16 (m, 2H), 3.86 (s, 2H), 7.24 (t, J=7.29 Hz, 1H), 7.39-7.55 (m, 3H), 7.56-7.70 (m, 3H), 8.04 (d, J=7.98 Hz, 1H), 8.17 (t, J=5.50 Hz, 1H), 12.10 (s, 1H). $^{13}$C NMR (126 MHz, DMSO-d$_6$) δ ppm 24.12, 28.28, 34.68, 37.17, 50.51, 113.31, 119.70, 120.48, 120.78, 120.81, 127.77, 130.00, 130.01, 130.32, 136.51, 137.68, 139.35, 153.01, 155.39, 165.92. HRMS calcd for $C_{24}H_{27}N_4O_2S$ (M+H)$^+$, 435.1849. found, 435.1846.

N-(3-methylpentyl)-2-((4-oxo-3-phenyl-4,5-dihydro-3H-pyrimido[5,4-b]indol-2-yl)thio)acetamide (29)

Cmpd 7a (25 mg, 0.07 mmol), 3-methylpentylamine (20 µL, 0.16 mmol), triethylamine (19.82 µL, 0.14 mmol) and HATU (29.76 mg, 0.08 mmol) according to general procedure D and purified by reverse-phase chromatography (C18, 10:90 to 90:10 water:methanol gradient) to give 17 mg in 55% yield. $^1$H NMR (400 MHz, DMSO-d$_6$) δ ppm 0.67-0.85 (m, 6H), 0.96-1.11 (m, 1H), 1.13-1.26 (m, 2H), 1.31 (dd, J=12.65, 6.42 Hz, 1H), 1.37-1.51 (m, 1H), 2.99-3.17 (m, 2H), 3.87 (s, 2H), 7.24 (t, J=7.52 Hz, 1H), 7.41-7.55 (m, 4H), 7.56-7.69 (m, 3H), 8.04 (d, J=8.07 Hz, 1H), 8.17 (t, J=5.50 Hz, 1H), 12.10 (s, 1H). $^{13}$C NMR (126 MHz, DMSO-d$_6$) δ ppm 11.42, 19.22, 29.22, 31.70, 36.16, 37.49, 113.27, 119.69, 120.50, 120.81, 127.77, 130.00, 130.01, 130.33, 136.48, 137.69, 139.36, 152.84, 155.40, 167.11. HRMS calcd for $C_{24}H_{26}N_4O_2SNa$ (M+Na)$^+$, 457.1669. found, 457.1670.

2-((4-oxo-3-phenyl-4,5-dihydro-3H-pyrimido[5,4-b]indol-2-yl)thio)-N-(pentan-2-yl)acetamide (30)

Cmpd 7a (25 mg, 0.07 mmol), 2-aminopentane (18.54 µL, 0.16 mmol), triethylamine (19.82 µL, 0.14 mmol), and HATU (29.76 mg, 0.08 mmol) according to general procedure D to give 19.1 mg in 65% yield. $^1$H NMR (400 MHz, DMSO-d$_6$) δ ppm 0.74 (t, J=6.97 Hz, 3H), 1.01 (d, J=6.60 Hz, 3H), 1.13-1.62 (m, 4H), 3.64-3.81 (m, 1H), 3.89 (s, 2H), 7.24 (t, J=7.33 Hz, 1H), 7.41-7.72 (m, 6H), 8.05 (t, J=6.60 Hz, 2H), 12.09 (br s, 1H). $^{13}$C NMR (126 MHz, DMSO-d$_6$) δ ppm 14.25, 19.32, 21.23, 37.11, 38.84, 44.94, 113.28, 119.68, 120.47, 120.77, 120.84, 127.75, 130.01, 130.32, 136.51, 137.68, 139.35, 152.97, 155.39, 166.36. HRMS calcd for $C_{23}H_{24}N_4O_2SNa$ (M+Na)$^+$, 443.1512. found, 443.1514.

2-((4-oxo-3-phenyl-4,5-dihydro-3H-pyrimido[5,4-b]indol-2-yl)thio)-N-(pentan-3-yl)acetamide (31)

Cmpd 7a (25 mg, 0.07 mmol), 3-aminopentane (18.24 µL, 0.16 mmol), triethylamine (19.82 µL, 0.14 mmol), and HATU (29.76 mg, 0.08 mmol) were reacted according to general procedure D to give 19.44 mg in 65% yield. $^1$H NMR (400 MHz, DMSO-d$_6$) δ ppm 0.77 (d, J=6.83 Hz, 6H), 1.21-1.62 (m, 4H), 3.47-3.58 (m, 1H), 3.93 (s, 1H), 7.24 (t, J=6.83 Hz, 1H), 7.37-7.76 (m, 6H), 7.93 (d, J=7.31 Hz, 1H), 8.05 (d, J=7.80 Hz, 1H), 12.10 (br s, 1H). $^{13}$C NMR (126 MHz, DMSO-d$_6$) δ ppm 10.87, 27.40, 37.00, 52.36, 113.29, 119.64, 120.50, 120.73, 120.86, 127.82, 129.95, 130.05, 130.36, 136.43, 137.71, 139.34, 152.98, 155.40, 167.06. HRMS calcd for $C_{23}H_{25}N_4O_2S$ (M+H)$^+$, 421.1693. found, 421.1695.

N-(tert-butyl)-2-((4-oxo-3-phenyl-4,5-dihydro-3H-pyrimido[5,4-b]indol-2-yl)thio)acetamide (32)

Cmpd 7a (50 mg, 0.14 mmol), t-butylamine (32.9 µL, 0.16 mmol), triethylamine (39.63 µL, 0.28 mmol), and HATU (59.52 mg, 0.16 mmol) were reacted according to general procedure D to give 22.6 mg in 39.7% yield. $^1$H NMR (400 MHz, DMSO-d$_6$) δ ppm 1.15-1.37 (m, 9H), 3.85 (s, 2H), 7.26 (t, J=6.83 Hz, 1H), 7.41-7.56 (m, 4H), 7.57-7.71 (m, 3H), 7.93 (s, 1H), 8.07 (d, J=7.80 Hz, 1H), 12.11 (s, 1H). $^{13}$C NMR (126 MHz, DMSO-d$_6$) δ ppm 28.86, 37.86, 50.89, 113.34, 119.68, 120.54, 120.74, 120.78, 127.76, 129.99, 130.00, 130.31, 136.54, 137.68, 139.37, 153.13, 155.40, 166.60. HRMS calcd for $C_{22}H_{22}N_4O_2SNa$ (M+Na)$^+$, 429.1356. found, 429.1359.

2-((4-oxo-3-phenyl-4,5-dihydro-3H-pyrimido[5,4-b]indol-2-yl)thio)-N-((tetrahydrofuran-2-yl)methyl)acetamide (33)

Cmpd 7a (50 mg, 0.14 mmol), tetrahydrofurfurylamine (32.31 μL, 0.16 mmol), triethylamine (39.63 μL, 0.28 mmol) and HATU (59.52 mg, 0.16 mmol) were reacted according to general procedure D to give 35 mg in 57.5% yield. IR: 3372, 3193 (NH), 1651 (CO) cm-1. $^1$H NMR (400 MHz, DMSO-d$_6$) δ ppm 1.32-1.61 (m, 1H), 1.63-2.06 (m, 3H), 2.96-3.26 (m, 2H), 3.52-3.64 (m, 1H), 3.64-3.75 (m, 1H), 3.76-3.86 (m, 1H), 3.92 (s, 2H), 7.25 (t, J=6.97 Hz, 1H), 7.35-7.71 (m, 6H), 8.07 (d, J=8.06 Hz, 1H), 8.30 (t, J=5.50 Hz, 1H), 12.10 (br s, 1H). $^{13}$C NMR (126 MHz, DMSO-d$_6$) δ ppm 25.12, 28.4, 36.38, 43.03, 67.15, 77.11, 112.81, 119.25, 120.11, 120.39, 127.32, 129.55, 129.57, 129.88, 136.05, 137.25, 138.92, 152.4, 154.95, 167.14. HRMS calcd for $C_{23}H_{22}N_4O_3SNa$ (M+Na)$^+$, 457.1305. found, 457.1308.

2-((4-oxo-3-phenyl-4,5-dihydro-3H-pyrimido[5,4-b]indol-2-yl)thio)-N-(piperidin-4-yl)acetamide (34)

Cmpd 7a (25 mg, 0.07 mmol), 4-aminopiperidine (16.6 uL, 0.16 mmol), triethylamine (19.82 ItL, 0.14 mmol), and HATU (29.76 mg, 0.08 mmol) were reacted according to general procedure D to give 17 mg in 65% yield. IR: 3372, 3193 (NH), 1651 (CO) cm-1. 1H NMR (400 MHz, DMSO-d$_6$) δ ppm 1.27 (d, J=11.36 Hz, 1H), 1.46 (d, J=9.90 Hz, 1H), 1.77-2.05 (m, 2H), 2.64-2.85 (m, 1H), 4.00-4.43 (m, 3H), 7.14-7.38 (m, 2H), 7.41-7.80 (m, 6H), 8.04 (d, J=7.70 Hz, 1H). 13C NMR (126 MHz, DMSO-d$_6$) δ ppm 33.41, 35.16, 36.00, 36.46, 40.91, 44.69, 45.37, 48.25, 113.30, 119.70, 120.67, 120.75, 120.79, 127.76, 130.00, 130.03, 130.33, 136.51, 137.63, 137.68, 139.36, 152.93, 152.97, 155.40, 165.44, 166.23. HRMS calcd for $C_{23}H_{24}N_5O_2S$ (M+H)+, 434.1645. found, 434.1648.

(Z)-3-((hydroxy(2-(2-((4-oxo-3-phenyl-4,5-dihydro-3H-pyrimido[5,4-b]indol-2-yl)thio)acetamido)ethoxy)phosphoryl)oxy)propane-1,2-diyl dioleate (35)

Cmpd 7a (50 mg, 0.14 mmol), DOPE (32.9 ItL, 0.16 mmol), triethylamine (39.63 ItL, 0.28 mmol), and HATU (59.52 mg, 0.16 mmol) were reacted according to general procedure D to give 16.4 mg in 10.9% yield. 1H NMR (400 MHz, DMSO-d$_6$) δ ppm 0.84 (t, J=6.83 Hz, 6H), 1.05-1.75 (m, 50H), 1.96 (br s, 8H), 2.23 (t, J=7.31 Hz, 4H), 3.02 (s, 3H), 3.14-3.26 (m, 2H), 3.59-3.83 (m, 3H), 3.90 (s, 2H), 4.02-4.17 (m, 1H), 4.26 (d, J=9.26 Hz, 1H), 5.06 (br s, 1H), 5.30 (br s, 3H), 7.24 (t, J=7.31 Hz, 1H), 7.38-7.75 (m, 6H), 8.09 (d, J=7.80 Hz, 1H), 8.87 (br s, 1H), 10.12 (br s, 1H), 12.08 (br s, 1H). 13C NMR (126 MHz, DMSO-d$_6$) δ ppm 8.84, 14.38, 14.39, 22.58, 24.85, 24.91, 27.02, 27.05, 28.88, 28.91, 28.98, 29.00, 29.07, 29.12, 29.19, 29.33, 29.43, 29.45, 29.57, 31.77, 33.82, 34.00, 37.11, 45.62, 62.78, 63.05, 70.84, 70.89, 113.19, 119.66, 120.61, 120.86, 120.89, 127.62, 129.96, 130.00, 130.27, 136.50, 137.72, 139.36, 152.72, 155.40, 167.22, 172.67, 172.91. HRMS calcd for $C_{59}H_{89}N_4O_{10}PSNa$ (M+Na)+, 1099.5929. found, 1099.5930.

N-cyclohexyl-2-((3-cyclohexyl-4-oxo-4,5-dihydro-3H-pyrimido[5,4-b]indol-2-yl)thio)acetamide (36)

Cmpd 7b (17.7 mg, 0.05 mmol), triethylamine (13.8 ItL, 0.1 mmol), and cyclohexylamine (6.2 ItL, 0.06 mmol) were dissolved in anhydrous DMF (0.5 mL). HATU (20.74 mg, 0.06 mmol) dissolved in 0.2 mL of DMF was added to the reaction mixture and stirred for 20 min and concentrated in vacuo. The crude material was recrystallized in MeOH to give 9.1 mg in 41% yield. 1H NMR (400 MHz, DMSO-d$_6$) δ ppm 0.99-2.17 (m, 16H), 2.60-2.88 (m, 4H), 3.99 (br s, 2H), 4.17-4.45 (m, 1H), 7.20 (t, J=7.33 Hz, 1H), 7.34-7.65 (m, 2H), 8.01 (d, J=8.07 Hz, 1H), 8.22 (d, J=6.97 Hz, 1H), 11.86 (br s, 1H). 13C NMR (126 MHz, DMSO-d$_6$) δ ppm 19.02, 24.92, 25.28, 25.63, 26.36, 28.79, 32.87, 37.21, 48.49, 56.47, 61.95, 113.22, 120.27, 120.56, 120.72, 120.82, 127.59, 136.47, 139.26, 151.90, 155.96, 166.22. HRMS calcd for $C_{24}H_{30}N_4O_2SNa$ (M+Na)+, 461.1982. found, 461.1983.

N-cyclohexyl-2-((3-(naphthalen-2-yl)-4-oxo-4,5-dihydro-3H-pyrimido[5,4-b]indol-2-yl)thio)acetamide (39)

Cmpd 7c (26.1 mg, 0.065 mmol), triethylamine (18.1 yL, 0.13 mmol), and cyclohexylamine (8.2 yL, 0.071 mmol) were dissolved in anhydrous DMF (0.1 mL). HATU (27.2 mg, 0.071 mmol) dissolved in 0.2 mL of DMF was added to the reaction mixture and stirred for 20 min and concentrated in vacuo. The crude material was recrystallized in MeOH to give 27 mg in 86% yield. 1H NMR (400 MHz, DMSO-d6) δ ppm 0.76-1.38 (m, 5H), 1.42-1.95 (m, 5H), 3.43-3.55 (m, 1H), 3.74-4.00 (m, 2H), 7.29 (t, J=6.97 Hz, 1H), 7.41 (d, J=8.43 Hz, 1H), 7.47-7.66 (m, 4H), 7.68-7.81 (m, 2H), 8.01-8.36 (m, 4H), 12.17 (s, 1H). 13C NMR (126 MHz, DMSO-d6) δ ppm 24.82, 25.57, 31.23, 32.72, 32.75, 36.27, 36.97, 48.36, 113.39, 119.55, 120.69, 120.81, 120.84, 122.13, 126.31, 127.24, 127.99, 128.25, 128.88, 129.03, 130.07, 130.92, 132.83, 134.46, 138.05, 139.48, 153.40, 155.47, 162.87, 166.19. HRMS calcd for $C_{28}H_{26}N_4O_2SNa$ (M+Na)$^+$, 505.1669. found, 505.1671.

N-cyclohexyl-2-((4-oxo-3-phenethyl-4,5-dihydro-3H-pyrimido[5,4-b]indol-2-yl)thio)acetamide (40)

Cmpd 7d (25 mg, 0.066 mmol), triethylamine (19.5 μL, 0.13 mmol), and cyclohexylamine (8.2 μL, 0.073 mmol) were dissolved in anhydrous DMF (0.1 mL). HATU (27.2 mg, 0.073 mmol) dissolved in 0.2 mL of DMF was added to the reaction mixture and stirred for 20 min and concentrated in vacuo. The crude material was recrystallized in MeOH to give 18.28 mg in 60% yield. $^1$H NMR (400 MHz, DMSO-d$_6$) δ ppm 0.83-1.42 (m, 5H), 1.44-2.08 (m, 5H), 2.87-3.17 (m, 2H), 3.95-4.24 (m, 2H), 4.25-4.62 (m, 2H), 7.33 (br s, 6H), 7.87-8.48 (m, 3H), 11.99 (s, 2H). $^{13}$C NMR (126 MHz, DMSO-d$_6$) δ ppm 24.91, 25.63, 32.83, 34.09, 36.63, 45.66, 48.51, 113.26, 119.40, 120.37, 120.67, 120.84, 127.16, 127.76, 129.10, 137.30, 138.26, 139.36, 151.68, 154.92, 166.19. HRMS calcd for $C_{26}H_{28}N_4O_2SNa$ (M+Na)$^+$, 483.1825. found, 483.1827.

2-((3-Cyclohexyl-4-oxo-4,5-dihydro-3H-pyrimido[5,4-b]indol-2-yl)thio)-N-cyclopentylacetamide (41)

Cmpd 7b (25 mg, 0.07 mmol), triethylamine (19.5 μL, 0.14 mmol), and cyclopentylamine (8.82 μL, 0.08 mmol) were dissolved in anhydrous DMF (0.5 mL). HATU (29.3 mg, 0.08 mmol) dissolved in 0.2 mL of DMF was added to the reaction mixture and stirred for 20 min and concentrated in vacuo. The crude material was recrystallized in MeOH to give 9.3 mg in 30.3% yield. 1H NMR (400 MHz, DMSO-d$_6$) δ ppm 0.97-2.09 (m, 18H), 2.61-2.83 (m, 4H), 4.02 (br s, 1H), 4.17-4.37 (m, 1H), 7.20 (t, J=7.30 Hz, 1H), 7.36-7.56 (m, 2H), 8.00 (d, J=8.06 Hz, 1H), 8.32 (d, J=7.33 Hz, 1H), 11.86 (br s, 1H). $^{13}$C NMR (126 MHz, DMSO-d6) δ ppm 23.97, 25.25, 26.34, 28.78, 32.73, 37.02, 51.21, 61.99, 113.23, 120.31, 120.54, 120.67, 120.79, 127.66, 136.48, 139.24, 151.93, 155.94, 166.85. HRMS calcd for $C_{23}H_{28}N_4O_2SNa$ (M+Na)$^+$, 447.1825. found, 447.1827.

N-cyclohexyl-2-((5-methyl-4-oxo-3-phenyl-4,5-dihydro-3H-pyrimido[5,4-b]indol-2-yl)thio)acetamide (42) and N-cyclohexyl-N-methyl-2-((5-methyl-4-oxo-3-phenyl-4,5-dihydro-3H-pyrimido[5,4-b]indol-2-yl)thio)acetamide (43)

To a solution of Cmpd 1 (50 mg, 0.12 mmol) in DMF (1 mL) in a flame-dried flask was added NaH 60% dispersion in mineral oil (9.24 mg, 0.24 mmol) and stirred at room temperature for 10 min. Methyl iodide (14.3 μL, 0.24 mmol) was then added to the solution and stirred overnight. Reaction mixture was concentrated and purified by preparative thin-layer chromatography (40:60 ethyl acetate:hexane) to give 18.18 mg in 33.9% yield of Cmpd 42 and 5.3 mg in 9.6% yield of Cmpd 43. 42: $^1$H NMR (400 MHz, DMSO-d$_6$) δ ppm 0.93-1.37 (m, 5H), 1.40-1.90 (m, 5H), 3.44-3.58 (m, 1H), 3.88 (s, 2H), 4.15 (s, 3H), 7.31 (t, J=7.33 Hz, 1H), 7.39-7.53 (m, 2H), 7.53-7.78 (m, 5H), 8.05-8.27 (m, 2H). $^{13}$C NMR (126 MHz, DMSO-d$_6$) δ ppm 24.90, 25.62, 31.47, 32.82, 37.14, 48.41, 111.31, 119.12, 120.09, 120.74, 120.92, 128.03, 129.99, 130.34, 136.35, 137.47, 140.40, 153.27, 155.75, 166.14. HRMS calcd for $C^{25}H^{27}N^4O^2S$ (M+H)$^+$, 447.1849. found, 447.1852. 43: $^1$H NMR (400 MHz, DMSO-d$_6$) δ ppm 0.76-1.98 (m, 10H), 2.10 (s, 3H), 3.97 (s, 2H), 4.23 (s, 3H), 7.16 (t, J=7.52 Hz, 1H), 7.26-7.85 (m, 8H), 8.07 (d, J=7.70 Hz, 1H). $^{13}$C NMR (126 MHz, DMSO-d$_6$) δ ppm 24.85, 25.60, 31.43, 32.28, 38.02, 50.24, 62.03, 111.44, 119.63, 120.34, 120.85, 121.08, 128.20, 129.74, 130.25, 135.43, 136.73, 139.34, 155.99, 156.50, 169.99. HRMS calcd for $C_{26}H_{29}N_4O_2S$ (M+H)$^+$, 461.2006. found, 461.2007.

Methyl 4-(2-((2-(cyclohexylamino)-2-oxoethyl)thio)-4-oxo-3-phenyl-3H-pyrimido[5,4-b]indol-5(4H)-yl)butanoate (44)

To a flame-dried flask, bromobutyric acid (50 μL, 0.43 mmol) was dissolved in anhydrous MeOH (3 mL) followed by the addition of TMSCl (272.45 μL, 2.15 mmol). The solution was stirred overnight at room temperature and concentrated in vacuo to remove all trace of MeOH and HCl. In a separate flame-dried flask, Cmpd 1 (25 mg, 0.06 mmol) was dissolved in DMF (1 mL). NaH 60% dispersion (2.31 mg, 0.06 mmol) was added to the solution. After stirring at room temperature for 10 min, methyl iodide (3.6 yL, 0.06 mmol) was added and stirred for an additional 12 h. The reaction mixture was concentrated in vacuo and purified by preparative thin-layer chromatography to give 1.3 mg in 4% yield. IR: 3293 (NH), 1732 (CO ester), 1683 (CO amide) cm$^{-1}$. $^1$H NMR (400 MHz, DMSO-d$_6$) δ ppm 0.99-1.32 (m, 5H), 1.52 (d, J=12.19 Hz, 1H), 1.57-1.80 (m, 4H), 1.91-2.10 (m, 2H), 2.29 (t, J=7.31 Hz, 2H), 3.47 (s, 3H), 3.47 (br s, 1H), 3.89 (s, 2H), 4.62 (t, J=6.83 Hz, 2H), 7.30 (t, J=7.56 Hz, 1H), 7.39-7.51 (m, 2H), 7.52-7.68 (m, 4H), 7.74 (s, 1H), 8.11 (d, J=7.80 Hz, 1H), 8.17 (d, J=7.80 Hz, 1H). $^{13}$C NMR (126 MHz, DMSO-d$_6$) δ ppm 24.88, 25.59, 26.00, 30.71, 32.79, 37.02, 51.71, 111.34, 118.74, 120.19, 120.80, 121.09, 128.18, 129.93, 130.02, 130.37, 136.29, 137.81, 139.77, 153.45, 155.47, 166.28, 173.19. HRMS calcd for $C_{29}H_{32}N_4O_4SNa$ (M+Na)$^+$, 555.2036. found, 555.2036.

tert-Butyl 2-((4-oxo-3-phenyl-4,5-dihydro-3H-pyrimido[5,4-b]indol-2-yl)thio)acetate (45)

Cmpd 6a (100 mg, 0.34 mmol) and KOH (38.2 g, 0.68 mmol) were suspended in 2 mL of dimethylacetamide in a flame-dried flask with stirring. H$_2$O was added dropwise until KOH was completely dissolved. t-Butyl chloroacetate (49 μL, 0.34 mmol) was immediately added to the reaction mixture and stirred at room temperature monitoring with thin-layer chromatography (1:99 MeOH:DCM). Upon completion, reaction mixture was extracted with ethyl acetate (20 mL) and water (40 mL), dried over MgSO$_4$, and concentrated in vacuo. EtOH (5 mL) was added to the resulting viscous liquid, and pure product was filtered to give 55 mg in 40% yield. IR: 3192 (NH), 1732 (CO ester), 1674 (CO amide) cm$^1$. $^1$H NMR (400 MHz, DMSO-d$_6$) δ ppm 1.32-1.48 (m, 9H), 3.91 (s, 2H), 7.26 (t, J=7.31 Hz, 1H), 7.42-7.55 (m, 4H), 7.56-7.69 (m, 3H), 7.96 (d, J=8.29 Hz, 1H), 12.13 (s, 1H). HRMS calcd for $C_{22}H_{21}N_3O_3SNa$ (M+Na)$^+$, 430.1196. found, 430.1197.

tert-Butyl 2-((4-oxo-3-phenyl-5-propyl-4,5-dihydro-3H-pyrimido[5,4-b]indol-2-yl)thio)acetate (46a)

Cmpd 45 (50 mg, 0.12 mmol), NaH 60% dispersion in mineral oil (3.3 mg, 0.14 mmol), iodopropane (13.1 μL, 0.14 mmol), and DMF (1 mL) were reacted according to general procedure E and purified by silica gel chromatography (10:90 ethyl acetate:hexane) to give 32.8 mg in 61% yield. $^1$H NMR (400 MHz, DMSO-d$_6$) δ ppm 0.82 (t, J=7.31 Hz, 3H), 1.40 (s, 9H), 1.66-1.95 (m, 2H), 3.91 (s, 2H), 4.56 (t, J=6.58 Hz, 2H), 7.30 (br s, 1H), 7.39-7.68 (m, 6H), 7.75 (d, J=8.29 Hz, 1H), 7.99 (d, J=7.80 Hz, 1H). HRMS calcd for $C_{25}H_{27}N_3O_3SNa$ (M+Na)$^+$, 472.1665. found, 472.1668.

tert-Butyl 2-((4-oxo-5-pentyl-3-phenyl-4,5-dihydro-3H-pyrimido[5,4-b]indol-2-yl)thio)acetate (46b)

Cmpd 45 (50 mg, 0.12 mmol), NaH 60% dispersion in mineral oil (3.3 mg, 0.14 mmol), iodopentane (17.64 μL, 0.14 mmol), and DMF (1 mL) were reacted according to general procedure E and purified by silica gel chromatography (10:90 ethyl acetate:hexane) to give 33.8 mg in 59% yield. 1H NMR (400 MHz, DMSO-d$_6$) δ ppm 0.80 (t, J=6.83 Hz, 3H), 1.25 (d, J=6.83 Hz, 4H), 1.32-1.55 (m, 9H), 1.64-1.83 (m, 2H), 3.91 (s, 2H), 4.59 (t, J=7.31 Hz, 2H), 7.30 (t, J=7.56 Hz, 1H), 7.46 (dd, J=7.56, 1.71 Hz, 2H), 7.54 (t, J=7.31 Hz, 1H), 7.57-7.67 (m, 3H), 7.72 (d, J=8.78 Hz, 1H), 7.99 (d, J=7.80 Hz, 1H). HRMS calcd for $C_{27}H_{31}N_3O_3SNa$ (M+Na)$^+$, 500.1978. found, 500.1975.

tert-Butyl 2-((5-dodecyl-4-oxo-3-phenyl-4,5-dihydro-3H-pyrimido[5,4-b]indol-2-yl)thio)acetate (46c)

Cmpd 45 (50 mg, 0.12 mmol), NaH 60% dispersion in mineral oil (3.3 mg, 0.14 mmol), bromododecane (32.4 μL, 0.14 mmol), and DMF (1 mL) were reacted according to general procedure E and purified by silica gel chromatography (10:90 ethyl acetate:hexane) to give 37.4 mg in 54% yield. $^1$H NMR (400 MHz, DMSO-d$_6$) δ ppm 0.84 (t, J=6.83 Hz, 3H), 1.21 (br s, 18H), 1.40 (s, 9H), 1.64-1.86 (m, 3H), 3.91 (s, 2H), 4.59 (t, J=7.07 Hz, 2H), 7.29 (t, J=7.80 Hz, 1H), 7.45 (dd, J=7.31, 1.95 Hz, 2H), 7.54 (t, J=7.80 Hz, 1H), 7.58-7.67 (m, 3H), 7.72 (d, J=8.29 Hz, 1H), 7.98 (d, J=7.80 Hz, 1H). HRMS calcd for $C_{34}H_{45}N_3O_3SNa$ (M+Na)$^+$, 598.3074. found, 598.3070.

tert-Butyl 2-((5-(cyanomethyl)-4-oxo-3-phenyl-4,5-dihydro-3H-pyrimido[5,4-b]indol-2-yl)thio)acetate (46d)

Cmpd 45 (318 mg, 0.78 mmol), NaH 60% dispersion (38.16 mg, 0.86 mmol), bromoacetonitrile (65.5 µL, 0.86 mmol), and DMF (20 mL) were reacted according to general procedure E to give 247.8 mg in 71% yield. $^1$H NMR (400 MHz, DMSO-d$_6$) δ ppm 1.41 (s, 9H), 3.94 (s, 2H), 5.87 (s, 2H), 7.43 (t, J=7.31 Hz, 1H), 7.47-7.55 (m, 2H), 7.58-7.72 (m, 4H), 7.88 (d, J=8.78 Hz, 1H), 8.03 (d, J=8.29 Hz, 1H). HRMS calcd for $C_{24}H_{22}N_4O_3SNa$ (M+Na)$^+$, 469.1305. found, 469.1303.

2-((4-oxo-3-phenyl-5-propyl-4,5-dihydro-3H-pyrimido[5,4-b]indol-2-yl)thio)acetic acid (47a)

Cmpd 46a (29.74 mg, 0.07 mmol), acetonitrile (1 mL), and trifluoroacetic acid (1 mL) were reacted according to general procedure F to give 26 mg in quantitative yield. $^1$H NMR (400 MHz, DMSO-d$_6$) δ ppm 0.81 (t, J=6.58 Hz, 3H), 1.75 (m, 2H), 3.96 (s, 2H), 4.56 (t, J=7.07 Hz, 2H), 7.29 (t, J=7.31 Hz, 1H), 7.38-7.88 (m, 7H), 7.99 (d, J=8.29 Hz, 1H). HRMS calcd for $C_{21}H_{19}N_3O_3SNa$ (M+Na)$^+$, 416.1039. found, 416.1036.

2-((4-oxo-5-pentyl-3-phenyl-4,5-dihydro-3H-pyrimido[5,4-b]indol-2-yl)thio)acetic acid (47b)

Cmpd 46b (30.98 mg, 0.065 mmol), acetonitrile (1 mL), and trifluoroacetic acid (1 mL) were reacted according to general procedure F to give 27 mg in quantitative yield. $^1$H NMR (400 MHz, DMSO-d$_6$) δ ppm 0.81 (t, J=6.58 Hz, 3H), 0.99-1.43 (m, 4H), 1.62-1.84 (m, 2H), 3.96 (s, 2H), 4.59 (t, J=7.07 Hz, 2H), 7.29 (t, J=7.31 Hz, 1H), 7.45 (br s, 2H), 7.51-7.68 (m, 4H), 7.72 (d, J=8.29 Hz, 1H), 7.98 (d, J=8.29 Hz, 1H). HRMS calcd for $C_{23}H_{23}N_3O_3SNa$ (M+Na)$^+$, 444.1352. found, 444.1351.

2-((5-dodecyl-4-oxo-3-phenyl-4,5-dihydro-3H-pyrimido[5,4-b]indol-2-yl)thio)acetic acid (47c)

Cmpd 46c (34.81 mg, 0.06 mmol), acetonitrile (1 mL), and trifluoroacetic acid (1 mL) were reacted according to general procedure F to give 28.6 mg in 92% yield. $^1$H NMR (400 MHz, DMSO-d$_6$) δ ppm 0.82 (t, J=6.83 Hz, 3H), 1.19 (d, J=7.80 Hz, 18H), 1.71 (d, J=6.34 Hz, 2H), 3.94 (s, 2H), 4.56 (t, J=7.07 Hz, 2H), 7.27 (t, J=7.80 Hz, 1H), 7.36-7.47 (m, 2H), 7.59 (s, 4H), 7.70 (d, J=8.29 Hz, 1H), 7.96 (d, J=7.80 Hz, 1H), 12.74 (br s, 1H). HRMS calcd for $C_{30}H_{37}N_3O_3SNa$ (M+Na)$^+$, 542.2448. found, 542.2444.

2-((5-(cyanomethyl)-4-oxo-3-phenyl-4,5-dihydro-3H-pyrimido[5,4-b]indol-2-yl)thio)acetic acid (47d)

Cmpd 46a (29.74 mg, 0.07 mmol), acetonitrile (1 mL), and trifluoroacetic acid (1 mL) were reacted according to general procedure F to give 26 mg in quantitative yield. $^1$H NMR (400 MHz, DMSO-d$_6$) δ ppm 3.84-4.15 (m, 2H), 5.87 (s, 2H), 7.42 (t, J=7.56 Hz, 1H), 7.47-7.56 (m, 2H), 7.57-7.74 (m, 4H), 7.88 (d, J=8.29 Hz, 1H), 8.03 (d, J=7.80 Hz, 1H), 12.89 (br s, 1H). HRMS calcd for $C_{20}H_{14}N_4O_3SNa$ (M+Na)$^+$, 413.0679. found, 413.0676.

N-cyclohexyl-2-((4-oxo-3-phenyl-5-propyl-4,5-dihydro-3H-pyrimido[5,4-b]indol-2-yl)thio)acetamide (48)

Cmpd 47a (29.4 mg, 0.075 mmol), HATU (31.3 mg, 0.082 mmol), triethylamine (20.8 µL, 0.15 mmol), cyclohexylamine (9.43 µL, 0.082 mmol), and DMF (1 mL) were reacted according to general procedure D to give 4 mg in 11% yield. $^1$H NMR (400 MHz, DMSO-d$_6$) δ ppm 0.82 (t, J=7.33 Hz, 3H), 1.00-1.37 (m, 5H), 1.42-1.99 (m, 7H), 3.88 (s, 2H), 4.56 (t, J=6.97 Hz, 2H), 7.29 (t, J=7.70 Hz, 1H), 7.41-7.50 (m, 1H), 7.50-7.68 (m, 4H), 7.74 (d, J=8.43 Hz, 1H), 8.10 (d, J=8.07 Hz, 1H), 8.17 (d, J=8.07 Hz, 1H). $^{13}$C NMR (126 MHz, DMSO-d$_6$) δ ppm 11.35, 24.15, 24.89, 25.61, 32.83, 37.12, 45.80, 48.40, 111.49, 118.75, 120.09, 120.61, 120.99, 127.98, 129.96, 129.98, 130.29, 136.38, 137.68, 139.83, 153.35, 155.43, 166.14. HRMS calcd for $C_{27}H_{31}N_4O_2S$ (M+H)$^+$, 475.2162. found, 475.2164.

N-cyclohexyl-2-((4-oxo-5-pentyl-3-phenyl-4,5-dihydro-3H-pyrimido[5,4-b]indol-2-yl)thio)acetamide (49)

Cmpd 47b (34 mg, 0.08 mmol), HATU (34 mg, 0.088 mmol), triethylamine (22.5 µL, 0.16 mmol), cyclohexylamine (10.2 µL, 0.088 mmol), and DMF (1 mL) were reacted according to general procedure D to give 21 mg in 52% yield. $^1$H NMR (400 MHz, DMSO-d$_6$) δ ppm 0.80 (t, J=6.97 Hz, 3H), 1.00-1.40 (m, 9H), 1.43-1.92 (m, 7H), 3.44-3.58 (m, 1H), 3.88 (s, 2H), 4.58 (t, J=7.15 Hz, 2H), 7.29 (t, J=7.33 Hz, 1H), 7.40-7.68 (m, 6H), 7.72 (d, J=8.43 Hz, 1H), 8.03-8.32 (m, 2H). $^{13}$C NMR (126 MHz, DMSO-d$_6$) δ ppm 14.35, 22.29, 24.91, 25.62, 28.70, 30.56, 32.84, 37.11, 44.38, 48.42, 111.45, 118.70, 120.13, 120.64, 121.02, 128.02, 129.99, 130.31, 136.39, 137.70, 139.74, 153.36, 155.44, 166.16. HRMS calcd for $C_{29}H_{34}N_4O_2S$ (M+H)$^+$, 502.24025. found, 502.24018.

N-cyclohexyl-2-((5-dodecyl-4-oxo-3-phenyl-4,5-dihydro-3H-pyrimido[5,4-b]indol-2-yl)thio)acetamide (50)

Cmpd 47c (28.6 mg, 0.055 mmol), HATU (23 mg, 0.061 mmol), triethylamine (15.33 µL, 0.110 mmol), cyclohexylamine (7 µL, 0.061 mmol), and DMF (1 mL) were reacted according to general procedure D and purified by silica gel chromatography (20:80 ethyl acetate:hexane) to give 22 mg in 67% yield. $^1$H NMR (400 MHz, DMSO-d$_6$) δ ppm 0.73-0.92 (m, 4H), 1.20 (d, J=6.97 Hz, 22H), 1.41-1.89 (m, 7H), 3.45-3.61 (m, 1H), 3.88 (s, 2H), 4.58 (t, J=6.60 Hz, 2H), 7.28 (t, J=7.52 Hz, 1H), 7.36-7.80 (m, 7H), 8.05-8.26 (m, 2H). $^{13}$C NMR (126 MHz, DMSO-d$_6$) δ ppm 11.85, 14.50, 22.63, 24.97, 25.70, 26.59, 29.19, 29.44, 30.88, 31.82, 32.90, 37.20, 44.48, 48.42, 111.54, 118.70, 120.22, 120.69, 121.09, 128.06, 130.05, 130.39, 136.46, 137.79, 139.83, 153.41, 155.50, 166.17. HRMS calcd for $C_{36}H_{49}N_4O_2S$ (M+H)$^+$, 601.3571. found, 601.3570.

2-((5-(cyanomethyl)-4-oxo-3-phenyl-4,5-dihydro-3H-pyrimido[5,4-b]indol-2-yl)thio)-N-cyclohexylacetamide (51)

Cmpd 47d (150 mg, 0.39 mmol), HATU (161 mg, 0.42 mmol), triethylamine (59 µL, 0.77 mmol), cyclohexylamine (49 μL, 0.42 mmol), and DMF (5 mL) were reacted according to general procedure D to give 157.3 mg in 86.7% yield. IR: 3240 (NH), 1697 (CO) cm-1. $^1$H NMR (400 MHz, DMSO-d$_6$) δ ppm 0.97-1.33 (m, 5H), 1.45-1.87 (m, 5H), 3.45-3.58 (m, 1H), 3.90 (s, 2H), 5.87 (s, 2H), 7.42 (t, J=7.80 Hz, 1H), 7.47-7.56 (m, 2H), 7.57-7.74 (m, 4H), 7.88 (d, J=8.29 Hz, 1H), 8.17 (dd, J=13.16, 7.80 Hz, 2H). 13C NMR (126 MHz, DMSO-d$_6$) δ ppm 24.92, 25.62, 32.84, 33.04, 37.21, 48.45, 111.45, 116.75, 118.20, 121.01, 121.35, 122.12, 129.02, 129.90, 130.08, 130.56, 135.95, 138.98, 139.65, 155.44, 155.50, 166.02. HRMS calcd for $C_{26}H_{26}N_5O_2S$ (M+H)$^+$, 472.1802. found, 472.1803.

2-((5-(2-amino-2-oxoethyl)-4-oxo-3-phenyl-4,5-dihydro-3H-pyrimido[5,4-b]indol-2-yl)thio)-N-cyclohexylacetamide (52)

A KOH (6 mg, 0.11 mmol) solution in water (50 μL) was added to a solution of Cmpd 51 in dimethylacetamide (200 μL) and stirred at rt overnight. Reaction mixture was acidified with 3 M HCl, extracted with ethyl acetate and water, dried over MgSO4, and concentrated to dryness in vacuo. Further recrystallization in MeOH gives 20 mg in 37% yield. 1H NMR (400 MHz, DMSO-d6) δ ppm 0.94-1.36 (m, 5H), 1.43-1.89 (m, 5H), 3.43-3.62 (m, 1H), 3.89 (s, 2H), 5.24 (s, 2H), 7.12-7.22 (m, 1H), 7.30 (t, J=7.33 Hz, 1H), 7.42 (m, J=7.30, 2.20 Hz, 2H), 7.48-7.67 (m, 5H), 8.10 (d, J=7.70 Hz, 1H), 8.18 (d, J=7.70 Hz, 1H). $^{13}$C NMR (126 MHz, DMSO-d$_6$) δ ppm 24.90, 25.59, 32.82, 37.05, 46.85, 48.48, 111.36, 119.30, 120.36, 120.91, 120.95, 128.13, 129.87, 130.05, 130.41, 136.14, 137.82, 140.64, 153.47, 155.65, 166.26, 169.77. HRMS calcd for $C_{26}H_{27}N_5O_3SNa$ (M+Na)$^+$, 512.1727. found, 512.1726.

Biological Studies

Animals.

Seven- to nine-week-old C57BL/6 (wild-type, WT) and Cd14$^{-/-}$ (C57BL/6 background) test subjects were purchased from the Jackson Laboratories (Bar Harbor, Mass.). Tlr4$^{-/-}$ mice were a gift from Dr. Shizuo Akira (Osaka University, Japan) and backcrossed for 10 generations onto the C57BL/6 background at University of California, San Diego (UCSD). All animal experiments were approved by the UCSD Institutional Animal Care and Use Committee.

In Vitro Cytokine Induction in Bone Marrow Derived Dendritic Cells (BMDC).

BMDC were prepared from C57BL/6 mice as described. See e.g., Wu, C. C. et al. *Proc. Natl. Acad. Sci. U.S.A.* 2007, 104:3990-3995. BMDC (10$^5$ cells per well) were plated in 96-well plates in 200 μL of complete RPMI1640 supplemented with 10% fetal calf serum (FCS; Sigma Aldrich), 100 U/mL penicillin, and 100 μg/mL streptomycin (Invitrogen). The cells were incubated with graded concentrations of the compounds for 18 h at 37° C., 5% CO$_2$. After 18 h incubation, the cell culture supernatants were collected. LPS (purified LPS, Invivogen, San Diego, Calif.) or MPLA (1 μg/mL synthetic MPLA, Invivogen, San Diego, Calif.) were used as positive controls. The levels of IL-6 in the culture supernatants were determined by ELISA (BD Biosciences, La Jolla, Calif.). See e.g., Chan, M. et al., *Bioconjugate Chem* 2009, 20:1194-1200. The AUC was calculated from BMDC dose-response curves using Prism 5 (GraphPad, San Diego). Each cytokine induction curve was first converted to a percent activity curve, and then the AUC of the percent activity curve was calculated. The process of converting to a percent activity curve allowed subtracting background and adjusting for plate-to-plate variation. Finally, the AUC values were normalized to the activity of Cmpd 1 within each experiment, set at 100. The cultures stimulated with LPS 10 ng/mL, and 5 μM Cmpd 1 released an average of 20.6 ng/mL±4.7 SD and 10.5 ng/mL±1.3 SD of IL-6, respectively.

In Vitro Assay Using TLR Reporter Cell Lines.

Murine or humanTLR4 HEK Blue cells (Invivogen, 2.5× 10$^4$ cells per well of a 96-well plate), or NFκB/SEAPorter HEK293 cells (Imgenex, San Diego, Calif.) for human TLR2, TLR3, TLR5, TLR7, TLR8, or TLR9 (5×10$^4$ cells per well of 96 well plate) were incubated with graded doses of Cmpd 1. The culture supernatants were harvested after a 20-24 h incubation period. SEAP activity in the supernatants was determined by a colorimetric assay, using either the SEAPorter Assay Kit (Imgenex), with absorbance read at 405 nm, or QuantiBlue (Invivogen), with absorbance read at 630 nm. Stimulation of the human TLR4 cells with 10 ng/mL LPS resulted in OD$_{630}$ of 1.90 relative to 0.88 of cells stimulated with 10 μM Cmpd 1. The relative reporter activation for the murine TLR4 cells for cells stimulated with 10 ng/mL LPS and 5 μM Cmpd 1 was 1.70±0.08 and 1.52±0.03, respectively.

In Vitro Activities in Human Peripheral Blood Mononuclear Cells (hPBMC).

Human PBMC were isolated from buffy coats obtained from the San Diego Blood Bank (San Diego, Calif.) as described previously. See; e.g., Chan, M. et al., *Bioconjugate Chem* 2009, 20:1194-1200; Hayashi, T. et al., *Infect. Immun.* 2001, 69:6156-6164) hPBMC (1×10$^6$/mL) were incubated with various compounds in complete RPMI for 18 h at 37° C., 5% CO$_2$, and culture supernatants were collected. The levels of IL-8 in the supernatants were determined by ELISA (BD Biosciences, La Jolla, Calif.). Human cell cultures were treated with 10 ng/mL LPS as the positive control. Cultures treated with LPS 10 ng/mL and compound 1 10 μM released averages of 14.5±0.6 ng/mL SD and 7.8±0.8 ng/mL SD of IL-8, respectively.

Type 1 IFN Assay.

L929 cells stably expressing an interferon sensitive response element (ISRE) luciferase reporter construct were kindly provided by Dr. B. Beutler (UT Southwestern, Texas). See e.g., Crozat, K. et al., *Mamm. Genome* 2006, 17:398-406. The bioactivity of type I IFN in mBMDC supernatants was measured by luciferase assay using L929-ISRE cells as described previously. See e.g., Crozat 2006 (Id.) L929-ISRE cells were plated at 5×10$^4$ cells per well in Dulbecco's Modified Eagle Medium (Invitrogen) supplemented with 10% FCS, 100 U/mL penicillin, and 100 μg/mL streptomycin (DMEM-10) in a 96-well white-walled clear-bottom plate. Thus, 50 μL of μBMDC supernatant was incubated with L929-ISRE cells in 50 μL of DMEM for 6 h. Mu-IFN Beta Standard (PBL Interferon Source, Piscataway, N.J.) was used as a standard. The luciferase activities were measured by Steady-Glo luciferase assay buffer (Promega, Madison, Wis.).

In addition, the levels of IP-10, a surrogate marker of type I IFN, in the supernatants were determined by ELISA (R&D Systems, Minneapolis, Minn.). The cultures stimulated with LPS 10 ng/mL, and 5 μM Cmpd 1 released an average of 234.8±8.6 and 590.0±10.5 pg/mL of IP-10, respectively.

In Vivo Evaluation.

C57BL/6J mice (female, 5-6 weeks old) were intravenously injected with Cmpd 1 (200 nmol in 200 μL 5% DMSO in saline solution). The sera were collected 4 hour after the administration. The cytokine levels in the sera were measure by Luminex® assay. In the studies of the adjuvant activities, the mice were intradermally injected OVA (100 μg/animal) and the compound (500 nmol/animal) in the skin of tails on day 0 and day 7. The serum samples were collected at day 28. The levels of OVA-specific IgG1 in the sera were measured by ELISA.[18]

Statistical Analysis.

The data are represented as mean±standard error of the mean (SEM). Prism 4 (GraphPad Software, San Diego, Calif.) statistical software was used to establish p-values for comparison between groups ($p<0.05$ was considered significant). For the in vitro studies, two tailed Student's t test was used to compare two groups, and one way ANOVA was used to compare the multiple groups. In in vivo studies, the Mann-Whitney test was used to compare two groups and two-way ANOVA was used for multiple group comparisons. Dunnett's post hoc test was used for multiple comparisons to a control group and Bonferonni's post hoc test for multiple pair-wise comparisons.

Example 8

Figure 10A:
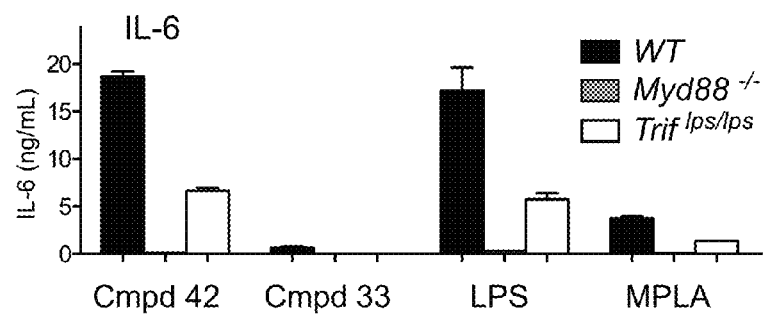
FIGS. 10A-10B depict histograms showing requirements of MyD88 and TRIF adaptor proteins. Bone marrow derived dendritic cells (BMMDC) were prepared from C57BL/6 mice, MyD88 null, or LPS mutant mice (C57BL/6 background) BMDC were incubated with 5 µM Cmpd 42 or Cmpd 33 overnight, and the levels of IL-6 (FIG. 10A) and IP-10 (FIG. 10B) were measured by ELISA. IP-10 was used for the surrogate marker of type 1 IFN. LPS (10 ng/mL) and MPLA (1 µg/mL) were used as positive controls. Histogram legend (left to right) for each group (left to right) of Cmpd 42, Cmpd 33, LPS, and MPLA: WT, solid box; Myd88$^{-/-}$, gray box; Trif$^{lps/lps}$, open box.
Figure 10B:
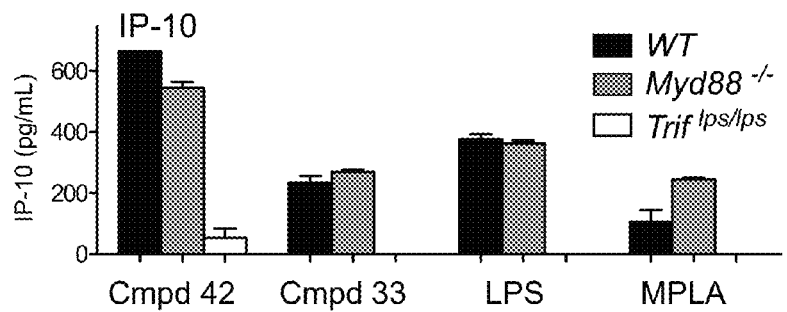

Cmpd 42 and Cmpd 33 Require MyD88 and TRIF Adaptor Proteins for Cytokine Induction To evaluate adaptor protein requirements, bone marrow derived dendritic cells (BMMDC) prepared from C57BL/6 mice, MyD88 null, or LPS mutant mice were stimulated with Cmpd 42 and Cmpd 33. As depicted in FIG. 10A, IL-6 secretion induced by both Cmpd 42 and Cmpd 33 was significantly impaired in MyD88 null dendritic cells. As depicted in FIG. 10B, IP-10 induction significantly decreased in LPS mutant cells. These data indicated that MyD88 and LPS2 are essential for induction of IL-6 and type 1 IFN by both compounds.

Example 9

Figure 11A:
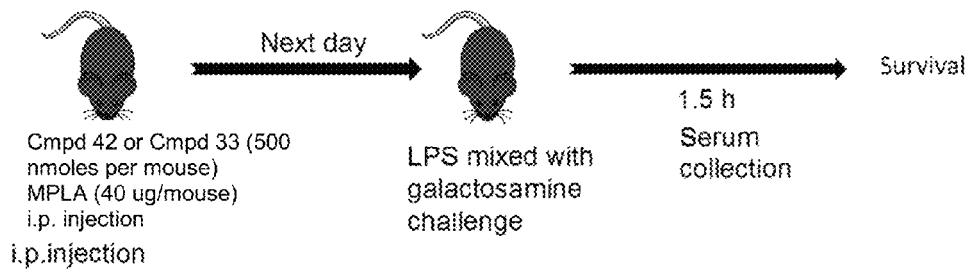
FIGS. 11A-11B depict that administration of Cmpd 42 and Cmpd 33 protects hosts from LPS-induced lethal liver injury.
Figure 11B:
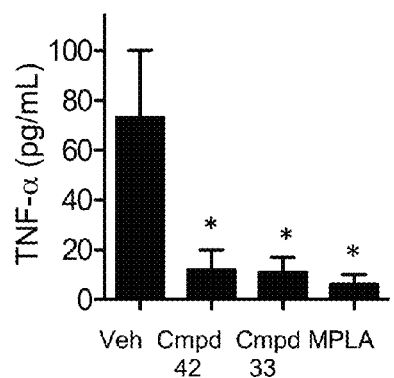

Administration with Cmpd 42 and Cmpd 33 Protects Hosts from LPS-Induced Lethal Liver Injury Lipopolysaccharide (LPS), a TLR4 ligand, causes severe lethal liver injury when administered with galactosamine. Pretreatment of mice with MPLA is known to improve the survival in this model. To study whether Cmpd 42 and Cmpd 33 are able to act as immunomodulatory agents similar to MPLA, the mice were treated with Cmpd 42 or Cmpd 33 and challenged with LPS/galatosamine the next day, as depicted in FIG. 11A. Over 80% of Cmpd 42 and 100% of Cmpd 33-treated mice survived. See Table 4 following. As depicted in FIG. 11B, a significantly lower level of TNFα was detected in Cmpd 42- or Cmpd 33-treated mice. These data indicated that treatment with Cmpd 42 and Cmpd 33 prevented liver injury induced by LPS/galactosamine administration.

TABLE 4

Summary of Survival for Example 9

| Treatment | Route | Survival |
|---|---|---|
| Vehicle | i.p. | 2/9 |
| Cmpd 42 | i.p. | 9/11 |
| Cmpd 33 | i.p. | 11/11 |
| MPLA | i.p. | 8/9 |

Example 10

Cmpds 42 and 33 do not Cause Liver Toxicity

Figure 12:
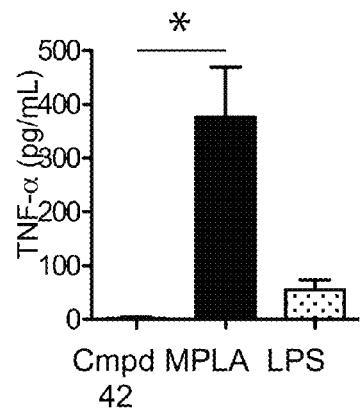
FIG. 12 depicts histogram showing that the effective dose of Cmpd 42 to prevent liver injury does not exhibit liver toxicity. C57BL/6 mice were i.p. injected with 500 nmol Cmpd 42, MPL (40 µg) or LPS (0.2 µg) mixed with galactosamine (12 mg). Sera were collected 1.5 h post challenge. *:p<0.05 compared to vehicle treated mice. Histogram order (left to right): Cmpd 42, MPLA, LPS.

The toxicity of Cmpd 42 was evaluated in a liver injury model. Mice were injected with Cmpd 42 or MPLA with galactosamine, and both survival and serum TNFα were measured. See Table 5 following. 100% of mice survived in Cmpd 42 treated groups whereas more than 90% of mice infected with LPS or MPLA are survived. As depicted in FIG. 12, a significantly lower level of TNFα was observed in the Cmpd 42-treated animals compared to MPLA and LPS-treated animals. These data indicated that treatment dose of Cmpd 42 does not show any toxicity in the liver injury models.

TABLE 5

Summary of Survival for Example 10

| Treatment | Survival |
|---|---|
| Cmpd 42/Gal | 5/5 |
| MPLA/Gal | 0/5 |
| LPS/Gal | 1/5 |

Figure 13:
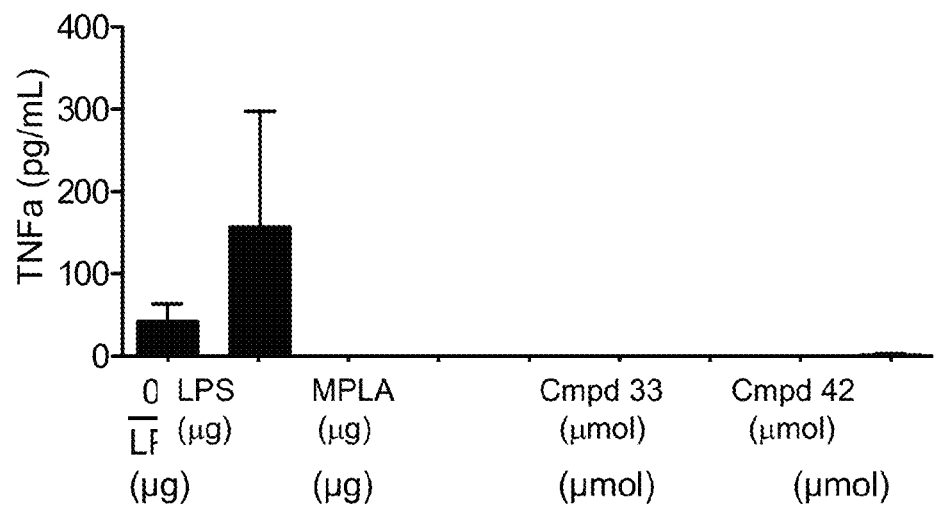
FIG. 13 depicts histogram showing that Cmpd 42 and Cmpd 33 are safe in a liver injury model. C57BL/6 mice n=3 were i.p. injected with indicated doses (per animal) of Cmpd 42, Cmpd 33, MPLA or LPS in combination of galactosamine (12 mg/animal). Sera were collected 1.5 h post challenge. Histogram order (left to right): LPS (0.2 µg); MPLA (10, 1, 0.1 µg); Cmpd 33 (15, 3, 0.6 jug); Cmpd 42 (1, 0.2 µg).

To further confirm the safety of Cmpd 42 and Cmpd 33, up to 15 mmol Cmpd 42 or 1 µmol Cmpd 33 were administered to C57BL/6 mice with galactosamine. As depicted in FIG. 13, serum levels of TNFα was compared to the mice injected with MPLA plus galacosamine. Serum TNFα levels were not affected by administration with up to 15 µmol/animal (6.5 mg/animal) Cmpd 33 and 1 µmol/animal (445 µg/animal) Cmpd 42. In contrast, 10 µg/animal MPLA induced detectable TNFα in sera. These data indicated that maximum tolerated doses of Cmpd 33 and Cmpd 42 in this model are over 100 times and 10 times higher than MPLA, respectively.

Example 11

Cmpd 42 is Orally Bioavailable in Mice

Figure 14:
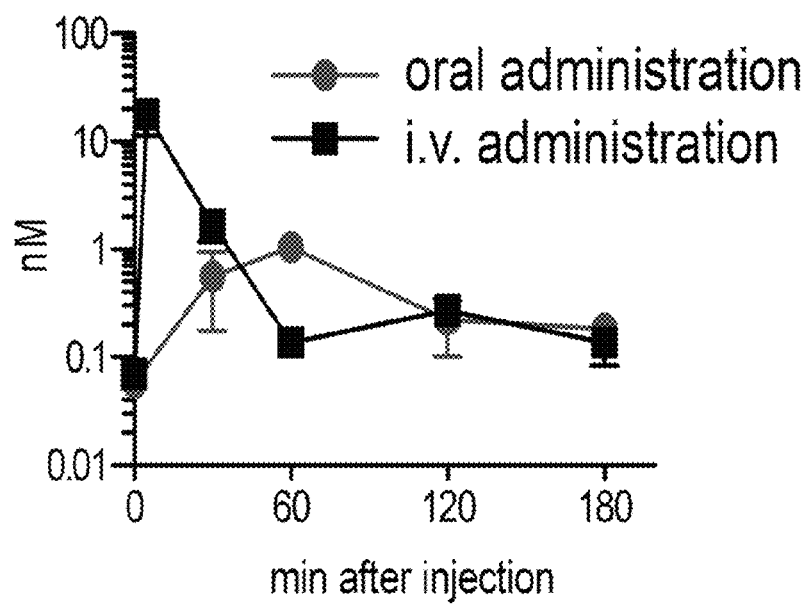
FIG. 14 depicts time course showing that Cmpd 42 is orally bioavailable in mice. C57BL/6 mice were intravenously (500 nmol) or orally (1 µmol) administered with Cmpd 42. Sera were collected at the indicated time point and concentration of the compound were measured by LC/MS. Legend: oral administration, closed circle; i.v. administration, closed box. X-axis: time (min). Y-axis: concentration of Cmpd 42 (nM).

To test oral bioavailability, Cmpd 42 was orally or intravenously administered to C57BL/6 mice and the drug concentration in sera was measured. Results are depicted in FIG. 14. Based on calculations using the method of the area under the curve as known in the art, the oral bioavailability of Cmpd 42 was about 15%.

Example 12

Figure 15A:
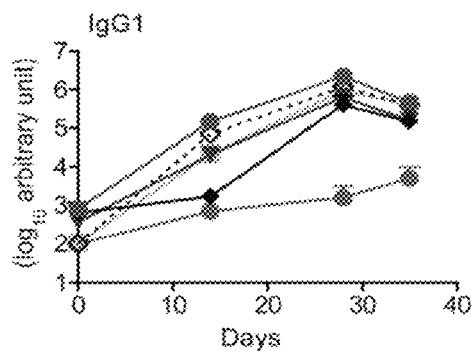
FIGS. 15A-15G depict that the combination of Cmpd 42 and TLR7 agonist (1V270) enhanced early production of antigen specific antibody. C57BL/6 mice were intramuscularly immunized with 20 µg ovalbumin (OVA) mixed with the following adjuvants: 200 nmol Cmpd 42, 200 nmol Cmpd 33, 10 nmol 1V270, 200 nmol Cmpd 42 plus 10 nmol 1V270 or MPLA. Vehicle (5% DMSO in saline) was used as a control. Sera were collected on day 0, 14, 28 and 35, and OVA specific IgG1 (FIG. 15A) and IgG2c (FIG. 15B) were determined by ELISA. Splenocytes were harvested on day 35 and cultured with 100 µg/mL OVA for three days.
Figure 15B:
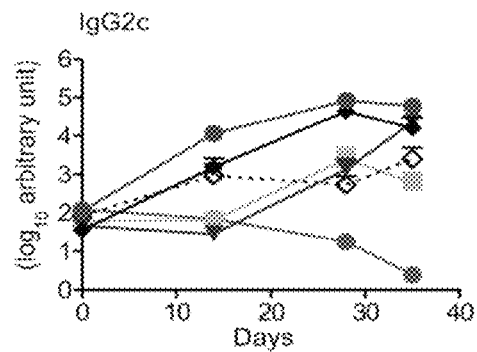
Figure 15C:
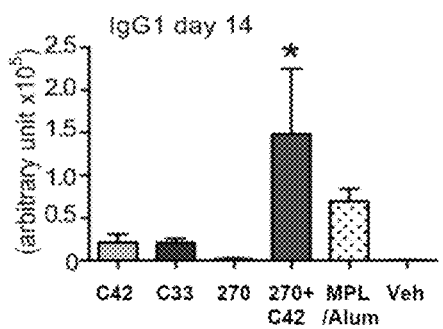
Figure 15D:
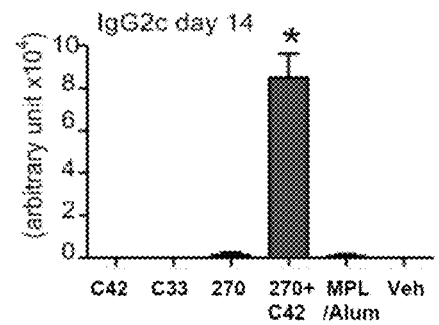
Figure 15E:
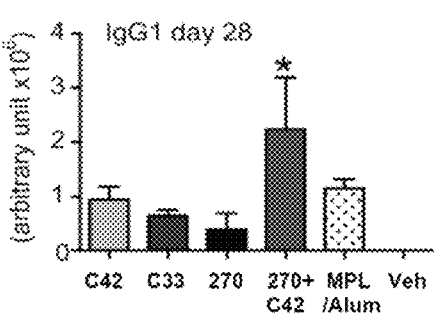
Figure 15F:
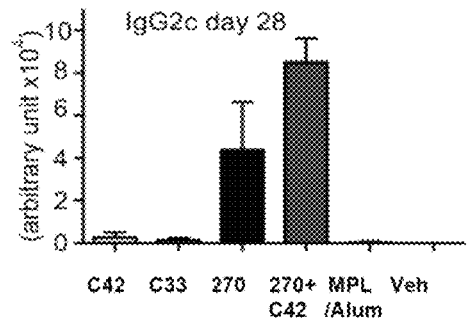
Figure 15G:
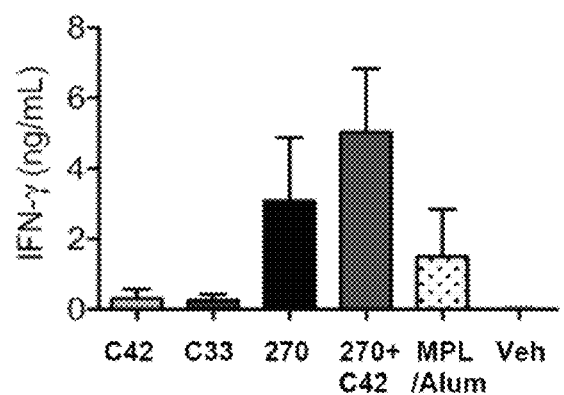

Vaccine Adjuvant Application: Combination of Cmpd 42 and TLR7 Agonist (1V270) Enhanced Early Production of Antigen Specific Antibody To evaluate adjuvant activity of Cmpd 42 and Cmpd 33, C57BL/6 mice were intramuscularly immunized with ovalbumin (OVA) mixed with Cmpd 42, Cmpd 33, compound 1V270 (i.e., TLR7 agonist as known in the art), Cmpd 42 plus 1V270, or MPLA. On day 14, rapid elevation of IgG1 and IgG2c were observed in mice immunized with the combination of Cmpd 42 and 1V270 (FIG. 15C and FIG. 15D). The levels of Ig were sustained on day 28 (FIG. 15E and FIG. 15F). The combination of Cmpd 42 and 1V270 also induced high level of antigen specific IFNγ. These data indicate that co-administration of TLR4- and TLR7-ligands can induce rapid humoral response and enhance the antigen specific T cell responses. The structure of compound 1V270 (see e.g., PCT/US2011/000757) follows:

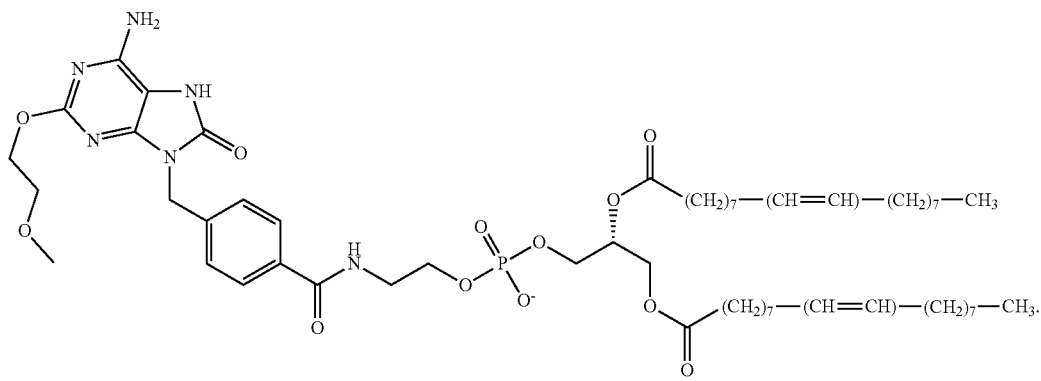

As depicted in FIGS. 15A-15G, the combination of Cmpd 42 with 1V270 gave rise to levels of IgG1, IgG2c, and IFN-γ which exceed the summed response for Cmpd 42 or 1V270 alone. Thus, the response of the combination of Cmpd 42 with 1V270 is synergistic relative to the response of either agent alone.

Example 13

Correlation of IL-6 and IP-10

The TLR4 transfectoma lines transmit their reporter signal after activation of the proinflammatory transcription factor, NFκB. As one might expect, the IL-6 secretion induced by the compounds in primary mBMDCs correlated well with their respective activities in mouse TLR4 transfectoma cell lines. With few exceptions, the most active compounds in the IL-6 assays were also those that showed the highest activity in the mTLR4 transfectoma line (Tables 1-3). In addition to stimulating the production of inflammatory cytokines (e.g., IL-6) by NFκB activation, TLR4 signaling can induce the production of type I IFN via the TRIF pathway, as known in the art. See e.g., Kawai, T., et al., *J. Immunol.* 2001, 167:5887-5894; Yamamoto, M., et al., *J. Immunol.* 2002, 169:6668-6672. This pathway results in the activation of interferon regulatory factors (IRF), which are nuclear transcription factors that promote the transcription of IFNs. Type I IFN is important for the activation of antigen presenting dendritic cells, leading to good adjuvant activity, and also promotes cellular defenses against a variety of pathogens, particularly RNA viruses. This host defense is aided by circulating interferon inducible factors such as IP-10. The TLR4 transfectoma reporter lines in this study did not utilize an interferon reporter system; hence, the IP-10 data does not correlate as closely as the IL-6 data.

Figure 16:
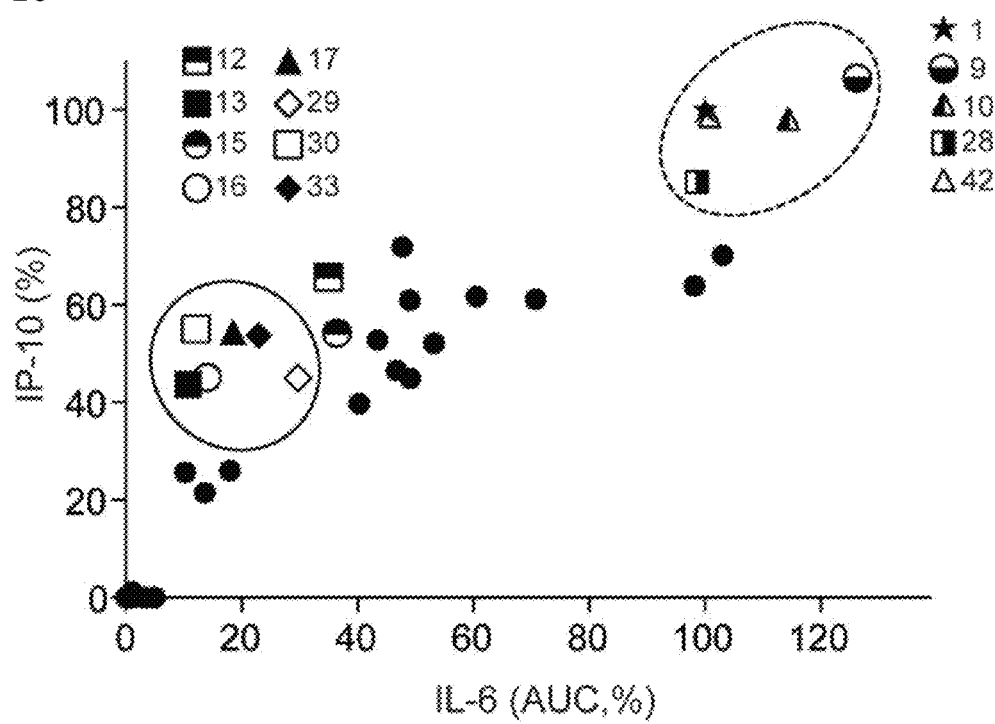
FIG. 16 depicts a correlation plot of IL-6 versus IP-10 induced by SAR derivatives disclosed herein. IL-6 (AUC) and IP-10 values in Tables 1-3 were plotted. Two distinct groups, compounds in the dotted circled (upper right) and in solid (left) circled areas, were selected based on the induction of IL-6 and IP-10. Numbers in the legends indicate compound ID. These clusters were selected based on mean±SD of the normalized IL-6 and IP-10 values of all SAR compounds. For IL-6, the mean±SD was 32±37. For IP-10, the mean±SD was 37±33. The group at the upper right area comprises compounds that induce high IL-6 and high IP-10 production, including compounds 1, 9, 10, 28, and 42, whose values were at least one SD above the mean for both cytokines. The other cluster is composed of compounds (Cmpds 13, 16, 17, 29, 30, and 33) that induce low IL-6 but relatively higher IP-10 production, whose values were below the mean for IL-6 and were above the mean for IP-10. Legend: Cmpd 1, star-symbol; Cmpd 9, circle filled at bottom; Cmpd 10, triangle closed at left; Cmpd 12, box filled at top; Cmpd 13, filled box; Cmpd 15, circle filled at top; Cmpd 16, open circle; Cmpd 17, filled triangle; Cmpd 28, box filled at right; Cmpd 29, open diamond; Cmpd 30, open box; Cmpd 33, filled triangle; Cmpd 42, open triangle.

Interestingly, several of the compounds, namely 12, 13, 15, 16, 17, 29, 30, and 33, induced diminished IL-6 release compared to Cmpd 1 but had nearly equivalent induction of IP-10 (Tables 1 and 2). These results suggest that there may be a possibility of separating the two activities on the basis of structural features. The correlation of IL-6 and IP-10 production of the selected compounds is shown graphically in FIG. 16. Two distinct groups of compounds are observed, shown as circled regions of the plot. Thus, the group at the upper right area (dotted circle) comprises compounds that induce high IL-6 and high IP-10 production, including Cmpds 1, 9, 10, 28, and 42. The other group is composed of compounds that induce low IL-6 but relatively higher IP-10 production. These two clusters were selected based on mean±SD of the normalized IL-6 and IP-10 values of all SAR compounds. For IL-6, the mean was 32±37. For IP-10, the mean was 37±33. The cluster in the dotted circle includes those compounds whose values were at least one SD above the mean for both cytokines. The other cluster includes those compounds whose values were below the mean for IL-6 and were above the mean for IP-10. It was notable that when the carboxamide substituent was phenyl or substituted phenyl (13, 15, 16, 17), with the exception of p-fluorophenyl (14), IL-6 release was reduced while IP-10 production was maintained at a relatively higher level. A few compounds bearing branched aliphatic carboxamide substituents showed a similar trend, as noted above for 29, 30, and 33.

In general, the active compounds exhibited greater activity in the murine cell systems than in human cells. Although the innate immune system is highly conserved among species, there are differences between human and mouse TLR4. See e.g., Ohto, U. et al., *Proc. Natl. Acad. Sci. U.S.A.* 2012, 109:S7421-S7426; Meng, J. et al., *J. Biol. Chem.* 2010, 285L27935-27943; Vasl, J. et al., *J. Immunol.* 2009, 183: 5138-5145. Similar to the active compounds reported herein, non-synthetic ligands have been noted to have species specific behavior. Notably, tetraacylated lipid IVa, a synthetic lipid A precursor, has been reported to act as a weak agonist to mouse TLR4/MD-2 but as an antagonist to human TLR4/MD-2. See e.g., Muroi, M.; Tanamoto, K.-i., *J. Biol. Chem.* 2006, 281:5484-5491; Saitoh, S.-i., et al., *Int. Immunol.*, 2004, 16:961-969. Recently mouse and human TLR4/MD2 crystal structures with this ligand have suggested that the different charge distributions of mouse and human TLR4/MD-2 affect the positions of the phosphate groups of lipid IVa, orienting them in a manner that would limit receptor dimerization by human TLR4. See e.g., Meng, J. et al., *J. Biol. Chem.* 2010, 285:27935-27943; Walsh, C. et al., *J. Immunol.* 2008, 181:1245-1254).

Various modifications of the present invention, in addition to those shown and described herein, will be apparent to those skilled in the art of the above description. Such modifications are also intended to fall within the scope of the appended claims.

Patents and publications mentioned in the specification are indicative of the levels of those skilled in the art to which the invention pertains. These patents and publications are incorporated herein by reference to the same extent as if each individual application or publication was specifically and individually incorporated herein by reference and for all purposes.

The foregoing description is illustrative of particular embodiments of the invention, but is not meant to be a XI. Embodiments Embodiment 1

A pharmaceutical composition comprising a pharmaceutically acceptable excipient and compound having the formula:

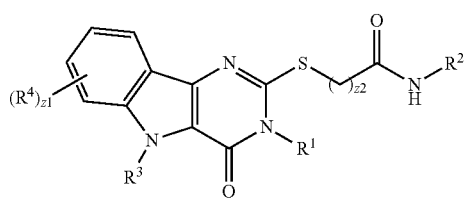

or a pharmaceutically acceptable salt thereof, wherein z1 is an integer from 0 to 4; z2 is an integer from 0 to 5; $R^1$ is substituted or unsubstituted cycloalkyl, substituted or unsubstituted heterocycloalkyl, substituted or unsubstituted aryl, or substituted or unsubstituted heteroaryl; $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, or substituted or unsubstituted alkyl; and $R^4$ is halogen, —CN, —SH, —OH, —COOH, —NH$_2$, —CONH$_2$, nitro, —CF$_3$, —CCl$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 2

The pharmaceutical composition of embodiment 1, wherein R is not p-fluorophenyl or p-methylphenyl.

Embodiment 3

The pharmaceutical composition of embodiment 1, wherein $R^1$ is not substituted phenyl.

Embodiment 4

The pharmaceutical composition of embodiment 1, wherein the compound is not

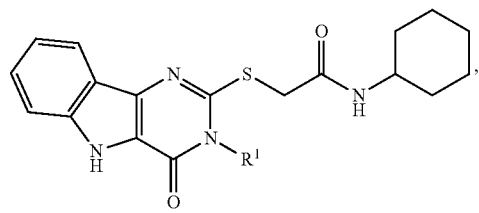

wherein $R^1$ is p-fluorophenyl or p-methylphenyl.

Embodiment 5

The pharmaceutical composition of embodiment 1, wherein the compound is not

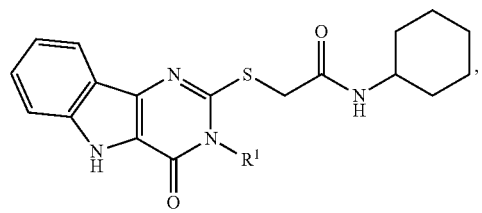

wherein $R^1$ is substituted phenyl.

Embodiment 6

The pharmaceutical composition of embodiment 1, wherein $R^2$ is not substituted or unsubstituted aryl, unsubstituted cyclohexyl, unsubstituted thiazole, or —CH$_2$-furanyl.

Embodiment 7

The pharmaceutical composition of embodiment 1, wherein the compound is not

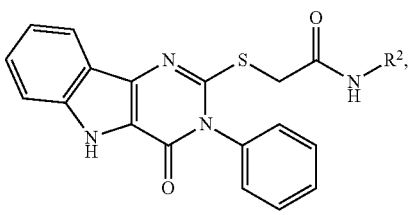

wherein $R^2$ is unsubstituted aryl, unsubstituted cyclohexyl, unsubstituted thiazole, or —CH$_2$-furanyl.

Embodiment 8

The pharmaceutical composition of embodiment 1, wherein the compound is not

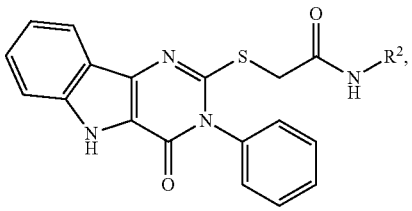

wherein $R^2$ is substituted or unsubstituted aryl, substituted or unsubstituted cyclohexyl, substituted or unsubstituted thiazole, or alkyl substituted with a substituted or unsubstituted furanyl.

Embodiment 9

The pharmaceutical composition of one of embodiments 1 to 8, wherein $R^1$ is substituted or unsubstituted cycloalkyl or substituted or unsubstituted aryl.

Embodiment 10

The pharmaceutical composition of one of embodiments 1 to 8, wherein $R^1$ is unsubstituted cycloalkyl or unsubstituted aryl.

Embodiment 11

The pharmaceutical composition of one of embodiments 1 to 8, wherein $R^1$ is substituted or unsubstituted $C_6$-$C_8$ cycloalkyl or substituted or unsubstituted phenyl.

Embodiment 12

The pharmaceutical composition of one of embodiments 1 to 8, wherein $R^1$ is substituted or unsubstituted $C_6$ cycloalkyl or substituted or unsubstituted phenyl.

Embodiment 13

The pharmaceutical composition of one of embodiments 1 to 8, wherein $R^1$ is $R^{1A}$-substituted or unsubstituted $C_6$ cycloalkyl or $R^{1A}$-substituted or unsubstituted phenyl, wherein $R^{1A}$ is a halogen.

Embodiment 14

The pharmaceutical composition of one of embodiments 1 to 8, wherein $R^1$ is $R^{1A}$-substituted or unsubstituted phenyl, wherein $R^{1A}$ is a halogen.

Embodiment 15

The pharmaceutical composition of one of embodiments 1 to 8, wherein $R^1$ is $R^{1A}$-substituted or unsubstituted phenyl, wherein $R^{1A}$ is a fluoro.

Embodiment 16

The pharmaceutical composition of one of embodiments 1 to 8, wherein $R^1$ is unsubstituted phenyl.

Embodiment 17

The pharmaceutical composition of one of embodiments 1 to 16, wherein $R^2$ is substituted or unsubstituted $C_4$-$C_{12}$ cycloalkyl, substituted or unsubstituted $C_3$-$C_{12}$ alkyl, substituted or unsubstituted aryl, or substituted or unsubstituted heteroaryl.

Embodiment 18

The pharmaceutical composition of one of embodiments 1 to 16, wherein $R^2$ is substituted or unsubstituted $C_4$-$C_{12}$ cycloalkyl, substituted or unsubstituted $C_4$-$C_{12}$ alkyl, substituted or unsubstituted aryl, or substituted or unsubstituted heteroaryl.

Embodiment 19

The pharmaceutical composition of one of embodiments 1 to 16, wherein $R^2$ is substituted or unsubstituted $C_4$-$C_{12}$ cycloalkyl, substituted or unsubstituted $C_4$-$C_{12}$ branched alkyl, or substituted or unsubstituted phenyl.

Embodiment 20

The pharmaceutical composition of one of embodiments 1 to 16, wherein $R^2$ is $R^{2A}$-substituted or unsubstituted $C_4$-$C_{12}$ cycloalkyl, $R^{2A}$-substituted or unsubstituted $C_4$-$C_{12}$ branched alkyl, or $R^{2A}$-substituted or unsubstituted phenyl, wherein $R^{2A}$ is halogen.

Embodiment 21

The pharmaceutical composition of one of embodiments 1 to 16, wherein $R^2$ is $R^{2A}$-substituted or unsubstituted $C_4$-$C_{12}$ cycloalkyl, $R^{2A}$-substituted or unsubstituted $C_4$-$C_{12}$ branched alkyl, or $R^{2A}$-substituted or unsubstituted phenyl, wherein $R^{2A}$ is fluoro.

Embodiment 22

The pharmaceutical composition of one of embodiments 1 to 16, wherein $R^2$ is unsubstituted $C_4$-$C_{12}$ cycloalkyl, unsubstituted $C_4$-$C_{12}$ branched alkyl, or $R^{2A}$-substituted or unsubstituted phenyl, wherein $R^{2A}$ is fluoro.

Embodiment 23

The pharmaceutical composition of one of embodiments 1 to 16, wherein $R^2$ is unsubstituted $C_6$-$C_{12}$ cycloalkyl, unsubstituted $C_4$-$C_{12}$ branched alkyl, or unsubstituted phenyl.

Embodiment 24

The pharmaceutical composition of one of embodiments 1 to 16, wherein $R^2$ is unsubstituted $C_6$-$C_{10}$ cycloalkyl.

Embodiment 25

The pharmaceutical composition of one of embodiments 1 to 16, wherein $R^2$ is unsubstituted $C_6$-$C_8$ cycloalkyl.

Embodiment 26

The pharmaceutical composition of one of embodiments 1 to 16, wherein $R^2$ is unsubstituted cyclohexyl.

Embodiment 27

The pharmaceutical composition of one of embodiments 1 to 26, wherein $R^3$ is hydrogen or substituted or unsubstituted alkyl.

Embodiment 28

The pharmaceutical composition of one of embodiments 1 to 26, wherein $R^3$ is hydrogen or unsubstituted alkyl.

Embodiment 29

The pharmaceutical composition of one of embodiments 1 to 26, wherein $R^3$ is hydrogen or unsubstituted $C_1$-$C_3$ alkyl.

Embodiment 30

The pharmaceutical composition of one of embodiments 1 to 26, wherein $R^3$ is hydrogen, methyl or ethyl.

Embodiment 31

The pharmaceutical composition of one of embodiments 1 to 26, wherein $R^3$ is methyl.

Embodiment 32

The pharmaceutical composition of one of embodiments 1 to 26, wherein $R^3$ is hydrogen.

Embodiment 33

The pharmaceutical composition of one of embodiments 1 to 32, wherein z2 is 1.

Embodiment 34

The pharmaceutical composition of one of embodiments 1 to 33, wherein z1 is 0 or 1.

Embodiment 35

The pharmaceutical composition of one of embodiments 1 to 33, wherein z1 is 1.

Embodiment 36

The pharmaceutical composition of one of embodiments 1 to 33, wherein z1 is 0.

Embodiment 37

The pharmaceutical composition of one of embodiments 1 to 35, wherein $R^4$ is substituted or unsubstituted heteroalkyl.

Embodiment 38

The pharmaceutical composition of one of embodiments 1 to 35, wherein the compound has the structure:

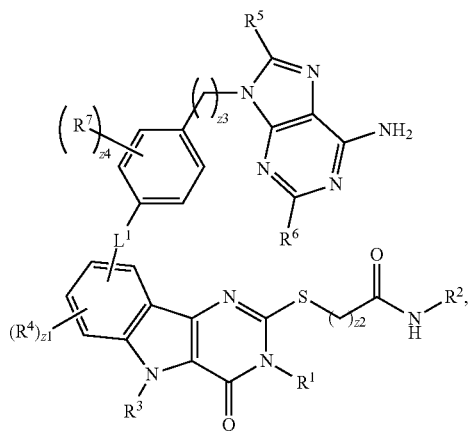

(IA)

wherein z3 is an integer from 1 to 10; z4 is an integer from 0 to 4; $L^1$ is substituted or unsubstituted alkylene or substituted or unsubstituted heteroalkylene; $R^5$ is —$SR^{5A}$ or —$OR^{5A}$; $R^{5A}$ is hydrogen, substituted or unsubstituted alkyl, substituted or unsubstituted heteroalkyl, substituted or unsubstituted heterocycloalkyl, substituted or unsubstituted cycloalkyl, substituted or unsubstituted aryl, or substituted or unsubstituted heteroaryl; $R^6$ is hydrogen, halogen, nitro, —OH, —SH, —CN, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^7$ is independently halogen, —CN, —SH, —OH, —COOH, —$NH_2$, —$CONH_2$, nitro, —$CF_3$, —$CCl_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 39

The pharmaceutical composition of embodiment 38, wherein z3 is 1 to 3.

Embodiment 40

The pharmaceutical composition of embodiment 38, wherein z3 is 1.

Embodiment 41

The pharmaceutical composition of embodiment 38, wherein z4 is 0.

Embodiment 42

The pharmaceutical composition of embodiment 38, wherein $R^5$ is —OH.

Embodiment 43

The pharmaceutical composition of embodiment 38, wherein $R^{5A}$ is hydrogen.

Embodiment 44

The pharmaceutical composition of embodiment 38, wherein $L^1$ is enzymatically cleavable.

Embodiment 45

The pharmaceutical composition of embodiment 38, wherein $L^1$ is —C(O)—$X^1$-$L^{1A}$-$X^2$—C(O)—, wherein $X^1$ and $X^2$ are —O— or —NH—; and $L^{1A}$ is substituted or unsubstituted alkylene or substituted or unsubstituted heteroalkylene.

Embodiment 46

The pharmaceutical composition of embodiment 45, wherein $L^{1A}$ is -$L^{1B}$-$(CH_2CH_2O)_n$— wherein n is an integer from 1 to 100 and $L^{1B}$ is unsubstituted $C_1$-$C_{10}$ alkyl.

Embodiment 47

The pharmaceutical composition of embodiment 46, wherein n is an integer from 1 to 10 and $L^{1B}$ is ethylene.

Embodiment 48

The pharmaceutical composition of embodiment 46, wherein $L^1$ is —C(O)O—$CH_2CH_2$—$(OCH_2CH_2)_n$—NH—C(O)—, wherein n is 1 to 10.

Embodiment 49

The pharmaceutical composition of embodiment 1, further comprising an antigen.

Embodiment 50

The pharmaceutical composition of embodiment 1, further comprising a TLR modulator.

Embodiment 51

A vaccine comprising an antigen and a compound having the formula:

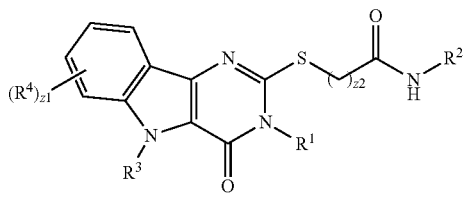

or a pharmaceutically acceptable salt thereof, wherein z1 is an integer from 0 to 4; z2 is an integer from 0 to 5; $R^1$ is substituted or unsubstituted cycloalkyl, substituted or unsubstituted heterocycloalkyl, substituted or unsubstituted aryl, or substituted or unsubstituted heteroaryl; $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, or substituted or unsubstituted alkyl; and $R^4$ is independently halogen, —CN, —SH, —OH, —COOH, —$NH_2$, —$CONH_2$, nitro, —$CF_3$, —$CCl_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 52

The vaccine of embodiment 51 further comprising a TLR modulator.

Embodiment 53

A biological cell comprising a compound having the formula:

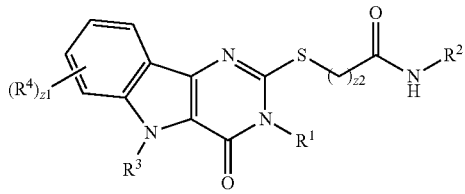

or a pharmaceutically acceptable salt thereof, wherein z1 is an integer from 0 to 4; z2 is an integer from 0 to 5; $R^1$ is substituted or unsubstituted cycloalkyl, substituted or unsubstituted heterocycloalkyl, substituted or unsubstituted aryl, or substituted or unsubstituted heteroaryl; $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, or substituted or unsubstituted alkyl; and $R^4$ is independently halogen, —CN, —SH, —OH, —COOH, —$NH_2$, —$CONH_2$, nitro, —$CF_3$, —$CCl_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 54

The biological cell of embodiment 53, wherein said biological cell forms part of an organism.

Embodiment 55

The biological cell of embodiment 54, wherein said organism is a human.

Embodiment 56

A mixture comprising a TLR modulator and a compound having the formula:

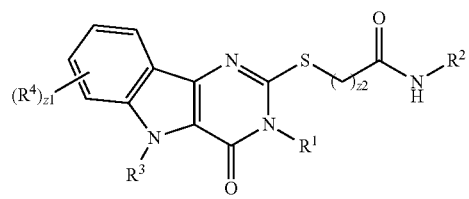

or a pharmaceutically acceptable salt thereof, wherein z1 is an integer from 0 to 4; z2 is an integer from 0 to 5; $R^1$ is substituted or unsubstituted cycloalkyl, substituted or unsubstituted heterocycloalkyl, substituted or unsubstituted aryl, or substituted or unsubstituted heteroaryl; $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, or substituted or unsubstituted alkyl; and $R^4$ is independently halogen, —CN, —SH, —OH, —COOH, —$NH_2$, —$CONH_2$, nitro, —$CF_3$, —$CCl_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 57

The mixture of embodiment 56, wherein said mixture is a liquid mixture or a powder mixture.

Embodiment 58

The mixture of embodiment 56, wherein said compound is present in an amount sufficient to increase the TLR modulator activity in a biological cell.

Embodiment 59

A method of modulating a Toll-like receptor 4 protein, said method comprising contacting the Toll-like receptor 4 protein with a compound having the formula:

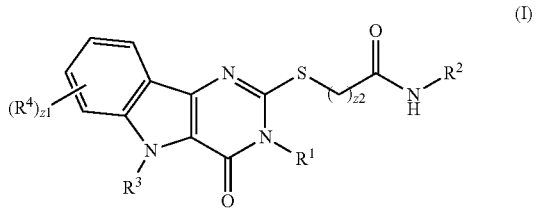

(I)

or a pharmaceutically acceptable salt thereof, wherein z1 is an integer from 0 to 4; z2 is an integer from 0 to 5; $R^1$ is substituted or unsubstituted cycloalkyl, substituted or unsubstituted heterocycloalkyl, substituted or unsubstituted aryl, or substituted or unsubstituted heteroaryl; $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, or substituted or unsubstituted alkyl; and $R^4$ is independently halogen, —CN, —SH, —OH, —COOH, —NH$_2$, —CONH$_2$, nitro, —CF$_3$, —CCl$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 60

A method of modulating an immune response in a subject in need thereof, said method comprising administering to the subject an effective amount of a compound having the formula:

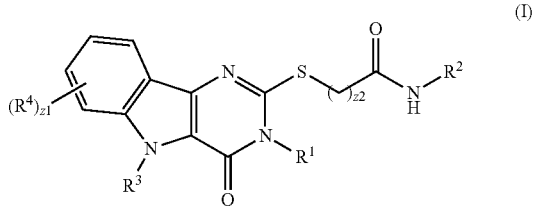

(I)

or a pharmaceutically acceptable salt thereof, wherein z1 is an integer from 0 to 4; z2 is an integer from 0 to 5; $R^1$ is substituted or unsubstituted cycloalkyl, substituted or unsubstituted heterocycloalkyl, substituted or unsubstituted aryl, or substituted or unsubstituted heteroaryl; $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, or substituted or unsubstituted alkyl; and $R^4$ is independently halogen, —CN, —SH, —OH, —COOH, —NH$_2$, —CONH$_2$, nitro, —CF$_3$, —CCl$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 61

The method of embodiment 60, wherein said subject is a cancer patient and said modulating comprises increasing an immune response to a cancer cell relative to the absence of said compound.

Embodiment 62

The method of embodiment 60, wherein said subject is an infectious disease patient and said modulating comprises increasing an immune response to a pathogen relative to the absence of said compound.

Embodiment 63

The method of embodiment 60, wherein said subject is an autoimmune disease patient and said modulating comprises decreasing an immune response to an endogenous antigen causing said autoimmune disease relative to the absence of said compound.

Embodiment 64

A method of decreasing inflammation in a subject in need thereof, said method comprising administering to the subject an effective amount of a compound having the formula:

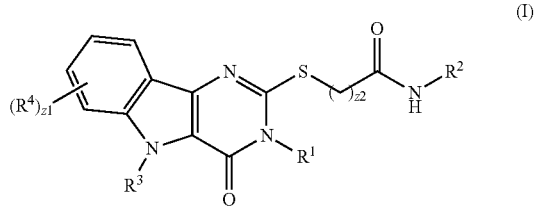

(I)

or a pharmaceutically acceptable salt thereof, wherein z1 is an integer from 0 to 4; z2 is an integer from 0 to 5; $R^1$ is substituted or unsubstituted cycloalkyl, substituted or unsubstituted heterocycloalkyl, substituted or unsubstituted aryl, or substituted or unsubstituted heteroaryl; $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, or substituted or unsubstituted alkyl; and $R^4$ is independently halogen, —CN, —SH, —OH, —COOH, —NH$_2$, —CONH$_2$, nitro, —CF$_3$, —CCl$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 65

A compound having the formula:

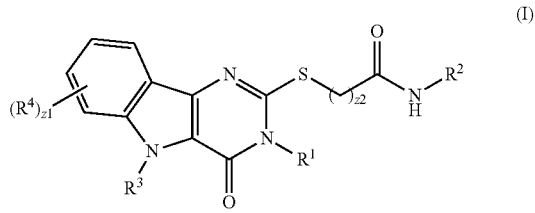

(I)

or a pharmaceutically acceptable salt thereof, wherein z1 is an integer from 0 to 4; z2 is an integer from 0 to 5; $R^1$ is substituted or unsubstituted cycloalkyl, substituted or unsubstituted heterocycloalkyl, substituted or unsubstituted aryl, or substituted or unsubstituted heteroaryl; $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, or substituted or unsubstituted alkyl; and $R^4$ is independently halogen, —CN, —SH, —OH, —COOH, —NH$_2$, —CONH$_2$, nitro, —CF$_3$, —CCl$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein:

(i) the compound is not

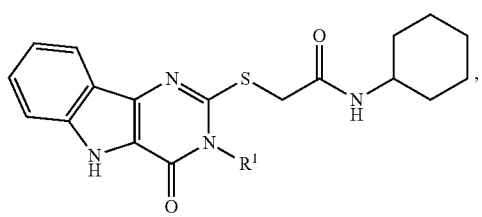

wherein $R^1$ is p-fluorophenyl or p-methylphenyl;

(ii) wherein the compound is not

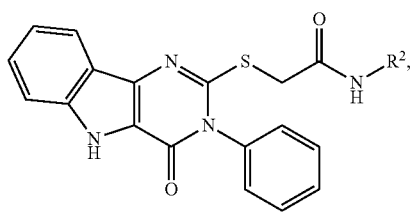

wherein $R^2$ is unsubstituted aryl, unsubstituted cyclohexyl, unsubstituted thiazole, or —CH$_2$-furanyl; or (iii) $R^3$ is not hydrogen.

Embodiment 66

The compound of embodiment 65, wherein $R^1$ is not substituted phenyl.

Embodiment 67

The compound of embodiment 65, wherein $R^1$ is not p-fluorophenyl or p-methylphenyl.

Embodiment 68

The compound of embodiment 65, wherein the compound is not

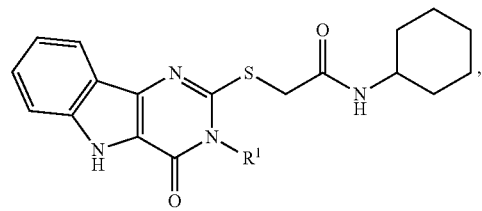

wherein $R^1$ is substituted phenyl.

Embodiment 69

The compound of embodiment 65, wherein $R^2$ is not substituted or unsubstituted aryl, unsubstituted cyclohexyl, unsubstituted thiazole, or —CH$_2$-furanyl.

Embodiment 70

The compound of embodiment 65, wherein the compound is not

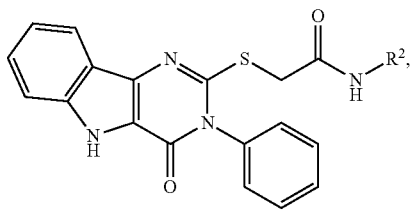

wherein $R^2$ is substituted or unsubstituted aryl, substituted or unsubstituted cyclohexyl, substituted or unsubstituted thiazole, or alkyl substituted with a substituted or unsubstituted furanyl.

What is claimed is:

1. A pharmaceutical composition comprising a pharmaceutically acceptable excipient and compound having the formula:

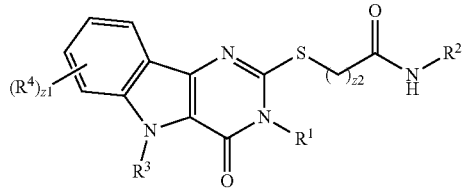

(I)

or a pharmaceutically acceptable salt thereof, wherein z1 is an integer from 0 to 4;

z2 is an integer from 0 to 5;

$R^1$ is substituted or unsubstituted cycloalkyl, substituted or unsubstituted heterocycloalkyl, substituted or unsubstituted aryl, or substituted or unsubstituted heteroaryl;

$R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, or substituted or unsubstituted alkyl; and $R^4$ is independently halogen, —CN, —SH, —OH, —COOH, —NH$_2$, —CONH$_2$, nitro, —CF$_3$, —CCl$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

2. The pharmaceutical composition of claim 1, wherein $R^1$ is substituted or unsubstituted cycloalkyl or substituted or unsubstituted aryl.

3. The pharmaceutical composition of claim 1, wherein $R^2$ is substituted or unsubstituted $C_4$-$C_{12}$ cycloalkyl, substituted or unsubstituted $C_3$-$C_{12}$ alkyl, substituted or unsubstituted aryl, or substituted or unsubstituted heteroaryl.

4. The pharmaceutical composition of claim 1, wherein z2 is 1.

5. The pharmaceutical composition of claim 1, wherein $R^4$ is independently substituted or unsubstituted heteroalkyl.

6. The pharmaceutical composition of claim 1, wherein the compound has the structure:

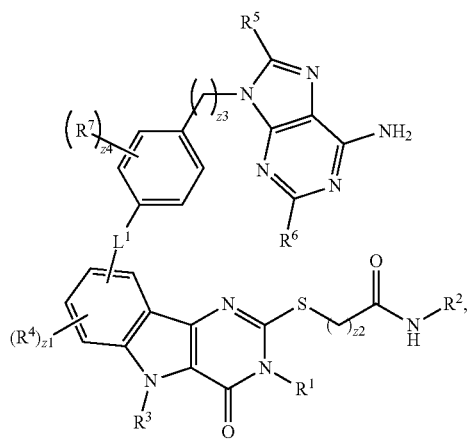

(IA)

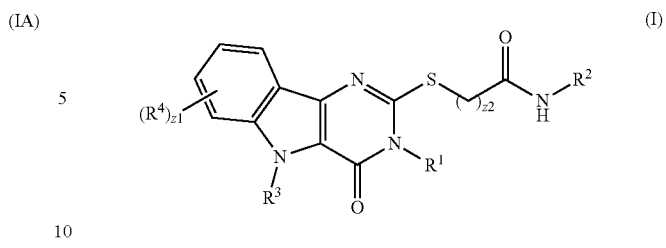

(I)

or a pharmaceutically acceptable salt thereof,
wherein
z1 is an integer from 0 to 4;
z2 is an integer from 0 to 5;
$R^1$ is substituted or unsubstituted cycloalkyl, substituted or unsubstituted heterocycloalkyl, substituted or unsubstituted aryl, or substituted or unsubstituted heteroaryl;
$R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$ is hydrogen, or substituted or unsubstituted alkyl; and
$R^4$ is independently halogen, —CN, —SH, —OH, —COOH, —NH$_2$, —CONH$_2$, nitro, —CF$_3$, —CCl$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

13. A method of decreasing inflammation associated with arthritis in a subject in need thereof, said method comprising administering to the subject an effective amount of a compound having the formula:

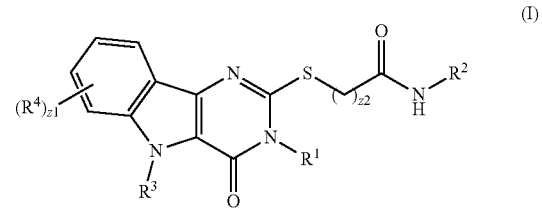

(I)

or a pharmaceutically acceptable salt thereof,
wherein
z1 is an integer from 0 to 4;
z2 is an integer from 0 to 5;
$R^1$ is substituted or unsubstituted cycloalkyl, substituted or unsubstituted heterocycloalkyl, substituted or unsubstituted aryl, or substituted or unsubstituted heteroaryl;
$R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^3$ is hydrogen, or substituted or unsubstituted alkyl; and
$R^4$ is independently halogen, —CN, —SH, —OH, —COOH, —NH$_2$, —CONH$_2$, nitro, —CF$_3$, —CCl$_3$, substituted or unsubstituted alkyl, substituted or unsubstituted heteroalkyl, substituted or unsubstiwherein
z3 is an integer from 1 to 10;
z4 is an integer from 0 to 4;
$L^1$ is substituted or unsubstituted alkylene or substituted or unsubstituted heteroalkylene;
$R^5$ is —SR$^{5A}$ or —OR$^{5A}$;
$R^{5A}$ is hydrogen, substituted or unsubstituted alkyl, substituted or unsubstituted heteroalkyl, substituted or unsubstituted heterocycloalkyl, substituted or unsubstituted cycloalkyl, substituted or unsubstituted aryl, or substituted or unsubstituted heteroaryl;
$R^6$ is hydrogen, halogen, nitro, —OH, —SH, —CN, —COOH, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
$R^7$ is independently halogen, —CN, —SH, —OH, —COOH, —NH$_2$, —CONH$_2$, nitro, —CF$_3$, —CCl$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

7. The pharmaceutical composition of claim 6, wherein $L^1$ is enzymatically cleavable.

8. The pharmaceutical composition of claim 6, wherein $L^1$ is —C(O)—X$^1$-L$^{1A}$-X$^2$—C(O)—, wherein
X$^1$ and X$^2$ are —O— or —NH—; and
$L^{1A}$ is substituted or unsubstituted alkylene or substituted or unsubstituted heteroalkylene.

9. The pharmaceutical composition of claim 8, wherein $L^{1A}$ is -L$^{1B}$-(CH$_2$CH$_2$O)$_n$— wherein n is an integer from 1 to 100, and $L^{1B}$ is unsubstituted C$_1$-C$_{10}$ alkyl.

10. The pharmaceutical composition of claim 1, further comprising an antigen.

11. The pharmaceutical composition of claim 1, further comprising a TLR modulator.

12. A mixture comprising a TLR modulator and a compound having the formula:

tuted cycloalkyl, substituted or unsubstituted heterocycloalkyl, substituted or unsubstituted aryl, or substituted or unsubstituted heteroaryl.

14. A compound having the formula:

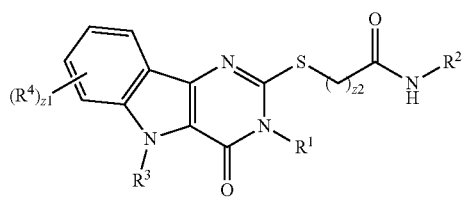
(I)

or a pharmaceutically acceptable salt thereof,
wherein
- z1 is an integer from 0 to 4;
- z2 is an integer from 0 to 5;
- $R^1$ is substituted or unsubstituted cycloalkyl, substituted or unsubstituted heterocycloalkyl, substituted or unsubstituted aryl, or substituted or unsubstituted heteroaryl;
- $R^2$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
- $R^3$ is hydrogen, or substituted or unsubstituted alkyl; and
- $R^4$ is independently halogen, —CN, —SH, —OH, —COOH, —NH$_2$, —CONH$_2$, nitro, —CF$_3$, —CCl$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein:
(i) the compound is not

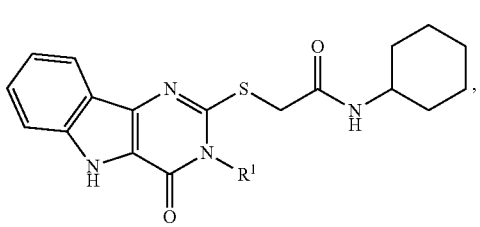

wherein $R^1$ is p-fluorophenyl or p-methylphenyl;
(ii) wherein the compound is not

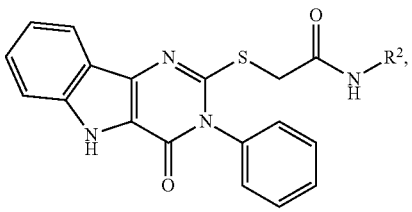

wherein $R^2$ is unsubstituted aryl, unsubstituted cyclohexyl, unsubstituted thiazole, or —CH$_2$-furanyl; or
(iii) $R^3$ is not hydrogen.

* * * * *